(12) United States Patent
Grinberg et al.

(10) Patent No.: US 7,939,562 B2
(45) Date of Patent: May 10, 2011

(54) AMPHIPHILIC DERIVATIVES FOR THE PRODUCTION OF VESICLES, MICELLES AND COMPLEXANTS, AND PRECURSORS THEREOF

(75) Inventors: Sarina Grinberg, Meitar (IL); Charles Linder, Rehovot (IL); Zeev Wiesman, Lehavim (IL); Eliahu Heldman, Rehovot (IL); Victoria Kolot, Beer-Sheva (IL)

(73) Assignee: Ben-Gurion University of The Negev Research and Development Authority, Beer-Sheva (IL)

( * ) Notice: Subject to any disclaimer, the term of this patent is extended or adjusted under 35 U.S.C. 154(b) by 874 days.

(21) Appl. No.: 10/250,933

(22) PCT Filed: Jan. 16, 2002

(86) PCT No.: PCT/IL02/00043
§ 371 (c)(1),
(2), (4) Date: Jul. 9, 2003

(87) PCT Pub. No.: WO02/055011
PCT Pub. Date: Jul. 18, 2002

(65) Prior Publication Data
US 2005/0118248 A1    Jun. 2, 2005

Related U.S. Application Data

(60) Provisional application No. 60/261,195, filed on Jan. 16, 2001.

(51) Int. Cl.
*A61K 31/20*    (2006.01)
*C07C 59/00*    (2006.01)
(52) U.S. Cl. .................... 514/558; 554/213; 562/579
(58) Field of Classification Search ........ 564/1; 560/12; 554/1, 8, 52
See application file for complete search history.

(56) References Cited

U.S. PATENT DOCUMENTS

| 3,453,067 | A | * | 7/1969 | Hueck et al. .................. 8/188 |
| 5,403,922 | A | * | 4/1995 | Garelli-Calvet et al. .... 536/1.11 |
| 5,434,307 | A |   | 7/1995 | Nwaonicha et al. |
| 5,530,148 | A | * | 6/1996 | Nwaonicha et al. ......... 554/114 |
| 5,811,129 | A | * | 9/1998 | Friedman et al. ............ 424/535 |

FOREIGN PATENT DOCUMENTS

| JP | 009222707 | 8/1997 |
| WO | WO 97/14713 | 4/1997 |
| WO | WO 98/42898 | 10/1998 |
| WO | 9921900 A1 | 5/1999 |

OTHER PUBLICATIONS

S.Grinberg, V. Kolot, D. Mills New Chemical derivatives based on *Vernonia galamensis* oil Industrial Crops and Products 3 (1994) 113-119 An International Journal.*
Ayorinde et al, Journal of the American Oil Chemists Society, Enzymatic Synthesis and Spectroscopic Characterization of 1,3-Diyernoloyl Glycerol from *Vernonia galamensis* Seed Oil, 70(2), pp. 129-132.*
Maerker et al, Journal of the American Oil Chemists Society, Epoxidation of Methyl Lineolate. I, 1966, 43, pp. 100-104.*
Fuhrhop, et al. *Routes to Functional Membranes without Proteins*, Angew. Chem. Int. Ed. Engl. 23, (1984), pp. 100-113.
Grinberg, et al. *Industrial Crops and Products*, 3, (1994), pp. 113-119.
Kunitake, et al. *Formation of Stable Bilayer Assemblies in Water from Single Chain Amphiphiles. Relationship between the Amphiphile Structure and the Aggregate Morphology*, J. Am. Chem. Soc., 103, (1981), pp. 5401-5413.
Kunitake, et al. *Vesicles of Polymeric Bilayer and Monolayer Membranes*, J. Am. Chem. Soc., 103, (1981), pp. 5945-5947.
Okahata, et al. *Formation of Stable Monolayer Membranes and Related Structures in Dilute Aqueous Solution from Two-Headed Ammonium Amphiphiles*, J. Am. Chem. Soc., 101, (1979), pp. 5231-5234.
Sumida, et al. *New pH-Sensitive Vesicles. Release Control of Trapped Materials from the Inner Aqueous Phase of Vesicles Made from Triple-Chain Amphiphiles Bearing Two Carboxylate Groups*, Langmuir, 17, (2001), pp. 609-612.
Groves et al., Membrane-spanning steroidal metalloporphyrins as site-selective catalysts in synthetic vesicles, J. Am. Chem. Soc., 109:5045-5047 (1987).
Overs et al., Assembly of new vic-Dihydroxyoctadecanoic acid methyl esters at the air-water interface, Langmuir, 16:1141-1148 (2000).
Menger et al., Chain-substituted lipids in monomolecular films, effect of polar substituents on molecular packing, Langmuir, 5:833-838 (1989).
Marnett et al., Hematia-catalyzed rearrangement of hydroperoxylinoleic acid to epoxy alcohols via an oxygen rebound, J. Am. Chem. Soc., 105:7001-7002 (1983).
Bayder et al., Novel quaternary ammonium salts derived from triglycerides and their application in skin and hair products, International Journal of Cometic Science, 13:169-190 (1991). Dahlqvist et al., Phospholipid: diacylglycerol acyltransferase: An enzyme that catalyzes the acyl-CoA-independent formation of triacylglycerol in yeast and plants, PNAS, 97(12)6487-6492 (2000).
Kato et al., Structural elucidation of naturally occurring 9,12,13-trihydroxy fatty acids by a synthetic study, Agric. Biol. Chem., 55(5):1349-1357 (1991).
Gerasyutina et al., Inhibitors of steel corrosion in sulfuric acid, Protection of Metals, 33:481-482 (1997).

* cited by examiner

*Primary Examiner* — Paul A Zucker
(74) *Attorney, Agent, or Firm* — Browdy and Neimark, PLLC

(57) ABSTRACT

Amphiphilic derivatives composed of at least one fatty acid chain are derived from natural vegetable oils such as vernonia oil, lesquerella oil and castor oil, in which the several reactive groups such as epoxy, hydroxy and double bonds can be modified to polar and ionic groups. The head group of the amphiphilic derivative may be in the main fatty acid chain or in a side chain. The amphiphiles are useful for the formation of vesicles and micelles and for use as complexants and surfactants.

46 Claims, 7 Drawing Sheets

AMPHIPHILIC DERIVATIVES FOR THE PRODUCTION OF VESICLES, MICELLES AND COMPLEXANTS, AND PRECURSORS THEREOF

FIELD OF THE INVENTION

The present invention relates to certain amphiphilic derivatives, to precursors thereof, and to vesicles, liposomes, micelles, and complexants made from said amphiphilic derivatives. These amphiphilic derivatives and products made therefrom can be used in the fields of medicine, agriculture, food industry, cosmetics and chemical industry.

BACKGROUND OF THE INVENTION

Amphiphilic or amphipathic derivatives are molecules containing both polar and hydrophobic domains. One important characteristic of some amphiphilic derivatives is their ability to self organize into different structures under appropriate conditions. For example, certain amphiphilic molecules, characterized by specific polar head groups such as anionic or zwitterionic groups and one or two alkyl chains of at least 8 carbon atoms, may organize themselves into vesicles of mono- and bilayer-membranes, which encapsulate the solutions in which they are formed. Amphiphilic molecules may also aggregate and organize themselves into micelle-type structures.

Monolayer membranes can be made from amphiphiles with at least two polar heads on either side of an aliphatic chain. When such amphiphiles, having two heads of different sizes, form monolayer membranes, they are classified into two categories—unsymmetrical or symmetrical, depending on a parallel or antiparallel molecular packing within the membrane.

Bilayer vesicles can be made from: (a) amphiphiles containing two dialkyl chains such as phospholipids or nonphosphorous derivatives; (b) single chain amphiphiles comprising a polar head group, a short flexible chain, a rigid segment and a relatively long flexible chain (Kunitake et al., 1981b); and (c) triple chain amphiphiles containing two ionic head groups (Sumida et al, 2001).

Vesicles made from synthetic amphiphiles or surfactants are called synthetic or surfactant vesicles. Vesicles made from synthetic or natural phospholipids are called liposomes. Liposomes and vesicles can be mechanically stabilized by mechanisms such as polymerization to form stronger and less permeable barriers. Vesicles made from a mixture of dissimilar aliphatic chains can form membranes with a mosaic distribution of different amphiphilic derivatives to improve control of membrane permeability or achieve specific adhesion properties of the vesicle. For example, the introduction of amphiphiles with perfluoroalkyl chains into a hydrocarbon membrane will result in the formation of perfluorinated domains which can, for example, be selectively removed to form micropores in the vesicle membrane (Fuhrhop and Mathieu, 1984).

Vesicle size is an important parameter in relation to penetration through biological barriers to reach target sites. Vesicle size also influences the mechanical stability and shelf life. Vesicles made from phospholipids and other amphiphilic compounds, which form bilayer membranes, characteristically range from 200 A to 10 microns in diameter. Monolayer vesicles may be made even smaller in diameter. For many applications requiring penetration through biological barriers, vesicle sizes smaller than 1000 A would be preferred, and in many cases still more preferred are vesicles in the size range of 200 A or less. However, obtaining small size vesicles concomitant with stability is generally problematic.

Amphiphilic derivatives and micelles, complexants, surfactants and vesicles derived therefrom have applications in many fields. In medicine, for example, liposomes can be used for drug delivery (e.g. of antibiotics, chemotherapeutical agents, etc.), for diagnostics (e.g. liposomes loaded with contrast material for imaging), and for gene therapy. In agriculture amphiphilic derivatives and related products are used in various formulation for the delivery of herbicides, pesticides and micro-nutrients. In the cosmetic industry, amphiphilic derivatives and related products are used widely in formulations of lotions, creams etc.

However, the currently available amphiphilic derivatives and their related products, in particular vesicles, suffer from serious drawbacks, which limits their use for many important applications. Major problems which limit the use of vesicles, complexants and micelles are stability in relation to production, shelf life, lifetime in biological environments, accessibility to target sites, and sustained viability after administration. Notably, many applications require nanosized vesicles, which at the present time are not sufficiently stable for commercial products. Small size, concomitant with stability, is especially important in applications requiring transport via multiple biological compartments before reaching the target site.

Amphiphilic derivatives, which contain a combination of multiple interactions within the hydrophobic chains (e.g. hydrogen bonding, polar, electrostatic and hydrophobic interactions, etc.) and between moieties in close proximity to the head groups, together with inter-reactive groups (e.g. double bond, —SH, epoxy groups etc.) may overcome such limitations. Moreover, in many cases, to achieve the required performance characteristics of amphiphilic derivatives and related products (e.g. biological and mechanical stability, targeting, penetration, etc.), efficient post-formation modifications of the vesicles, micelles or complexants should be performed. State of the art methods to modify vesicle surfaces include incorporation of lipid-pendant conjugates into the membrane during vesicle preparation, or modifying the vesicle surface by reacting the pendant with reactive surface groups. An important issue of stability is to avoid lipid-pendant conjugate removal from the vesicle membrane. Currently, the poor stability of the available amphiphilic products limits the number of chemical reactions that can be used for post-formation modification, and hence, restrict the number of applications. Especially for targeting and controlled release applications, complex functional groups are needed to achieve the necessary vesicle characteristics. Such amphiphilic derivatives are either currently not available or are very expensive to produce. Achieving improved amphiphilic characteristics may be possible with derivatives that contain a combination of inter-reactive groups for stability and available reactive sites for post-formation chemical modification to achieve nanosized vesicles with targeting and controlled release features.

In order to overcome the limitation of the state of the art, amphiphilic derivatives with functional moieties on the aliphatic chain as well as in close proximity to the polar head groups can be employed. Such derivatives will allow the formation of stable vesicles, complexants and micelles, which can readily undergo subsequent modifications, prevent the removal of conjugated surface pendants, and allow better targeting and release features. Such derivatives can be synthesized from functionalized oils such as vernonia oil, castor oil, lasquerella oil and epoxidized unsaturated oils like soy and linseed oils.

SUMMARY OF THE INVENTION

The present invention provides an amphiphilic derivative of the formula:

$$A_1\text{-CO-}A_2\text{-}A_3$$

wherein $A_1$ is a group —NH—$R_0$, —O—$R_0$, —S—$R_0$, or —O—PO(OH)—O—$R_0$, wherein $R_0$ is hydrogen, or optionally substituted hydrocarbyl;

$A_2$ is an alkylene chain of at least 5 carbon atoms;

$A_3$ is an aliphatic chain of at least 6 and at most 18 carbon atoms optionally carrying at least one double bond, said aliphatic chain being substituted by at least one polar, ionic and/or epoxy groups and/or by at least one moiety containing at least one polar, ionic and/or epoxy groups, said at least one polar, ionic and/or epoxy groups and at least one moiety containing at least one polar, ionic and/or epoxy groups being substitutions in any combination of 1-2, 1-2-3, 1-2-3-4, 1-2-4-5, 1-2-3-4-5, 1-2-4, 1-2-5, 1-3-4, 1-3, 1-5, 1-4, or 1-2-6 positions of the chain, the position 1 being arbitrarily assigned to the substitution most remote from the CO group, wherein either at least one polar or ionic group of said at least one polar, ionic and/or epoxy groups or of said at least one moiety containing at least one polar, ionic and/or epoxy groups of the $A_3$ chain is a head group, and/or the group $R_0$ in $A_1$ contains at least one polar or ionic head group.

The present invention also relates to vesicles, complexants and micelles which can be made from the amphiphilic derivatives. The amphiphiles and the products derived therefrom can be used in the fields of medicine, agriculture, nutrients, cosmetics and industry. In particular they may be useful in formulations for targeting and controlled release of low, intermediate and high molecular weight biologically active agents.

DETAILED DESCRIPTION OF THE INVENTION

Figure 1:
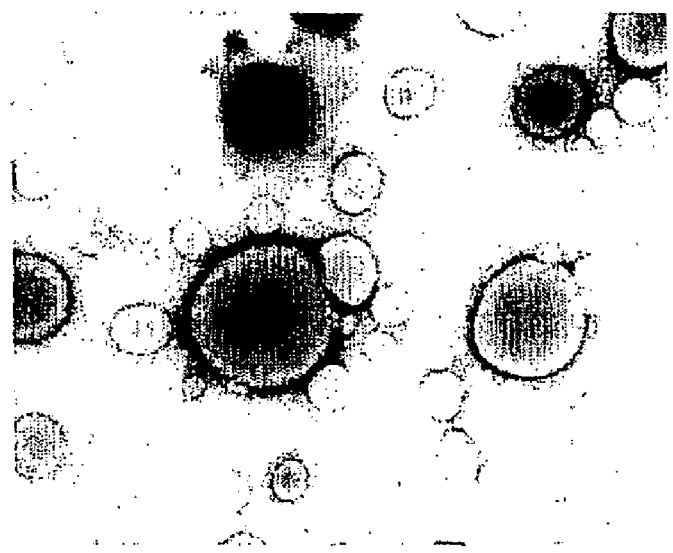
FIG. 1: TEM (transmission electron microscopy) photograph of Derivative 2 nanovesicles encapsulating 2% uranyl acetate. The vesicles shown in this photograph are in sizes ranging from 10 to 100 nm.

The present invention relates to amphiphilic compounds and precursors thereof, that can be prepared from naturally occurring vegetable oils. Functionalized oils are especially suitable because they contain groups which can readily undergo chemical reactions that yield versatile reactive amphiphilic derivatives. One preferred starting material is vernonia oil, but other oils such as castor, lesquerella and unsaturated oils like epoxidized soya and linseed oils can also be used. The precursors of the amphiphilic derivatives contain reactive groups such as epoxy, hydroxy, amino, —SH, haloacyloxy, allylic hydrogens, azide and double bonds. The precursors can also contain additional groups such as amide, sulfonamide, esters and ethers that are required of the amphiphilic derivatives to form self-assembling structures with improved stability. These precursors are used to prepare amphiphilic derivatives that contain a combination of functionalized groups and moieties within the aliphatic chain and/or in close proximity to the head groups. These functional groups allow multiple interactions between the hydrophobic chains (e.g. hydrogen bonding, polar, electrostatic and hydrophobic interactions, etc.) and between moieties that reside in close proximity to the head groups. These interactions lead to stable nanovesicles, complexants and micelles, which can be further chemically modified on their surface and/or within the membranes.

Preparation of Amphiphiles with Different Combinations of Polar, Ionic and/or Epoxy Groups in the Main Chain The present invention provides amphiphilic derivatives comprising at least one acyl aliphatic chain containing after the carbonyl of the acyl group a sequence of at least 5 carbon atoms without polar or ionic groups, wherein the remainder of the aliphatic chain contains at least 6 and at the most 18 carbon atoms, contains optionally a double bond and is substituted by at least one polar, ionic and/or epoxy group or by at least one moiety containing at least one polar, ionic and/or epoxy group, said multiple substitutions being in any combination of 1-2, 1-2-3, 1-2-3-4, 1-2-4-5, 1-2-3-4-5, 1-2-4, 1-2-5, 1-3-4, 1-3, 1-5, 1-4, or 1-2-6, positions wherein the position 1 is arbitrarily assigned to the position which is farthest from the carbonyl group. The preferred starting materials for making the above acyl chains are natural plant oils, in particular derivatives of Vernonia oil, Castor oil and Lesquerella oil, as well as of other fatty acids or their derivatives which contain in the fatty acid chain a combination of hydroxyl and/or epoxy groups and/or double bonds (e.g. allyl methyl groups, in effect methylene groups alpha to an olefin]. Through these reactive groups well-known methods in the art of chemistry can be carried out to get the different configurations of 1-2, 1-2-3, 1-2-3-4 or 1-2-3-4-5, 1-2-4, 1-2-5, 1-3-4, 1-3, 1-5, 1-4, 1-2-6, or 1-2-4-5.

The chemistry transformations below are given as one type of preferred example, but they are not to be considered limiting. For example, the acyl chains derived from vernonia, castor and lesquerella oil are given below, wherein the individual numbered reactive carbons may be modified according to the invention to produce the desired amphiphilic derivatives:

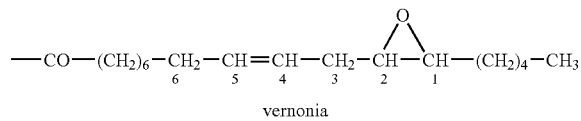
vernonia

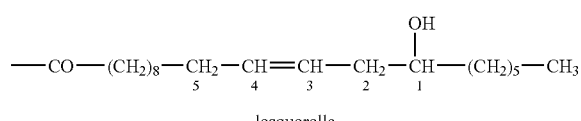
lesquerella

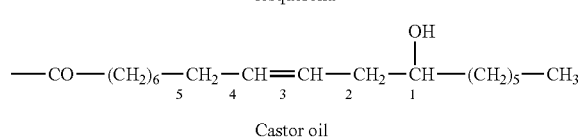
Castor oil

Any of the above carbons number 1 to 6 may be substituted in different combinations with polar or ionic groups as desired. For example, the epoxy group of vernonia may be substituted by different groups to give a 1-2 configuration. In one example as shown below, the epoxy group may be opened with a halocarboxylic acid such as chloroacetic acid to give a derivative wherein G1 is a haloacyloxy group (e.g. —OCOCH$_2$Cl) and G2 is —OH, or the epoxy group may be opened with an azide (e.g. NaN$_3$) and then reduced to —NH$_2$ to give a derivative wherein G1 is —NH$_2$ and G2 is —OH, or the epoxy is opened by Na2S then giving G1=—SH and G2=—OH. All these groups may be further derivatized at will. Thus, in the haloacyloxy OCOCH$_2$Cl group, the Cl may be further reacted with a tertiary amine, e.g. trimethyl amine, to give a quaternary ammonium group, or may be reacted with amino ethane sulfonic acid to give the corresponding aminoethane sulfonic acid derivative.

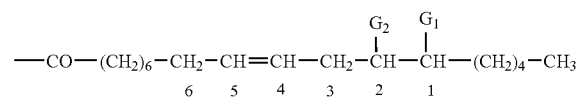

In another embodiment, the derivative above may be reacted with reagents which add across the double bond such as Br$_2$ thus forming derivatives with substitutions in positions 1-2-4-5 as shown below:

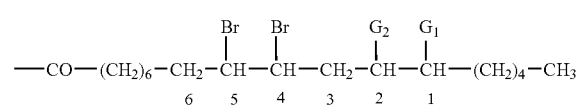

If reaction across the double bond is carried out with HBr, then derivatives with substitutions in positions 1-2-4 and 1-2-5 are formed as shown below:

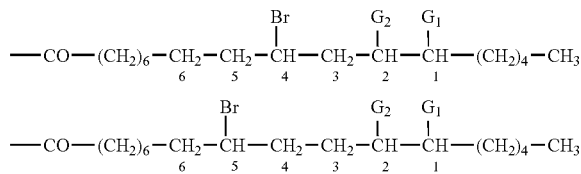

The —Br atoms may be readily reacted with compounds containing amino or sulfide groups to products containg anionic, cationic or zwitterionic groups. If the above bromo groups are replaced by —NH$_2$ or —SH groups or by moieties containing —NH$_2$ or —SH then derivatives are formed which may also be used to bind proteins, peptides, polysaccharides, DNA and RNA fragments In another embodiment, if vernonia oil below:

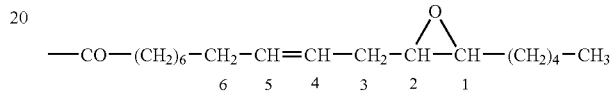

is subjected to N-bromosuccinamide/benzoyl peroxide+UV radiation, the 3 carbon is substituted with Br yielding the derivative:

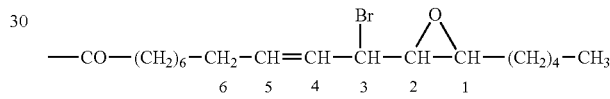

This bromo derivative may be further reacted with an amine to give:

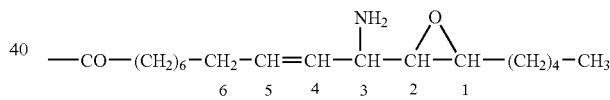

Then, upon opening the epoxy with Na+—OCOCH$_2$Cl, for example, the following derivative with a 1-2-3 combination is obtained:

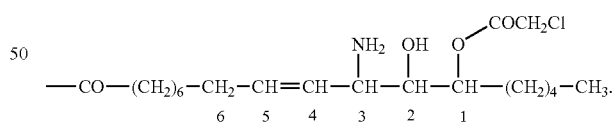

In another embodiment, the epoxy may be hydrolyzed to give:

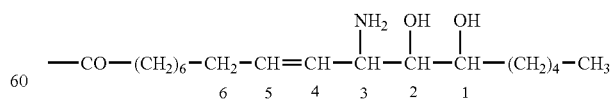

The amino group may be further reacted with well known reagents and conditions to give derivatives with anionic, cationic or zwitterionic moieties.

In another embodiment, if vernonia oil is reacted with N-bromo-succinamide/benzoyl peroxide/UV radiation in methylene chloride under conditions where the allyl H on the carbon atom 6 is substituted, then the derivative is formed:

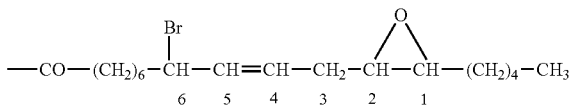

This derivative may be further reacted, for example with Na$_2$S, to give a 1-2-6 derivative below:

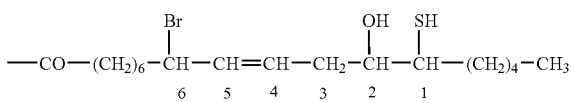

In another embodiment, if the acyl chain derived from lesquerella or castor oil is reacted with meta-chloroperoxybenzoic acid for epoxidation of the double bond, then the resulting derivatives are, respectively:

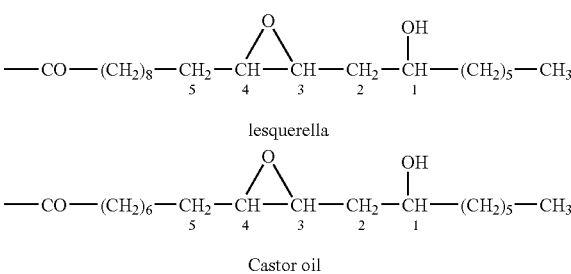

The epoxy may then undergo any of the reactions described in the specification. For example, the epoxy group may be opened and further reacted to give derivatives with substitutions in the 1-3-4 configuration as shown below, wherein G3 may be haloacyloxy (e.g. —OCOCH2Cl) and G4 may be —OH, or the epoxy may be opened with an azide and then reduced to —NH$_2$ to give G3=—NH2 and G4=—OH, or the epoxy is opened by Na$_2$S and G3=—SH and G4=—OH. The amino and the —SH as well as the —OH are readily derivatized to anionic, cationic or zwitterionic derivatives or they may be used to bind proteins, peptides, polysaccharides, DNA and RNA fragments.

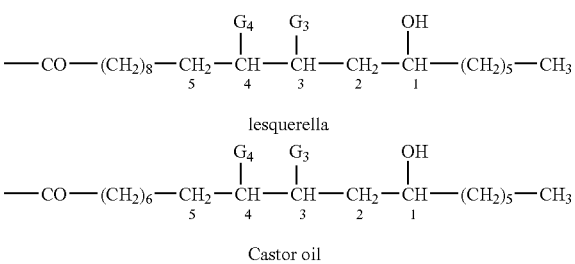

In another embodiment, other 1-3-4 derivatives may be synthesized if the acyl chain derived from lesquerella or castor oil are reacted with hypochlorous acid (HOCl) in water and then extracted into methylene chloride, and the following compounds may be obtained:

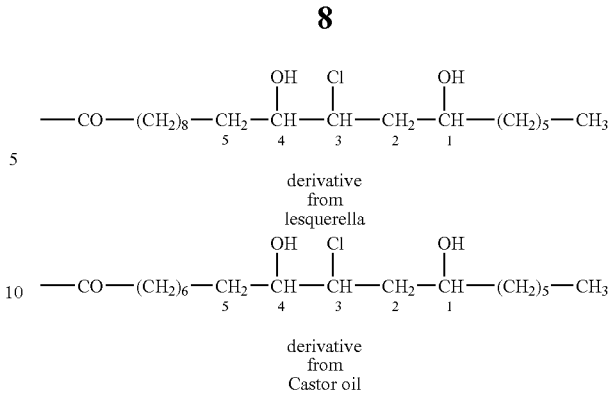

If the acyl chain of lesquerella or castor oil is reacted with N-bromosuccinamide/benzoyl peroxide/UV radiation in methylene chloride under conditions where the allyl Hs on both 2 and 5 carbons are substituted with Br, then the following 1-2-5 derivatives from lesquerella and castor oil are formed:

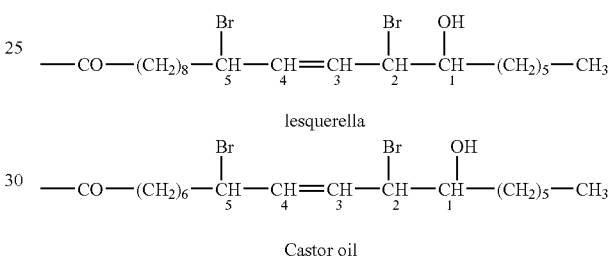

The —Br groups may be readily reacted as described above to give anionic, cationic and zwitterionic groups as described above. The above 1-2-5 derivatives may be further derivatized through the double bonds, with Br$_2$, for example, to give 1-2-3-4-5 substituted chains.

Both lesquerella or castor acyl chains may be reacted with N-bromosuccinamide/benzoyl peroxide/UV radiation in methylene chloride under conditions where only the allyl H on the second carbon atom has reacted, to give:

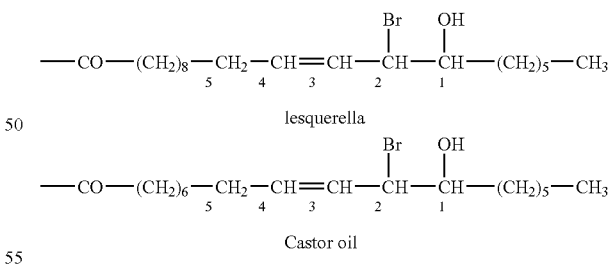

The —Br can be further reacted and derivatized as described above.

The above derivatives may be further reacted through the double bond with, for example, Br$_2$, to give 1-2-3-4 derivatives or with HBr to give 1-2-4 or 1-2-3 derivatives.

If both lesquerella or castor acyl chains are reacted with HBr or similar reagents which add across the double bond with a H radical adding to one carbon, then the 1-3 and 1-4 derivatives can be made. The HBr can also substitute the OH group with a bromide ion. The G group below can represent either OH or Br. The Br can be farther substituted by an amino or mercapto group, which in turn can be modified to form anionic, cationic or zwitterioric groups.

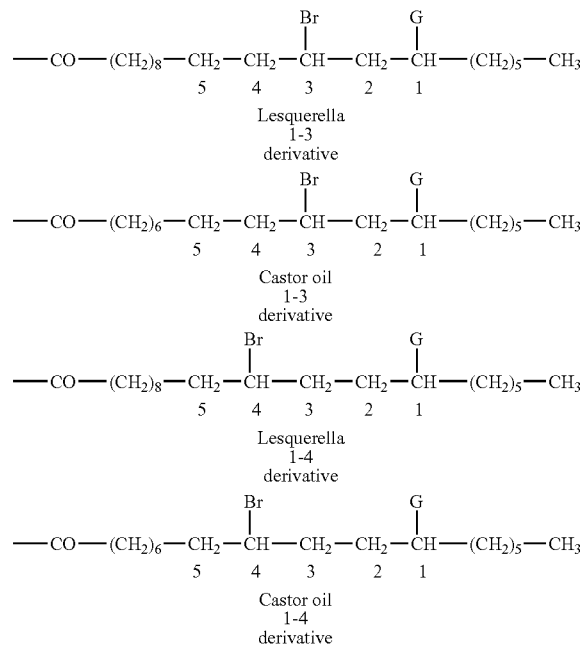

Lesquerella
1-3
derivative

Castor oil
1-3
derivative

Lesquerella
1-4
derivative

Castor oil
1-4
derivative

As described above, these derivatives may undergo further modification to substitute the Br with other groups or moieties to give polar or ionic groups or moieties as described above.

If both lesquerella or castor acyl chains are reacted with N-bromosuccinamide/benzoyl peroxide/UV radiation in methylene chloride under conditions where the allyl H on the 5 carbon is substituted with Br, these derivatives can be further derivatized as discussed above to give derivatives with polar and ionic groups in the 1-5 positions.

Definition of the Structures of the Amphiphilic Derivatives and Precursors of the Invention The present invention provides an amphiphilic derivative of the formula:

$A_1$-CO-$A_2$-$A_3$ wherein $A_1$ is a group —N—$R_0$, —O—$R_0$, —S—$R_0$, or —O—PO(OH)—O—$R_0$, wherein $R_0$ is hydrogen, or optionally substituted hydrocarbyl;

$A_2$ is an alkylene chain of at least 5 carbon atoms;

$A_3$ is an aliphatic chain of at least 6 and at most 18 carbon atoms optionally carrying at least one double bond, said aliphatic chain being substituted by at least one polar, ionic and/or epoxy groups and/or by at least one moiety containing at least one polar, ionic and/or epoxy groups, said at least one polar, ionic and/or epoxy groups and at least one moiety containing at least one polar, ionic and/or epoxy groups being substitutions in any combination of 1-2, 1-2-3, 1-2-3-4, 1-2-4-5, 1-2-3-4-5, 1-2-4, 1-2-5, 1-3-4, 1-3, 1-5, 1-4, or 1-2-6 positions of the chain, the position 1 being arbitrarily assigned to the substitution most remote from the CO group, wherein either at least one polar or ionic group of said at least one polar, ionic and/or epoxy groups or of said at least one moiety containing at least one polar, ionic and/or epoxy groups of the A3 chain is a head group, and/or the group $R_0$ in $A_1$ contains at least one polar or ionic head group.

In one embodiment of the invention, the amphiphilic derivative has only one fatty acid chain, the head group is not in the main chain and the derivative has the formula:

$A_1$-CO-$A_2$-$X_1$—$X_2$—$X_3$—$X_4$ wherein $A_1$ is a group —NH—$R_0$, —O—$R_0$, —S—$R_0$, or —O—PO(OH)—O$R_0$, wherein $R_0$ is hydrocarbyl substituted by at least one polar or ionic group head group and/or by at least one moiety containing at least one polar or ionic head group; $A_2$ is as defined in claim 1; $X_1$ is —CH═CH—; $X_3$ is 2,3-oxiranylene; and $X_2$ is $(CH_2)_n$ and $X_4$ is $(CH_2)_m$—$CH_3$, wherein each of n and m is at least 1 and n+m is at the most 13.

These compounds are derived from vernonia derivatives which have both a double bond and an epoxy group in the main fatty acid chain. The radical "2,3-oxiranylene" as used herein refers to the residue of the oxirane ring formed by the two carbons of the chain joined by the epoxy group.

In another embodiment, the amphiphilic derivative has only one fatty acid chain, which contains at least one head group and the side chain may or may not contain a head group, and the derivative has the formula:

$A'_1$-CO-$A'_2$-$X'_1$—$X'_3$—$X'_4$ wherein $A'_1$ is a group —NH—$R_0$, —O—$R_0$, —S—$R_0$, or —O—PO(OH)—O$R_0$, wherein $R_0$ is hydrocarbyl optionally substituted by at least one polar or ionic group head group and/or at least one moiety containing at least one polar or ionic head group; and -$A'_2$-$X'_1$—$X'_2$—$X'_3$—$X'_4$ represents a fatty acid chain containing at least one polar or ionic head group.

In a further embodiment, the amphiphilic derivative is composed of two fatty acid chains separated by a non-fatty acid midsection group (this "midsection group" is also herein called "spacer group"), each fatty acid chain being bound to the spacer group through a (thio)ester, phosphoester or amido bond and each fatty acid chain containing at least one head group and the spacer group may or may not contain an ionic head group. These derivatives are represented by the formula:

$X'''_4$—$X'''_3$—$X'''_2$—$X'''_1$-$A''_2$-CO-$Q_2$-$X_5$-$Q_1$-CO-$A'_2$-$X'_1$—$X'_2$—$X'_3$—$X'_4$ wherein $Q_1$ and $Q_2$, the same or different, represent —O—, —S—, —N(H)—, or —O—P0(OH)—O—;

-$A'_2$-$X'_1$—$X'_2$—$X'_3$—$X'_4$ and -$A''_2$-$X''_1$—$X''_2$—$X''_3$—$X''_4$ represent fatty acid chains each containing at least one ionic head group, wherein $A'_2$ and each of the $X'_1$ to $X'_4$ groups in the one chain may or may not be equivalent to $A''_2$ and each of the $X''_1$ to $X''_4$ groups in the other fatty acid chain; and the spacer group $X_5$ may be phenylene or alkylene optionally interrupted by one or more heteroatoms selected from O, S or NH, and may optionally contain at least one polar or ionic head group.

In a broad aspect that covers the many possibilities according to the invention, the present invention relates to an amphiphilic derivative or a precursor thereof, of the general Formula I:

$R_0$-$A_1$-CO—$R_1$—$R_2$—$R_3$—$R_4R_5$ (I)

wherein $R_1$ is $C_5$-$C_{10}$ alkylene;

$R_2$ is 2,3-oxiranylene, —CH═CH—$(CH_2)n$—, —$CH_2$—CH(X)—, —CH(X)—CH(X)—, —(CH═CH—CH(X))$_m$—, —$(CH_2$—CH(X)—$CH_2)_o$—, or —(CH(X)—CH(X)—$CH_2)_p$—, wherein X is hydrogen, halogen, hydroxy, amino, —O—CO—(CH$_2$)n—R$_{26}$, or —N$^+$(R$_{22}$R$_{23}$R$_{24}$), n is an integer from 0 to 7, and m, o, and p are integers from 1 to 3;

R$_3$ is C$_1$-C$_4$ alkylene, optionally substituted by halogen, amino or hydroxy;

R$_4$ is 2,3-oxiranylene, —CH(OH)—CH(R$_{25}$)—, —CH$_2$—CH(R$_{25}$)—, —CH(OH)—CH(X)—, and —CH(OH)—CH(O—CO—R$_6$—R$_7$—R$_8$—R$_9$—R$_{10}$)—, wherein X is as defined above in R$_2$;

R$_5$ is C$_1$-C$_{11}$ alkyl, and wherein the total sum of carbon atoms in the R$_1$—R$_2$—R$_3$—R$_4$—R$_5$ chain is at most 23;

A$_I$ is —NH—R$_0$, —O—R$_0$, —S—R$_0$, or —O—PO(OH)—OR$_0$;

R$_0$ is hydrogen, C$_1$-C$_6$ alkyl, or a residue selected from the groups (a)-(h) below, wherein A$_I$ can only be —O—R$_0$ when R$_0$ is one of the groups (f), (g), or (h):

(a) —R$_{11}$-Q$_1$-CO—R$_6$—R$_7$—R$_8$—R$_9$—R$_{10}$;
(b) —R$_{17}$-Q$_1$-CO—R$_{12}$—R$_{13}$—R$_{14}$—R$_{15}$—R$_{16}$;
(c) —R$_{19}$-Q$_1$-R$_{18}$;
(d) —R$_{19}$-Q$_1$-R$_{20}$-G;
(e) —CH$_2$—CH(OR$_{21}$)—CH$_2$—OR$_{21}$;

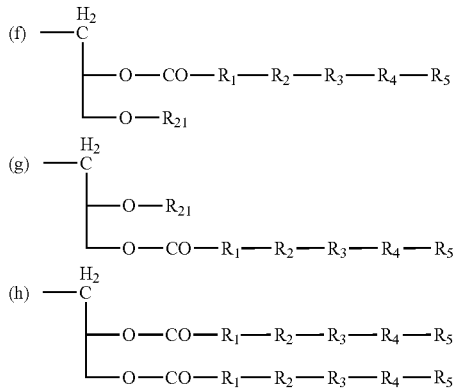

R$_6$ is C$_2$-C$_{10}$ alkylene;
R$_7$ is a covalent bond or as defined for R$_2$ above;
R$_8$ is a covalent bond or C$_1$-C$_4$ alkylene, preferably —CH$_2$—;
R$_9$ is a covalent bond, C$_1$-C$_{14}$ alkylene, or as defined for R$_4$ above;
R$_{10}$ is C$_1$-C$_{11}$ alkyl;
Q$_1$ is a covalent bond, —NH—, —O—, —S—, or —O—PO(OH)—O—;
R$_{11}$ is a spacer group selected from: C$_1$-C$_6$ alkylene, C$_6$-C$_{14}$ arylene, —(C$_6$-C$_{14}$ arylene)-R$_{28}$—(C$_6$-C$_{14}$ arylene)—(CH$_2$—CH$_2$—O)$_n$—CH$_2$—CH$_2$—, —(CH$_2$—CH$_2$—NH)$_m$—CH$_2$—CH$_2$—, —(CH$_2$—CH$_2$—S)$_o$—CH$_2$—CH$_2$—, —(CH(CH$_3$)—CH$_2$)$_p$—, —CH(CH$_3$)—(CH$_2$)$_q$—CH(CH$_3$)—, and —CH$_2$—CH(CH$_2$—O—R$_{21}$)—, wherein the C$_6$-C$_{14}$ arylene groups may be substituted each by R$_{27}$, and n, m, o, p and q are integers from 1 to 6;
R$_{12}$ is as defined for R$_6$ above;
R$_{13}$ is as defined for R$_7$ above;
R$_{14}$ is as defined for R$_8$ above;
R$_{15}$ is as defined for R$_9$ above;
R$_{16}$ is as defined for R$_{10}$ above;
R$_{17}$ is as defined for R$_{11}$ above or is a group —(CH$_2$)$_n$—N$^+$R$_{22}$R$_{23}$—(CH$_2$)$_m$— or —(CH$_2$)o-NR$_{21}$—(CH$_2$)$_p$—, wherein n, m, o and p are integers from 1 to 4;

G is hydrogen, or a residue of a protein, a polypeptide, an antibody, a polynucleotide, a DNA or a DNA fragment, RNA or RNA fragment, a polysaccharide, a plasmid, or of a chemotherapeutic agent ;

R$_{18}$ is hydrogen; —NR$_{22}$R$_{23}$; —N$^+$R$_{22}$R$_{23}$R$_{24}$; —N=CH—(C$_6$-C$_{14}$ arylene) —N$^+$R$_{22}$R$_{23}$R$_{24}$; C$_1$-C$_8$ alkyl [optionally substituted by C$_6$-C$_{14}$ aryl or by R$_{29}$]; C$_6$-C$_{14}$ aryl ; C$_4$-C$_9$ heteroaryl containing one or more heteroatoms selected from N, O, and S [said C$_6$-C$_{14}$ aryl and C$_4$-C$_9$ heteroaryl being optionally substituted by C$_1$-C$_6$ alkyl, —(CH$_2$)$_2$—NH$_2$, —COOH, —SH, —SO$_3$H, —O—SO$_2$H , or —O—PO(OH)$_2$]; —(CH$_2$)$_m$—(C$_6$-C$_{14}$ arylene)—R$_{29}$; —(CH$_2$)$_o$—(C$_6$-C$_{14}$ arylene)-(CH$_2$)$_p$—R$_{29}$; —O—PO(OH)—O—CH$_2$—CH$_2$—N(CH$_3$)$_3$$^+$; —O—PO(OH)—O—CH$_2$—CH$_2$—NH$_2$; or —O—PO(OH)—O—CH$_2$—CH(COO$^-$)—NH$_3$$^+$; wherein n is an integer from 1 to 6, m and o are integers from 1 to 20, and p is an integer from 0 to 20;

R$_{19}$ is as defined for R$_{11}$ above, or is a spacer group selected from —CH$_2$—(C$_6$-C$_{14}$ arylene)-R$_{28}$-(C$_6$-C$_{14}$ arylene)-; bi(C$_6$-C$_{14}$)arylene; bi(C$_4$-C$_9$)heteroarylene; and C$_4$-C$_9$ heteroarylene, wherein said bi(C$_4$-C$_9$)heteroarylene and C$_4$-C$_9$ heteroarylene each contain one or more heteroatoms selected from N, O, and S, and are optionally substituted by —OH, —COOH, —SH, —SO$_3$H, —O—SO$_2$H, and —O—PO(OH)$_2$;

R$_{20}$ is C$_1$-C$_8$ alkylene, optionally substituted by C$_6$-C$_{14}$ aryl or R$_{29}$; C$_6$-C$_{14}$ arylene; or C$_4$-C$_9$ heteroarylene containing one or more heteroatoms selected from N, O, and S, said C$_6$-C$_{14}$ arylene and C$_4$-C$_9$ heteroarylene being optionally substituted by C$_1$-C$_6$ alkyl, —(CH$_2$)$_n$—NH$_2$, —COOH, —SH, —SO$_3$H, —O—SO$_2$H, or —O—PO(OH)$_2$;

R$_{21}$ is hydrogen, —O—PO(OH)$_2$, —O—PO(OH)—O—CH$_2$—CH$_2$—X, wherein X is as defined for R$_2$, or —O—PO(OH)—O—CH$_2$—CH(COO$^-$)—NH$_3$$^+$;

R$_{22}$, R$_{23}$, and R$_{24}$, independently of each other, are each hydrogen; C$_1$-C$_{20}$ alkyl or C$_6$-C$_{14}$ aryl, said C$_1$-C$_{20}$ alkyl and C$_6$-C$_{14}$ aryl being optionally substituted by halogen, C$_6$-C$_{14}$ aryl, —OH, —NH$_2$—, —SH, —COOH, —SO$_3$H, —O—SO$_2$H, —O—PO(OH)$_2$, —O—PO(OH)—O—(CH$_2$)$_2$ —NH$_3$$^+$, or —O—PO(OH)—O—CH$_2$—CH(COO$^-$)—NH$_3$$^+$; or R$_{24}$ is absent and R$_{22}$ and R$_{23}$ together with the N atom to which they are attached form an aromatic or non—aromatic heterocyclic ring optionally charged in the N atom, said heterocyclic ring optionally containing a further heteroatom selected from N, 0, and S, and further being optionally substituted by —NH$_2$, —COOH, —CH=N—OH, —OH, —SO$_3$H, and —O—PO(OH)$_2$;

R$_{25}$ is N$_3$; —O—CO—(C$_2$-C$_6$ alkenyl), —O—CO—(CH$_2$)$_n$—R$_{26}$; —(CH$_2$)$_m$—O—SO$_2$H; —O—SO$_2$H; —(CH$_2$)$_o$—COOH; —(CH$_2$)$_p$—O—PO(OH)$_2$; —O—PO(OH)$_2$; —O—PO(OH)—O—(CH$_2$)q-N$^+$R$_{22}$R$_{23}$R$_{24}$; —N$^+$R$_{22}$R$_{23}$R$_{24}$; —NR$_{22}$R$_{23}$; —N$^+$(CH$_3$)$_2$R$_{30}$; —SR$_{31}$; —R$_{32}$—(C$_6$-C$_{14}$ arylene)-R$_{26}$; or —R$_{32}$—(C$_6$-C$_{14}$ arylene)-(CH$_2$)r-R$_{26}$, wherein n, m, o, p, and q are integers from 1 to 14, and r is an integer from 1 to 3;

R$_{26}$ is halogen; —NR$_{22}$R$_{23}$; —N$^+$R$_{22}$R$_{23}$R$_{24}$; —COOH ; —SO$_3$H; —O—PO(OH)$_2$; —NH—(CH$_2$)n-SO$_3$H; —NH—(CH$_2$)m-COOH ; —NH—(CH$_2$)o-O—PO(OH)$_2$; —O—PO(OH)—NH—PO(OH)—O—; —N$^+$(CH$_3$)$_2$—R$_{30}$; —O—PO(OH) —O—(CH$_2$)$_2$—N$^+$R$_{22}$R$_{23}$R$_{24}$; —O—PO(OH)—O—(CH$_2$)$_2$—NH$_3$$^+$; and —O—PO(OH)—O—CH$_2$—CH(COO$^-$)—NH$_3$$^+$; wherein n, m, and o are integers from 1 to 3;

R$_{27}$ is —(CH$_2$)$_n$—NR$_{22}$R$_{23}$—, —NH—(CH$_2$)$_o$—SO$_3$H, —NH—(CH$_2$)$_o$—COOH, —NH—(CH$_2$)$_p$—O—PO(OH)$_2$, —NH—PO(OH)$_2$, —NH—(CH$_3$)$_2$—R$_{30}$, —NH—(CH$_2$)n-O—PO(OH)—O—(CH$_2$)$_2$—NH$_3$$^+$, or —NH—(CH$_2$)$_q$—O—PO(OH)—O—CH$_2$—CH(COO$^-$)—NH$_3$$^+$, wherein n, m, o, p, and q are integers from 0 to 3;

R$_{28}$ is C$_1$-C$_4$ alkylene, —C(CH$_3$)$_2$—, —O—, —NH—, —S—, or —SO$_2$;

$R_{29}$ is —COOH, —$NR_{22}R_{23}$, —$(CH_2)n-N^+R_{22}R_{23}R_{24}$—, wherein n is an integer from 0 to 3; and as defined for $R_{27}$ above;

$R_{30}$ is —$CH_2$—CH=$CH_2$, —CO—CH=$CH_2$, —CO—C($CH_3$)=$CH_2$, —$(CH_2)_n$—$N^+R_{22}R_{23}R_{24}$, —$(CH_2)$m—NH—$(CH_2)_o$—$SO_3H$, —$(CH_2)_p$—NH—$(CH_2)_q$—COOH, —$(CH_2)_r$—NH—$(CH_2)$s-O—PO(OH)$_2$, —PO(OH)$_2$, or —O—PO(OH)—O—$(CH_2)_2$—$N^+R_{22}R_{23}R_{24}$, wherein n, m, p, q, r, and s are integers from 0 to 3;

$R_{31}$ is hydrogen, $C_2$-$C_6$ alkenyl with a terminal double bond, —CO—CH=$CH_2$, or —CO—C($CH_3$)=CH—$NR_{22}R_{23}$;

$R_{32}$ is —NH—, —O—, —S—, —$CH_2$—NH—, —$CH_2$—S—, or —$CH_2$—O—;

and salts thereof, but excluding the compounds vernolic acid, trivernol in , N, N' —ethylene bis (vernolamide) , N, N'-propylene bis (vernolamide) , and 1,2-bis (2-aminoethoxy) ethane N,N' bis (vernolamide).

In one embodiment, the amphiphilic derivative or a precursor thereof has the formula Ia:

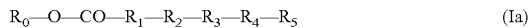

wherein $R_1$ is C5-C10 alkylene; $R_2$ is —CH=CH—$(CH_2)$n-, —$CH_2$—CH(X)—, —CH(X)—CH(X)—, —(CH=CH—CH(X))$_m$—, —$(CH_2$—CH(X)—$CH_2)_o$—, or —(CH(X)—CH(X)—$CH_2)_p$—, wherein X is hydrogen, halogen, amino, or —$N^+(R_{22}R_{23}R_{24})$, n is an integer from 0 to 7, and m, o, and p are integers from 1 to 3; $R_3$ is $C_1$-$C_4$ alkylene, optionally substituted by halogen, amino or hydroxy; $R_4$ is 2,3-oxiranylene, —CH(OH)—CH($R_{25}$)—, —$CH_2$—CH($R_{25}$)—, —CH(OH)—CH(X)—, or —CH(OH)—CH(O—CO—$R_6$—$R_7$—$R_8$—$R_9$—$R_{10}$)—, wherein X is as defined above in $R_2$; $R_5$ is $C_1$-$C_{11}$ alkyl, wherein the total sum of carbon atoms in the $R_1$—$R_2$—$R_3$—$R_4$—$R_5$ chain is at most 23; $R_0$ is hydrogen or $C_1$-$C_6$ alkyl; and all other groups are as defined before.

Among these compounds are derivatives of vernolic acid and from esters thereof, including those compounds where the epoxy group has been opened such as compounds of the formula Ib:

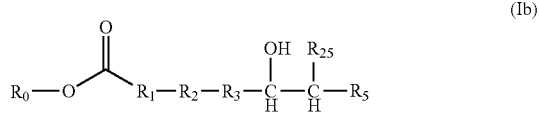

wherein R25 is, for example, a quaternary ammonium group —N+R22R23R24, e.g. —$N^+(CH_3)_3$, represented particularly by the derivative herein designated Derivative 1.

In another embodiment, in the derivative of formula Ib, $R_{25}$ may be —O—CO—$(CH_2)_n$—$R_{26}$, wherein n is an integer from 1 to 14, such as a compound of the formula Ic:

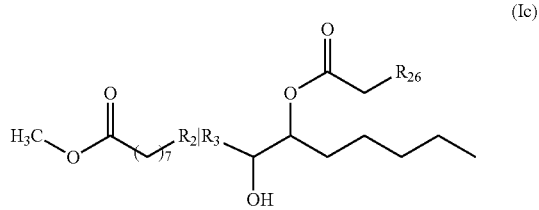

wherein $R_2$ is —CH=CH—$(CH_2)_n$— or —$CH_2$—CH(X)—, wherein X is hydrogen, halogen, or amino, and n is an integer from 0 to 7;

$R_3$ is —$CH_2$— or —CH(Br)—; and $R_{26}$ is halogen; —$NR_{22}R_{23}$; —$N^+R_{22}R_{23}R_{24}$; —COOH; —$SO_3H$; —O—PO(OH)$_2$; —NH—$(CH_2)_n$—$SO_3H$; —NH—$(CH_2)_m$—COOH; —NH—$(CH_2)_o$—O—PO(OH)$_2$; —O—PO(OH)—NH—PO(OH)—O—; —$N^+(CH_3)_2$—$R_{30}$; —O—PO(OH)—O—$(CH_2)_2$—$N^+R_{22}R_{23}R_{24}$; —O—PO(OH)—O—$(CH_2)_2$—$NH_3^+$; and —O—PO(OH)—O—$CH_2$—CH($COO^-$)—$NH_3^+$; wherein n, m, and o are integers from 1 to 3; and wherein $R_{22}$, $R_{23}$, $R_{24}$, and $R_{30}$ are as defined before.

Examples of said derivatives of formula Ic are illustrated by the compounds herein designated Derivatives 2, 3, 4, 5 and 16, each carrying a different substituent $R_{26}$ at the acetoxy group —O—CO—$CH_2$—$CHR_{26}$.

In a further embodiment, the amphiphilic derivative or a precursor thereof of the invention is of the formula Id:

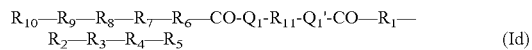

wherein $Q_1$ and $Q_1'$, the same or different, represent —NH—, —O—, —S—, or —O—PO(OH)—O—; $R_{11}$ is the spacer group $C_1$-$C_6$ alkylene or —$(CH_2$—$CH_2$—NH)$_m$—$CH_2$—$CH_2$—; $R_4$ and $R_9$, the same or different, are each 2,3-oxiranylene or —CH(OH)—CH($R_{25}$)—, wherein m is an integer from 1 to 6, and $R_1$, $R_2$, $R_3$, $R_5$, $R_6$, $R_7$, $R_8$, $R_{10}$, and $R_{25}$ are as defined before.

In one preferred embodiment, in the amphiphilic derivative of formula Id, $Q_1$ and $Q_1'$ are the same and are both —O—, and $R_{25}$ is —$N^+R_{22}R_{23}R_{24}$ or —$NR_{22}R_{23}$, as represented by the derivatives herein designated Derivative 8 and Derivative 9. In another preferred embodiment, in the amphiphilic derivative of formula Id, $Q_1$ and $Q_1'$ are the same and are both —NH—, and $R_{25}$ is —O—$SO_2H$ (or, more exactly, the Na salt thereof O—$SO_2Na$) as represented by the derivative herein designated Derivative 11, or $R_{25}$ is —O—CO—$CH_2$—$R_{26}$, wherein $R_{26}$ is —$N^+R_{22}R_{23}R_{24}$, as represented by the derivatives herein designated Derivative 10 and Derivative 12.

In still a further embodiment, in the amphiphilic derivative of the formula Ic, $R_4$ and $R_9$ is each 2,3-oxiranylene and $R_{11}$ is —$(CH_2$—$CH_2$—NH)$_m$—$CH_2$—$CH_2$—, wherein m is an integer from 1 to 6, as exemplified by Derivative 15.

In yet another embodiment, the amphiphilic derivative is of the formula If:

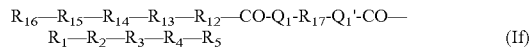

wherein $Q_1$ and $Q_1'$, the same or different, represent —NH—, —O—, —S—, or —O—PO(OH)—O—;

$R_{17}$ is —$(CH_2)_n$—$N^+R_{22}R_{23}$—$(CH_2)_m$— or —$(CH_2)_o$—$NR_{22}$—$(CH_2)_p$—, wherein n, m, o and p are integers from 1 to 4; $C_1$-$C_6$ alkylene, $C_6$-$C_{14}$ arylene, —($C_6$-$C_{14}$ arylene)-$R_{28}$-($C_6$-$C_{14}$ arylene)-, —$(CH_2$—$CH_2$—O)n-$CH_2$—$CH_2$—, —$(CH_2$—$CH_2$—NH)$_m$—$CH_2CH_2$, —$(CH_2$—$CH_2$—S)$_o$—$CH_2$—$CH_2$—, —(CH($CH_3$)—$CH_2)_p$—, —CH($CH_3$)—$(CH_2)_q$—CH($CH_3$)—, and —$CH_2$—CH($CH_2$—O—$R_{21}$)—, wherein the $C_6$-$C_{14}$ arylene groups may be substituted each by $R_{27}$, and n, m, o, p and q are integers from 1 to 6;

$R_4$ and $R_{15}$ independently of each other are 2,3-oxiranylene or —CH(OH)—CH($R_{25}$)—;

and $R_1$, $R_2$, $R_3$, $R_5$, $R_6$, $R_{12}$, $R_{13}$, $R_{14}$, $R_{16}$, $R_{21}$, $R_{22}$, $R_{23}$, $R_{25}$ and $R_{28}$ as defined before.

According to this embodiment, there is provided, for example, a compound of the formula Ig:

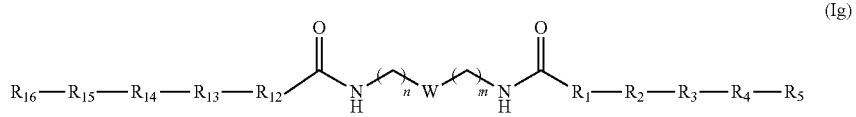

wherein W is $-N^+R_{22}R_{23}$ or $-NR_{22}$, n and m are integers from 1 to 4; and $R_4$ and $R_{15}$ are each 2,3-oxiranylene or $-CH(OH)-CH(R_{25})-$. Examples of such compounds are the Derivatives 13 and 14.

In still a further embodiment, the amphiphilic derivative is of the formula Ih:

$$R_{18}\text{-}Q_1\text{-}R_{19}\text{-}Q_1'\text{-}CO-R_1-R_2-R_3-R_4-R_5 \quad (Ih)$$

wherein $Q_1$ and $Q_1'$, the same or different, represent each a covalent bond, $-NH-$, $-O-$, $-S-$, or $-O-PO(OH)O-$;

$R_4$ is 2,3-oxiranylene or $-CH(OH)-CH(R_{25})-$;

$R_{18}$ is hydrogen, $-NR_{22}R_{23}$, $-N^+R_{22}R_{23}R_{24}$, $-N=CH-(C_6\text{-}C_{14}$ arylene$)-N^+R_{22}R_{23}R_4$, $C_1\text{-}C_8$ alkyl, optionally substituted by $C_6\text{-}C_{14}$ aryl or $R_{29}$; $C_6\text{-}C_{14}$ aryl; $C_4\text{-}C_9$ heteroaryl containing one or more heteroatoms selected from N, O, and S, said $C_6\text{-}C_{14}$ aryl and $C_4\text{-}C_9$ heteroaryl being optionally substituted by $C_1\text{-}C_6$ alkyl, $-(CH_2)_n-NH_2$, $-COOH$, $-SH$, $-SO_3H$, $-O-SO_2H$, or $-O-PO(OH)_2$; $-(CH_2)_m-(C_6\text{-}C_{14}$ arylene$)-R_{29}$, $-(CH_2)_o-(C_6\text{-}C_{14}$ arylene$)-(CH_2)p\text{-}R_{29}$, $-O-PO(OH)-O-CH_2-CH_2-N(CH_3)_3^+$, $-O-PO(OH)-O-CH_2-CH_2-NH_2$, or $-O-PO(OH)-O-CH_2-CH(COO^-)-NH_3^+$; wherein n is an integer from 1 to 6, m and o are integers from 1 to 20, and p is an integer from 0 to 20;

$R_{19}$ is $C_1\text{-}C_6$ alkylene, $-CH_2-(C_6\text{-}C_{14}$ arylene$)-R_{28}-(C_6\text{-}C_{14}$ arylene$)-$;

and $R_1$, $R_2$, $R_3$, $R_5$, $R_{22}$, $R_{23}$, $R_{24}$, $R_{25}$, and $R_{29}$ are as defined before.

In one embodiment, $Q_1$ and $Q_1'$ are both the same and are $-NH-$, $R_{18}$ is hydrogen and $R_{19}$ is $C_1\text{-}C_6$ alkylene as illustrated by the Derivatives 6, 16, 17, 18, and 19. In another embodiment, the spacer $R_{19}$ is composed of 2 or three benzene rings separated by a group $R_{28}$, as exemplified by the Derivatives 20 and 21:

In yet still a further embodiment, the amphiphilic derivative is of the formula Ii:

$$G\text{-}R_{20}\text{-}Q_1\text{-}R_{19}\text{-}Q_1'\text{-}CO-R_1-R_2-R_3-R_4-R_5 \quad (Ii)$$

wherein $Q_1$ and $Q_1'$, the same or different, represent a covalent bond, $-NH-$, $-O-$, $-S-$, or $-O-PO(OH)O-$;

$R_4$ is 2,3-oxiranylene or $-CH(OH)-CH(R_{25})-$;

$R_{19}$ is $C_1\text{-}C_6$ alkylene, $-CH_2-(C_6\text{-}C_{14}$ arylene$)-R_{28}\text{-}(C_6\text{-}C_{14}$ arylene$)-$;

$R_{20}$ is $C_1\text{-}C_8$ alkylene, optionally substituted by $C_6\text{-}C_{14}$ aryl or $R_{29}$; $C_6\text{-}C_{14}$ arylene; or $C_4\text{-}C_9$ heteroarylene containing one or more heteroatom selected from N, O, and S, said $C_6\text{-}C_{14}$ arylene and $C_4\text{-}C_9$ heteroarylene being optionally substituted by $C_1\text{-}C_6$ alkyl, $-(CH_2)_n-NH_2$, $-COOH$, $-SH$, $-SO_3H$, $-O-SO_2H$, or $-O-PO(OH)_2$;

G is hydrogen, or a residue of a protein, a polypeptide, an antibody, a polynucleotide, a DNA or a DNA fragment, RNA or RNA fragment, a polysaccharide, a plasmid, and or of a chemotherapeutic agent;

and $R_1$, $R_2$, $R_3$, $R_5$, $R_{25}$, $R_{28}$, and $R_{29}$ are as defined before.

These derivatives of formula (Ii) may anchor a pendant G into the vesicle membrane and give the vesicle special targeting properties or act as identification markers. For example, derivatives which contain both a group (the fatty acid chain without ionic head group) which anchors itself in the vesicle membrane and the pendant (usually ionic or polar) which can be a marker or a ligand such as antibody, a fluorescent molecule, a plasmid, or a complexant such as a polyamine which is protonated at physiological pH and can bind DNA fragments.

In yet a further embodiment, the amphiphilic derivative is a triglyceride of the formula Ij, Ik, Il and Im as follows:

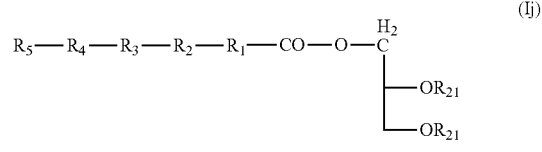

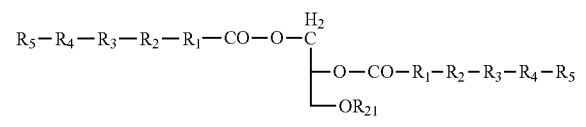

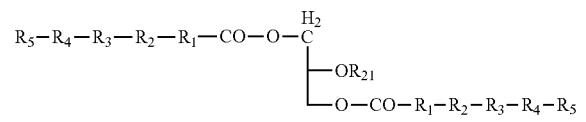

wherein $R_{21}$ is hydrogen, $-O-PO(OH)_2$, $-O-PO(OH)-O-CH_2-CH_2-X$, or $-O-PO(OH)-O-CH_2-CH(COO^-)-NH_3^+$; and $R_1$, $R_2$, $R_3$, $R_4$, $R_5$ and X are as defined before.

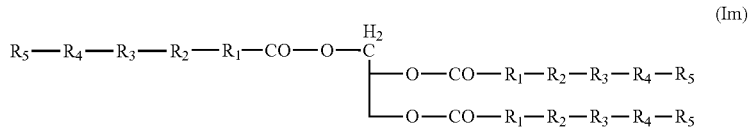

wherein $R_1$ is $C_5$-$C_{10}$ alkylene;

$R_2$ is 2,3-oxiranylene, —CH=CH—(CH$_2$)$_n$—, —CH$_2$—CH(X)—, —CH(X)—CH(X')—, —(CH=CH—CH(X))$_m$—, —(CH)—CH(X)—CH$_2$)$_o$—, or —(CH(X)—CH(X')—CH$_2$)$_p$—, wherein X and X', same or different, are hydrogen, halogen, hydroxy, amino, —O—CO—(CH$_2$)$_n$—R$_{26}$, or —N$^+$(R$_{22}$R$_{23}$R$_{24}$), n is an integer from 0 to 7, and m, o, and p are integers from 1 to 3;

$R_3$ is $C_1$-$C_4$ alkylene, optionally substituted by halogen, amino or hydroxy;

$R_4$ is 2,3-oxiranylene, —CH(OH)—CH(R$_{25}$)—, —CH$_2$—CH(R$_{25}$)—, —CH(OH)—CH(X)—, and —CH(OH)—CH(O—CO—R$_6$—R$_7$—R$_8$—R$_9$—R$_{10}$)—;

$R_5$ is $C_1$-$C_{11}$ alkyl, and wherein the total sum of carbon atoms in the $R_1$—$R_2$—$R_3$—$R_4$—$R_5$ chain is at most 23;

X is hydrogen, halogen, hydroxy, amino, or —N$^+$(R$_{22}$R$_{23}$R$_{24}$);

wherein $R_6$, $R_7$, $R_8$, $R_9$, $R_{10}$, $R_{25}$, and $R_{26}$ are as defined before.

Examples of such triglycerides are the Derivatives 24, 25, 26, 27, 28 and 30.

The present invention further includes the novel precursors of the amphiphilic 10 derivatives of the invention, particularly the compounds herein designated Precursors 1, 2, 3, 5, 7, 8, 9, 10, 12, 13, 14, 15, 16, 17, and 18.

As used herein the term "hydrocarbyl" refers to a radical derived from a hydrocarbon such as from an alkane, alkene, cycloalkane and aromatic hydrocarbon. Thus, hydrocarbyl includes the radicals alkyl, alkenyl, cycloalkyl and aryl, all as detailed herein. The term "optionally substituted hydrocarbyl" when used for $R_0$ refers to such a hydrocarbyl that may be substituted by any of the multiple substitutions as detailed for $R_0$ in other parts of the description or of the claims. The term "$C_1$-$C_{20}$ alkyl" typically refers to a straight or branched alkyl radical having 1-20 carbon atoms and includes for example methyl, ethyl, n-propyl, iso-propyl, n-butyl, iso-butyl, tert-butyl, n-heptyl, 2,2-dimethylpropyl, n-hexyl, n-dodecyl, n-octadecyl and the like. The term "$C_1$-$C_{20}$ alkylene" refers to straight or branched alkylene group having 1-20 carbon atoms and includes for example methylene, ethylene, propylene, butylene and the like. The term "$C_2$-$C_6$ alkenyl" refers to straight or branched hydrocarbon radicals having 2-6 carbon atoms and at least one terminal double bond and includes for example vinyl, prop-2-en-1-yl, but-3-en-1-yl, pent-4-en-1-yl, and hex-5-en-1-yl. The term "$C_2$-$C_6$" alkenylene refers to straight or branched hydrocarbon radicals having 2-6 carbon atoms and at least one terminal double bond and includes for example vinylene, prop-2-en-1-ylene, but-3-en-1-ylene, pent-4-en-1-ylene, and hex-5-en-1-ylene.

The term "$C_6$-$C_{14}$ aryl" refers to an aromatic carbocyclic group having 6 to 14 carbon atoms consisting of a single ring or multiple condensed rings such as phenyl, naphthyl, and phenanthryl optionally substituted by $C_1$-$C_6$ alkyl. The term "heteroaryl" refers to a monocyclic, bicyclic or tricyclic fused-ring heteroaromatic group. Particular examples are pyridyl, pyrrolyl, furyl, thienyl, imidazolyl, oxazolyl, quinolinyl, thiazolyl, pyrazolyl, 1,3,4-triazinyl, 1,2,3-triazinyl, benzofuryl, isobenzofuryl, indolyl, imidazo[1,2-a]pyridyl, benzimidazolyl, benzthiazolyl and benzoxazolyl. The term "bi($C_6$-$C_{14}$) arylene" refers to two unsaturated aromatic carbocyclic groups connected to each other directly. Particular examples are biphenylene, binaphthylene and bianthrylene. The term "bi($C_4$-$C_{14}$) heteroarylene" refers to two monocyclic, bicyclic or tricyclic fused-ring heteroaromatic groups connected to each other directly. Particular examples are bipyridylene, bifurylene, bipyridylene, and biimidazolylene. The term "halogen" refers to fluoro, chloro, bromo or iodo.

The invention further encompasses the salts of the amphiphilic derivatives. Examples of salts include, but are not limited to acid addition salts formed with inorganic acids (hydrochloric acid, hydrobronic acid, sulfuric acid, phosphoric acid, nitric acid and the like) and salts formed with organic acids such as acetic acid, oxalic acid, tartaric acid, succinic acid, maleic acid, fumaric acid, maleic acid, ascorbic acid, benzoic acid, and the like. Said compounds can also be quaternary salts known by a person skilled in the art, which specifically include the quaternary salt of the formula —NRR'R"+Z' wherein R, R', R" is independently hydrogen, alkyl or benzyl and Z is a counterion, including chloride, bromide, iodide, O-alkyl, toluenesulfonate, methylsulfonate, sulfonate, phosphate, or carboxylate.

Base addition salts are formed with metals or amines such as alkali and alkaline earth metals or organic amines. Examples of metals used as cations are sodium, potassium, magnesium, calcium, and the like. Examples of suitable amines are N,N'-dibenzylethylenedialine, chloroprocaine, choline, diethanolamine, ethylenediamine, and N-methylglucanine.

Preparation of Vernonia Oil Derivatives of the Invention

Trivernolin, vernolic acid triglyceride, is the main component of vernonia oil. Derivatization of trivernolin may be achieved by reacting pure trivernolin extracted from the vernonia oil mixture or by reacting the multi-component vernonia oil mixture followed by isolation of the products and purification of the functionalized trivernolin. In the Examples given in the present invention, preparation of the amphiphilic derivatives of trivernolin is carried on the vernonia oil mixture without initial separation of trivernolin, or unless specified otherwise. Trivernolin was separated from vernonia oil by column chromatography using n-hexane and increasing amounts of diethyl ether as the eluent as previously described [Grinberg et al., 1994]. The TLC in n-hexane and diethyl ether (1.5:1 v/v) gave an $R_f$ of 0.4 for trivernolin. The amount of epoxy groups calculated for trivernolin was 13.6%; the amount found was 13.3%.

The Derivatives 1-29 and Precursors 1-18 of the invention can be prepared as illustrated in Schemes 1 to 20 in the Appendix herein. The syntheses involve initial construction of new vernonia oil derivatives or direct functionalization of the natural derivatives by organic synthesis manipulations such as, but not limiting to, epoxide ring opening, amidation, transesterification, reduction, amination, amino group quaternization, and the like. The general procedures used in the present invention are:

(a) Oxiranyl ring opening: The epoxy group characteristic of the natural vernonia oil derivatives is opened by the addition of reagents such as carboxylic acids or organic or inorganic nucleophiles. Such ring opening results in a mixture of two products in which the new group is introduced at either of the two carbon atoms of the epoxide moiety. This provides β-substituted alcohols (positions 1-2) in which the substitution position most remote from the CO group of the main aliphatic chain of the vernonia oil derivative is arbitrarily assigned as position 1. The neighboring substituted carbon position is designated position 2, as is shown below. For simplicity purposes only, the Derivatives and Precursors shown in Schemes 1-20 indicate structures with the hydroxy group always at position 2 but the Derivatives and Precursors wherein the hydroxy is at position 1 are also encompassed by the invention. Thus, a radical of the formula —CH(OH)—CH(R)— refers to the substitution of —OH at either the carbon closer to the CO group, designated position 2, as in Case 1 below, or to the carbon at position 1, as shown in Case 2 below.

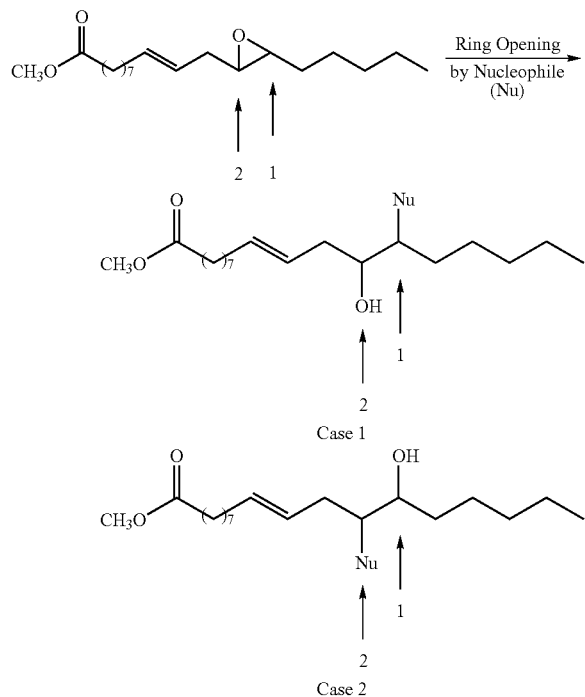

Case 1

Case 2

(b) Formation of β-azido derivatives: The β-azido derivatives are prepared by reacting the epoxy vernonia derivatives with sodium azide under three different experimental conditions. Method (i): an ethanolic solution of the epoxy derivative is reacted with sodium azide and ammonium chloride at refluxing temperatures for two days; Method (ii): a methanolic solution of the epoxy derivative is reacted with sodium azide and triethyl amine at refluxing temperatures for two days; and Method (iii): a methanolic solution of the epoxy derivative is reacted with sodium azide and ammonium chloride at refluxing temperatures for two days.

(c) Reduction of β-azido derivatives to amines: Reduction of the azido derivatives to the amino compounds is achieved in three different ways: Method (i): reduction with sodium borohydride in the presence of hexadecyltrimethyl ammonium bromide and CoCl; Method (ii): reduction with sodium borohydride in the presence of $CoCl_2$ and in iso-propanol at refluxing temperatures; and Method (c): catalytic hydrogenation in methanol with 10% Pd—C, under atmospheric pressure and at room temperature. The catalytic hydrogenation was successful in the azido-to-amino transformation but also resulted in some reduction of the double bond.

(d) Quaternization of free amino groups: A mixture of the amino precursor and the alkyl halide is heated at the refluxing temperature for several hours or until all of the free amino compound was reacted.

(e) Amination of haloesters: A mixture of the halo precursor and the secondary or tertiary amine in an appropriate solvent is refluxed until all of the halo precursor was consumed.

(f) Acylation of free amino compounds with vernonia oil esters. Mono-amidoamines or diamide derivatives were prepared by heating a solution containing the ester, the mono or poly-amine and a base, until all of the ester was consumed.

Thus, Derivative 1 was prepared in two steps from methyl vernolate according to Scheme 1: (i) Addition of sodium azide to methyl vernolate formed the β-azido alcohol, designated Precursor 1, and (ii) Reduction of the azido group by various methods, gave the β-amino alcohol designated Derivative 1.

Derivatives 2, 3, 4 and 5 were prepared from the β-(β-halo acetoxy) alcohol, Precursor 2, which was prepared from methyl vernolate as shown in Scheme 2. Thus, Derivatives 2, 3, 4 and 5 were prepared as shown in Schemes 2-5 by amination of the haloacetoxy group of Precursor 2 with the appropriate tertiary or secondary amine and formation of the ammonium Derivatives 2, 3, and 5 or of the tertiary amino Derivative 4.

Scheme 5 also depicts the preparation of Derivatives 6 and 7. Derivative 6 was prepared by acylating ethylenediamine with Derivative 5. Then, Derivative 6 was further acylated at the free amino group by Derivative 2, affording the asymmetric amphiphilic Derivative 7.

Derivatives 8 and 9 were prepared in 4 steps from trivernolin. First, trivernolin was reacted with 1,4-butanediol, as shown in Scheme 6, to afford the transetserification product Precursor 3. Next, Precursor 3 was reacted with sodium azide and the resulting β-azido alcohol was selectively reduced to affect the azido-to-amino transformation. The β-amino alcohol, Derivative 8, was then allylated stepwise with iodomethane and bromododecane to afford the bis-dimethyldodecyl ammonium salt, Derivative 9.

Trivernolin and methyl vernolate were also used as starting materials for the preparations of diamido derivatives of vernonia oil, by reaction with ethylene diamine and production of Precursor 4, as depicted in Scheme 7. Derivative 10 was prepared in two steps, as shown in Scheme 8, from the diamido Precursor 4 of Scheme 7. The bis β-hydroxy sulfinic acid Derivative 11 was prepared by epoxide ring opening of Precursor 4 with sodium bisulfite, as shown in Scheme 9.

Homologues of Precursor 4, such as Precursors 6 and 7 of Scheme 10 and Precursors 8 and 9 of Scheme 11, were prepared also from methyl vernolate and the appropriate alkylenediamine. Precursor 6 was utilized as the starting material in the two-step synthesis of the amphiphilic Derivative 12, as shown in Scheme 10.

Amphiphilic Derivatives 13, 14 and 15 were prepared as shown in Schemes 12 and 13. Acylation of dietlhylenetriamine with methyl vernolate gave Precursor 10, which was alkylated with iodomethane to give Derivative 13. The amphiphilic Derivative 13 was then further modified by the addition of acrylic acid to the oxiranyl groups and the formation of bis β-ester alcohol Derivative 14. Similarly to the preparation of Precursor 10, Derivative was prepared from trivernolin and triethylene tetraamine.

Amphiphilic Derivatives 16-19 were prepared from methyl vernolate and the appropriate alkylene diamine as depicted in Scheme 14. Methyl vernolate was also used as an acylating agent of p-aminophenyl-p-aminomethylphenylsulfone, thus providing Derivative 20, as shown in Scheme 15. Derivative 21 was formed the reaction of Derivative 20 with (p-formylphenyl) trimethyl ammonium bromide at the refluxing temperature.

The liposome precursor Derivative 22 was prepared in three steps from the triglyceride Precursor 11 according to the procedure of Hirt and Berchtold [Hirt and Berchtold, 1958]. The phosphocholine moiety was introduced into the triglyceride Precursor 11 by phosphorylation with (2-bromoethyl) phosphodichloridate, followed by hydrolysis, thus obtaining Precursor 12. Precursor 12 was then reacted with trimethyl amine to give Derivative 22, as depicted in Scheme 16.

Trivernolin was derivatized as depicted in Schemes 17 and 18. Epoxide ring opening with haloacetic acid or azide gave Precursor 13 or Precursor 14, respectively. The tris-haloacetoxy Precursor 13 was transformed to the ammonium derivatives with tertiary amines as dimethyldodecylamine to give Derivative 23, with dimethyloctadecylamine to give Derivative 24, and with trimethylamine to give Derivative 25, as shown in Scheme 17.

Scheme 18 depicts the preparation of Derivative 27, which was prepared in three steps from trivernolin, according to a procedure similar to that utilized for the synthesis of Derivative 8. Derivative 26 was alkylated stepwise or in one step with excess iodo methane, as shown in Scheme 18.

Methyl vernolate was selectively brominated at the allylic position situated between the epoxy and the double bond by N-bromo succinimide. The bromo derivative, Precursor 15, was then treated with chloroacetic acid, providing the amphiphilic Precursor 16 wherein positions 1-2-3 are substituted. The haloacetoxy group was next aminated with a tertiary amine, thus obtaining Derivative 28.

Epoxidation of castor oil was achieved in the presence of meta-chloroperbenzoic acid, as shown in Scheme 20. The tris epoxy Precursor 17 was next treated with chloroacetic acid, providing Precursor 18 in which the positions occupied by substitutions are 1-34. Amination of Precursor 18 with triethyl amine gave Derivative 29.

Although Schemes 1-20 indicate exact structures, the methods apply widely to analogous compounds of Formula I, given appropriate consideration to protection and deprotection of reactive functional groups by methods standard to the art of Organic Chemistry. For example, in order to prevent unwanted side reactions, hydroxy groups generally need to be converted to ethers or esters during chemical reactions at other sites in the molecule. The hydroxy protecting group is readily removed to provide the free hydroxy group. Amino groups and carboxylic acid groups are similarly derivatized to protect then against unwanted side reactions. Typical protecting groups, and methods for attaching and cleaving them, are described fully by Greene and Wuts in Protective Groups in Organic Synthesis, John Wiley and Sons, New-York ($2^{nd}$ Ed, 1991) and McOmie, Protective Groups in Organic Chemistry, Plenum Press, New-York, 1973.

For the preparation of other compounds of Formula I, similar procedures known to those of skill in the art may be used.

The acid addition salts of the basic derivatives of the invention are prepared by contacting the free base form with a sufficient amount of the desired acid to produce the salt in the conventional maimer and without affecting other sensitive groups that may be present. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

The base addition salts of the acidic compounds are prepared by contacting the free acid form with a sufficient amount of the desired base to produce the salt in the conventional manner and without affecting other sensitive groups that may be present. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free base for purposes of the present invention.

Applications of the Amphiphilic Derivatives of the Invention and of the Products Thereof The amphiphilic derivatives of the invention can be used to form vesicles and liposomes. The vesicles are useful for the encapsulation of biologically active materials and delivering them to target sites. Particular pharmaceutical agents that can be delivered by vesicles and by stable micelles made from the amphiphilic derivatives, are chemotherapeutic drugs, antibiotics, antiviral agents, fungicides, cytokines, anti-inflammatory agents, neurotransmitters and related mimetic compounds and antagonists, anesthetics, etc.

Encapsulating the drugs within vesicles permits to reduce the drug toxicity by preventing contact with non relevant sites. It also permits increasing bioavailability of drugs by encapsulating them in vesicles which can cross biological membranes, or by complexation with those amphiphilic derivatives which are complexants. This is especially important for macromolecules such as DNA, RNA and proteins. The delivery of nucleic acids has been proposed in gene therapy to treat genetic (e.g. cystic fibrosis, muscular dystrophy etc.) and acquired (e.g. cancers such as multiple myeloma and leukemia) diseases. In addition, antisense DNA for the treatment of various pathological conditions such as metabolic diseases, infectious diseases etc. can also be delivered. With respect to proteins, vesicles can be used to deliver growth factors, hormones, antibodies, enzymes, hemoglobin and procoagulants, etc. Since the vesicles of the invention can penetrate biological barriers, they can be used as as vehicles for large molecules that have difficulties in crossing the biological barriers.

Another potential use of the amphiphilic derivatives of the invention is in the topical application of drugs that are encapsulated in vesicles prepared from the amphiphilic derivatives, or dispersed in micelles, or dispersed in emulsions which are stabilized by the derivatives. They may also be used in diagnostics by encapsulation of contrasting agents for the purpose of imaging, for example.

The amphiphilic derivatives may also be used for nutritional supplements such as fat emulsions, solubilizing vitamins, minerals etc and introducing lipophilic and hydrophobic compounds into one formulation; for cosmetic formulations used in hair and skin treatments (e.g. shampoo, creams, lotions, etc.), when the use of a mixture of water-soluble and lipophilic compounds is required, or for slow release of perfumes.

Another field of application is in formulations for agriculture, such as formulations used for controlled delivery of herbicides, pesticides, growth hormones, or micronutrients, and for delivery of nucleic acids for genetically engineered crops, etc.

The amphiphilic derivatives may also be useful in the chemical industry for chemical synthesis when lipophilic and hydrophilic agents are involved in phase transfer, and in final product formulation as for example in emulsions where amphiphilic derivatives can be used for the stabilization of emulsions.

Methods for the Preparation of the Vesicles and Liposomes

According to the present invention, the liposomes and vesicles can be made by many of the procedures of the state of art such as those described, for example, in the following references: Benita, 1996; Fendler, 1982; Toshinori and Sunamoto, 1992; Kunitake et al., 1981a; Kunitake et al., 1981b; Kunitake and Okahata, 1977; Boder et al., 1981; Fuhrhop and Mathieu, 1984, each and all of these references being herein incorporated by reference as if fully disclosed herein.

Briefly, one can summarize some principles of these methods as follows: (i) hydration with shaking or mixing of dried phospholipids results in the spontaneous formation of multi-compartment liposomes; (ii) freeze drying the lipid dissolved in a suitable organic solvent and then adding the dried material to an aqueous solution; (iii) extrusion through polycarbonate membranes results in multi-compartment liposomes; (iv) sonication, either by probe or in bath; (v) injection of an alcoholic solution of the lipids through a small bore-Hamilton syringe into a well stirred aqueous solution at a temperature above the phase transition of the lipid; (vi) co-solubilizing a lipid with a detergent which is then removed by filtration or dialysis; (vii) injection of lipid dispersions through the small orifice of a power press (French Press), combined with reverse phase evaporation and a sequential extrusion through polycarbonate membranes; (viii) slow swelling of a lipid film in an aqueous solution; (ix) injection of a lipid-ether solution into a warm aqueous solution; (x) removal of the organic phase under reduced pressure from water-oil emulsion; (xi) injection of an immiscible organic solvent, which dissolves the lipid, into water followed by evaporation of the solvent; and (xii) dispersion of the amphiphiles, dossolved in organic solvent in water to form a water in oil emulsion. These vesicles are then suspended in aqueous medium and have an aqueous core, the two aqueous compartments separated from each other by the amphiphilic layer. Upon evaporation of the solvent results in vesicles with very high entrapment yields.

In general, it has been shown that emulsions of many different water insoluble compounds have an innate property of forming membrane vesicles when subjected to ultrasonic treatment or phase transfer conditions. A particular method can give a certain type of vesicle. Thus, for the same amphiphilic derivative, a range of different vesicle sizes can be made by choosing different methods or variations. For many applications requiring penetration through biological barriers the methods of preparation leading to vesicles of less than 100 nm diameter are preferred, and sizes in the range of about 20 nm and less are most preferred.

One preferred method for forming nanovesicles according to the present invention is by sonication. To improve encapsulation efficiency we have used a combination of the method (xii) above with sonication, which was applied after evaporation of the solvent. For obtaining larger vesicles, we used one of the above procedures as described in the specific examples. In another case, hydration with mixing of the dried amphiphilic derivative with one head group resulted in the spontaneous formation of a multi-compartment vesicle. The vesicles obtained by this method were heterogeneous, having a sphere onion-like, oblong, and tubular structures. They were however all closed and their aqueous compartments separated from each other. These multi-compartment heterodispersed vesicles were 1800 Å to 8000 Å in diameter.

In another case, multi-compartment vesicles of homogeneity and defined size were prepared by extrusion of mono-head group amphiphilic derivative at 35° C. (above the phase transition) through 1 micron Nucleopore membranes. Monolayered vesicles were formed from bipolar amphiphilic derivatives by the introduction of an aqueous buffer into an ether solution of the amphiphile derivative, followed by the removal of the ether.

Large single compartment vesicles were also obtained without sonication by injection of an alcoholic solution of double head amphiphile through a small bore Hamilton syringe into a well stirred solution at room temperature (above the phase transition of the amphiphilic derivative), followed by removal of the ethanol by evaporation.

Large single compartment bilayer vesicles were made by slow swelling of an amphiphilic film to give 0.8-micron vesicles.

Methods for Encapsulation of Active Materials

Biologically active compounds may be encapsulated in the process of forming the vesicle or can be loaded into the vesicle after its formation. The different methods of achieving encapsulation of drugs in vesicles are well known in the art and all can be used in principle with the amphiphilic derivatives of the present invention. Lipophilic molecules can be entrapped in the lipid layer. In this case it may be advantageous to make small multilayer vesicles to maximize the quantity of drug that may be encapsulated. In another embodiment of the invention, the amphiphilic derivatives that make the vesicle may be designed to maximize the adsorption and the number of adsorption sites to the drug.

For the encapsulation of hydrophilic drugs, single layer vesicles will give the highest encapsulation. High loading may be further achieved by loading the vesicle after formation using different pH gradient methods as a function of the pKa of the drug to be loaded.

Hydrophilic drugs can be loaded into the vesicles after they were formed. For drugs having ionizable amine groups, the loading is across an ammonium ion gradient. Ammonium ions within the vesicles are in equilibrium with ammonia, which is freely permeable, and protons accumulate as the ammonia is lost from the liposomes. This leads to a lower inside/higher outside pH gradient. After establishing the gradient, excess of ammonium ions within the liposomes provides a reservoir of protons to maintain the pH gradient over time. Thus, as amine drugs permeate across the membrane into the liposomes, they are converted into ammonium ions which keeps them entrapped.

A similar approach can be used for loading high drug concentration of an ionizable drug, which is negatively charged in its ionized state. In this case, liposomes are formed with weak acids (formic, acetic, propanoic acid, etc) having a higher inside/lower outside pH gradient. The gradient allows the loading of weak acid compounds as previously described in U.S. Pat. No. 5,939,096, herein incorporated by reference as if fully disclosed herein.

The invention will now be illustrated by the following non-limiting Examples.

EXAMPLES

The Derivatives 1-20 and Precursors 1-18 are identified in the Examples by their structure and numbers in bold. The methods of preparation of the compounds are depicted in the Appendix as Schemes 1-20.

Example 1

General Procedures for Making Amphiphilic Vernonia Oil Derivatives

Functionalization of vernonia oil derivatives and formation of the amphiphilic head group was achieved in several ways by functional group transformation of the existing epoxy group of the vernonia oil derivatives or by functionalizing a pendant side group. The procedures that follow in this Example were used to functionalize or derivatize the various natural or synthetic derivatives of vernonia oil.

(a) Oxiranyl ring opening: A solution of the vernonia oil derivative in a polar solvent such as ethanol or a non polar solvent such as toluene was treated with a solution of acidic or nucleophilic reagent. The reaction mixture was refluxed until TLC indicated that the oxiranyl starting material was reacted. The solution was then cooled down to room temperature, treated with an appropriate organic solvent (e.g. chloroform, methylene chloride, ether, ethyl acetate), poured on water and extracted. The organic solvent was dried over a dehydrating agent (e.g. sodium sulfate, magnesium sulfate), filtered off and evaporated. The crude substituted β-alcohol was then purified by recrystalization or by column chromatography.

Alternatively, the ring opening was achieved in the neat at 50° C. In such a way were prepared β-alcohol derivatives such as: β-ester, β-azido, β-sulfinic acid and β-amino alcohols.

(b) Formation of β-azido derivatives: The β-azido derivatives were prepared according to three different procedures.

Method (i): An ethanolic solution of the vernonia oil derivative, sodium azide and ammonium chloride was treated with water and refluxed for two days. After cooling to room temperature, the mixture was extracted with ether, dried over magnesium sulfate and evaporated. Purification was achieved by column chromatography on silica gel 60. The β-azido derivative was identified by the 2108 $cm^{-1}$ vibration in its infrared spectrum.

Method (ii): A methanolic solution of the vernonia oil derivative, sodium azide and triethyl amine was refluxed for two days.

Method (iii): A methanolic solution of the vernonia oil derivative, sodium azide and ammonium chloride was refluxed for two days.

(c) Reduction of the β-azido derivatives: Reduction of the azido derivatives was achieved by three different methods:

Method (i): A mixture of the azide with hexadecyltrimethyl ammonium bromide and CoCl, was treated with a solution of sodium borohydride in water. The mixture was allowed to react for two days at room temperature, then ether was added, and the solution was extracted and washed several times. The organic extracts were separated, dried over a dehydrating agent, filtered and evaporated.

Method (ii): A mixture of the azide, $CoCl_2$ and sodium borohydride in iso-propanol was refluxed for two days. After cooling, the reaction was treated with chloroform and quenched with HCl. The phases were separated and the organic phase was washed, dried, filtered and evaporated.

Method (iii): The catalytic hydrogenation of the azid group was carried out by treating the azido alcohol derivative in methanol with 10% Pd—C, followed by hydrogenation under atmospheric pressure at room temperature for 12 h. After filtration of the catalyst, the methanolic solution was concentrated and purified by column chromatography. In addition to the reduction of the azido group, catalytic hydrogenation also brought about the reduction of the double bond.

(d) Quaternization of free amino groups: To a mixture of the amino precursor in nitromethane, the alkyl halide was added in large excess. The mixture was stirred and heated at 60° C. for two days. After cooling to room temperature, the reaction mixture was filtered and the solvent was removed under reduced pressure to give the quaternary ammonium salt. (e) Amination of haloesters: A mixture of the halo precursor and the secondary or tertiary amine in iso-propanol was stirred for 3 hours at 80° C. The solvent was evaporated under reduced pressure and the crude ammonium salt was purified.

(f) Acylation of free amino compounds with vernonia oil esters. To a neat mixture containing the vernonia oil ester and the mono or poly-amine, a base such as sodium methoxide was added and the solution was heated at 60° C. for 4 hours. After cooling to room temperature the reaction mixture was triturated with hexane and the precipitate was filtered, washed with water until neutral and purified from alcohol.

Example 2

Synthesis of 13-azido-12-hydroxyoctadec-9-enoic acid methyl ester (Precursor 1)

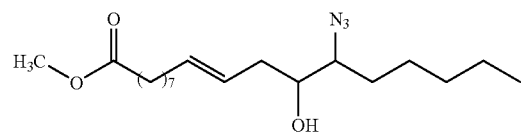

Precursor 1 was prepared by reacting methyl vernolate and sodium azide by three different methods as shown in Scheme 1, as follows:

Method (a): A mixture of 1.0 g (0.00225 mol) methyl vernolate, 0.8 g (0.01 mol) sodium azide and 0.65 g ammonium chloride in 50 ml ethanol and 5 ml of water was refluxed for 48 hours. After cooling to room temperature, 50 ml of ether and 50 ml of water were added and the phases were separated. The organic phase was washed with water and dried over sodium sulfate. The IR spectrum showed a characteristic peak of the azide group at 2108 $cm^-$. The crude product was purified by column chromatography on silica gel 60. The elution was carried out first with a mixture of petroleum ether and ether and then the eluent was changed to methanol.

$^1$H NMR (500 MHz, $CDCl_3$): δ=3.47 (—CH—OH), 3.16 (—CH—$N_3$);

$^{13}$C NMR (500 MHz, $CDCl_3$): δ=66.7 (—CH—OH), 72.9 (—CH—$N_3$);

Elemental Analysis: Calculated for $C_{19}H_{35}N_3O_3$ (MW=353.5): N, 11.9%: Found: N, 11.0%.

Method (b): A mixture of 1.16 g (0.0026 mol) methyl vernolate, 3 g (0.046 mol) sodium azide and 0.1 ml triethyl amine in 80 ml dry methanol was refluxed for 42 hours. Then, the reaction was cooled, the solvent was evaporated under reduced pressure and ether was added. The solution was dried over sodium sulfate, filtered and evaporated. Thus were obtained 0.5 g of the desired product. The IR spectrum was indicative of the azide group.

Method (c): A mixture containing 5.8 g methyl vernolate, 3.9 g sodium azide and 3.21 g ammonium chloride in 250 ml absolute methanol was refluxed for 42 hours. Then, the reaction was cooled down and the solvent was evaporated. After evaporation, ether and water were added. The organic phase was washed with water until there was no reaction with silver nitrate. The solution was dried over sodium sulfate, filtered and the solvent evaporated, thus obtaining 5.06 g of the azide intermediate. The IR spectrum showed a peak indicative of the azide group.

Example 3

Preparation of Derivative 1

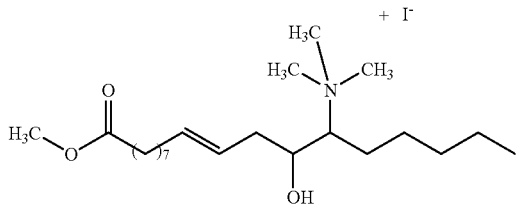

Derivative 1 was prepared from Precursor 1 in two steps: reduction of Precursor 1, which was achieved in two different ways, and exhaustive alkylation, as follows:

The two methods utilized for the reduction of Precursor 1 are:

Method (a): To a mixture of 0.42 g of the azide prepared above, 46 mg $CoCl_2$ and 0.13 g hexadecyltrimethyl ammonium bromide, 0.6 g sodium borohydride in 40 ml of water was added dropwise and the reaction mixture was allowed to stand for a period of 20 hours at room temperature. Then ether was added and the phases were separated. The organic phase was washed with water, dried over sodium sulfate, filtered and evaporated. There was obtained 2.86 g of crude product. The product was dissolved in ether and HCl gas was bubbled through the solution. At this point some product precipitated from the solution. After the solution was decanted, chloroform was added to the residue and treated with triethyl amine. The mixture was filtered and the solvent evaporated, thus obtaining Derivative 1. IR showed the disappearance of the azide peak.

Method (b): A mixture of 0.5 g of the azide, 0.56 g $CoCl_2$ and 0.16 g sodium borohydride in 10 ml iso-propanol was refluxed for 20 hours. After cooling, the reaction was treated with chloroform and 5% HCl. The phases were separated and the organic phase was washed with water, dried over sodium sulfate, filtered and evaporated, thus obtaining Derivative 1. IR did not show the presence of the azide group.

$^1$H NMR (200 MHz, $CDCl_3$): δ =2.5 (C$\underline{H}$—$NH_2$), 3.3 (C$\underline{H}$—OH);

$^{13}$C NMR (200 MHz, $CDCl_3$): δ=56.0 ($\underline{C}H$—$NH_2$), 78.8 ($\underline{C}H$—OH);

Elemental analysis: Calculated for $C_{19}H_{39}NO_3$ (MW=329.29) N, 4.3%: Found: N, 4.0%.

Next, the β-amino alcohol was treated with excess iodomethane, according to the procedure given in Example 1(d), and Derivative 1 was obtained.

Example 4

Synthesis of 13-(2-chloroacetoxy)-12-hydroxyoctadec-9-enoic acid methyl ester (Precursor 2)

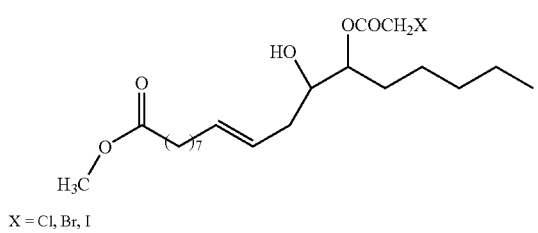

X = Cl, Br, I

Precursor 2 was prepared in one step from methyl vernolate as shown in Scheme 2, as follows:

A mixture of 4.43 g methyl esters of vernonia oil (containing 3.1 g, 0.01 mol of methyl vernolate) and chloroacetic acid (1.23 g, 0.012 mol) was dissolved in 20 ml toluene. The mixture was heated for 14 hours at 90° C. The course of the reaction was monitored by TLC. The reaction mixture was dissolved in diethyl ether and washed 3-4 times with water. The organic layer was separated, dried and the solvent was evaporated under reduced pressure. The mixture of products obtained was purified by silica gel column chromatography, using n-hexane and diethyl ether (1:1 v/v) as eluent, thus obtaining pure Precursor 2.

IR (neat, $cm^{-1}$): 3450 (OH), 1280, and 1300 (chloro acetate), 780 (C—Cl);

$^1$H NMR (200 MHz, $CDCl_3$): δ=0.88 ($CH_3$), 1.3 (($CH_2$)$_7$), 1.63 ($CH_3$—O—CO—$CH_2$—$CH_2$—), 1.99 (—$CH_3$—$\overline{C}H_2$), 2.27 ($CH_3$—O—CO—$CH_2$—), $\overline{3.48}$ (—C$\underline{H}$—OH), $3.6\overline{7}$ (C$\underline{H}_3$—O—CO), 4.09 ($CH_2$—Cl), 4.95 (—C$\underline{H}$—O—CO—$CH_2$—Cl), 5.33-$\overline{5.53}$ (C$\underline{H}$=C$\underline{H}$);

$^{13}$C NMR (500 MHz, $CDCl_3$): δ=14.03, ($CH_3$), 33.66 and 34.12 ($CH_3O$—CO—$CH_2$—), 24.96 and $\overline{25}.31$ [($CH_2$)$_n$], 41.04 ($CH_2$—Cl), 51.$\overline{53}$ ($CH_3OCO$), 71.87 and 71.$\overline{98}$ (—$\underline{C}H$—O$\underline{H}$), 123.33-124.0 and 133.71-133.96 (—$\underline{C}H$=$\underline{C}H$—), 167.24 (—CHO—$\underline{C}O$—$CH_2Cl$), 174.41 ($C\overline{H_3}O$—$\overline{C}O$—$CH_2$);

Elemental Analysis Calculated For $C_{21}H_{37}O_5Cl$ (M.W.=404.5): Cl, 8.78. Found Cl, 7.88.

Example 5

Synthesis of Amphiphilic Derivative 2

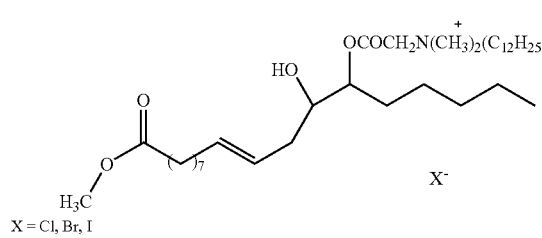

X = Cl, Br, I

Derivative 2 was prepared from Precursor 2 as shown in Scheme 2, as follows:

A mixture of Precursor 2 purity of 90%, 0.81 g, 2.0 mmol) and dimethyldodecylamine (0.43 g, 2.0 mmol) in 2 ml isopropanol was stirred for 3 hours at 80° C. The solvent was evaporated under reduced pressure to give 1.2 g of the ammonium salt Derivative 2 as a viscous product. Derivative 2 was obtained from the viscous product by column chromatography with chloroform:methanol 9:1 (v/v) as the eluent. The chloride ion amount of this product determined by argentometric titration was 4.75% (calculated 5.74%). The yield of quaternization was 82.7%.

IR (neat, $cm^{-1}$): 3350 (OH), 1740 and 1165 (ester group), 1240, and 1200;

$^1$H NMR (200 MHz, $CDCl_3$): δ=0.81 ($CH_3$), 3.43 and 3.45 ($CH_2$—$N(CH_3)_2$—$CH_2$—), 3.54 (—$N(CH_3)_2$—$CH_2$—$CH_2$—), 3.59 ($CH_3$—O), 3.66 (CH—OH), 4.71 (—O—CO—$CH_2$—$N(CH_3)_2$), 4.88 (—CH—O—CO), 5.36-5.42 (—CH═CH—);

$^{13}C$ NMR (500 MHz, $CDCl_3$): δ=13.99, ($CH_3$), 51.34 ($CH_3$O—CO—), 51.78 (—$CH_2$—$N(CH_3)_2$—$CH_2$—), 61.07 and 61.56 ($N(CH_3)_2$—$CH_2$—$CH_2$—), 64.09 and 64.71 (—CO—$CH_2$—$N(CH_3)_2$), 71.36 and 71.69 (—CH—OH), 79.84 (—CH—O—CO—$CH_2$—), 123.44-131.11 (—CH═CH—), 164.70 and 164.89 (CH—O—CO—$CH_2$—$N(CH_3)_2$), 174.19 ($CH_3$—O—CO);

Elemental Analysis Calculated For $C_{35}H_{68}NO_5Cl$ (MW=619): N, 2.27, Cl, 5.75. Found N, 2.2 and Cl, 5.05 (purity of 90% gives Cl % of 5.16).

Example 6

Synthesis of Amphiphilic Derivative 3

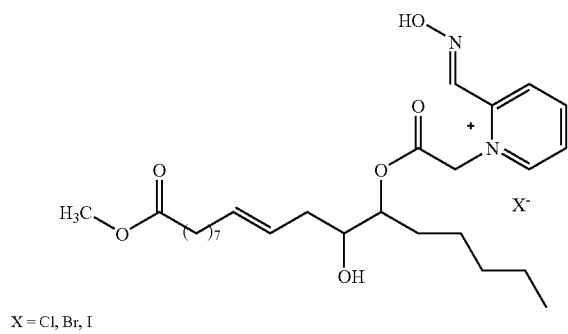

X = Cl, Br, I

Derivative 3 was prepared from Precursor 2 and 2-pyridinealdoxime as shown in Scheme 3, as follows:

A solution of bromoacetoxy Precursor 2, 4.49 g (0.01 mol), and 1.22 g (0.01 mol) of 2-pyridinealdoxime in 8.5 ml dry acetonitrile was allowed to stand at room temperature for 9 days. The solvent was evaporated and the residue was treated with 20 ml diethyl ether and then left in the refrigerator. The white semi solid precipitate of Derivative 3 was filtered and washed with dry diethyl ether. Yield of quaternary pyridinium salt was 1.15 g (20%). Amount of bromide ion was 12% (calculated value is 14%).

Alternatively were used the chloroacetoxy and iodoacetoxy Precursors.

$^1$H NMR (500 MHz, $CDCl_3$): δ=0.85 (3H, $CH_3$), 3.64 (3H, $CH_3$—O), 3.72 (1H, CH—OH), 4.5 (1H, CH—OH, 4.91 (1H, CH—O—CO), 5.46 (2H, CH═CH), 5.99 and 6.32 (2H, OC—$CH_2$—$N^+Py$), 7.96, 8.30, 8.50, 8.54, 9.18 (5H, Py and C H═NOH), 11.98 (1H, N═OH);

$^{13}C$ NMR (500 MHz, $CDCl_3$): δ=14.11 ($CH_3$), 51.47 ($CH_3$—O), 60.58 ($CH_2$—$N^+Py$), 71.71 and 71.94 (CH—OH), 80.45 (CH—O—CO), 124.42 and 133.43 (CH═CH), 123.22, 127.30, 132.44, 141.43, 146.50, 147.73 (Py, CH═N—OH), 165.72 and 165.88 (CH—O—CO), 174.41 ($CH_3$—O—CO).

Example 7

Preparation of Amphiphilic Derivative 4

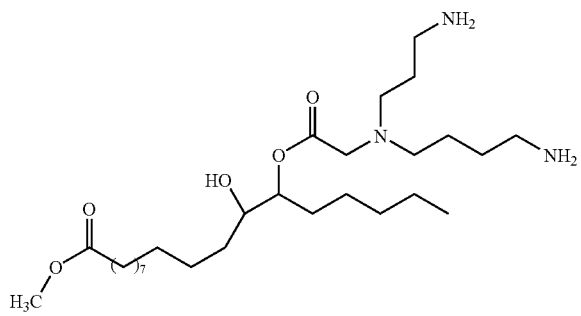

Derivative 4 was prepared in one step from Precursor 2 and N,$N^8$-dicarboxybenzoxy spermidine. The N,$N^8$-dicarboxybenzoxy spermidine was prepared according to the procedure described in WO 99/02190.

Purified N,$N^8$-dicarboxybenzoxy spermidine was reacted with Precursor 2 under the conditions described in Example 1(f) hereinabove. The dicarbobenzoxy protecting groups were removed by hydrogenation according to the procedure described in WO 99/02190 as done with spermidine cholesterol. This procedure also reduced the double bond of the vernolate residue, thus obtaining Derivative 4. Purification of the product was achieved by silica gel chromatography utilizing chloroform as the eluent.

Example 8

Preparation of Amphiphilic Derivative 5

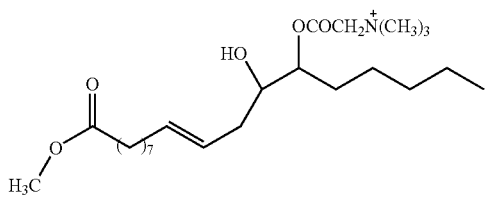

Derivative 5 was prepared from Precursor 2 and trimethylamine according to the general procedure described in Example 1(e), as shown in Scheme 5.

Example 9

Preparation of Amphiphilic Derivative 6

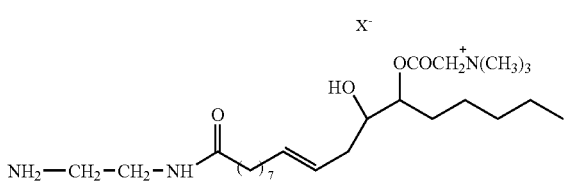

Derivative 6 was prepared from Derivative 5 and ethylene diamine according to the general procedure described in Example 1(f) as shown in Scheme 5.

Example 10

Preparation of Amphiphilic Derivative 7

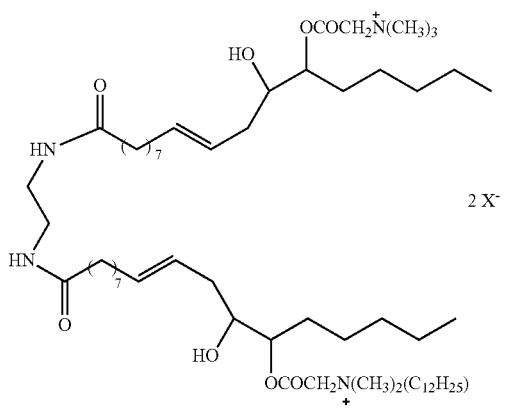

Derivative 7 is prepared by condensing Derivative 6 and Derivative 2 as shown in Scheme 5, as follows: A solution of Derivative 2 (0.01M concentration) is added to a solution containing Derivative 6 (0.03M concentration) and the mixture is allowed to stir until all of Derivative 2 is consumed.

Example 11

Preparation of 11-(3-pentyloxiranyl)undec-9-enoic acid 4-[11-(3-pentyloxiranyl)undec-9-enoyloxy]butyl ester

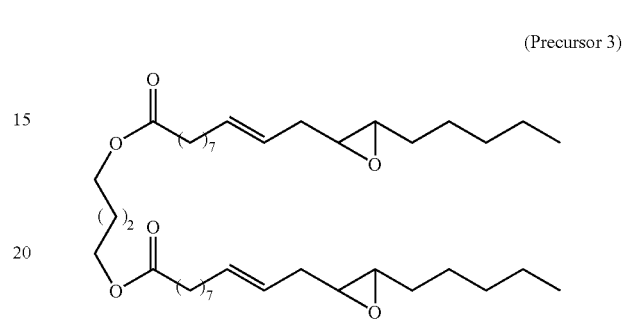

(Precursor 3)

Precursor 3 was prepared from vernonia oil and 1,4-butanediol as shown in Scheme 6, as follows:

1,4-Butanediol (0.16 g, 0.00177 mol) in dry THF was added to a suspension of potassium hydride (0.38 g, 0.00947) in dry THF and the mixture was stirred for one hour at room temperature. Then 2.1 g (0.00226 mol) of vernonia oil in THF was added and the mixture was refluxed for 2 hours. The reaction was cooled to room temperature and then hexane was added. The solution was washed with water, dried over sodium sulfate, and evaporated under reduced pressure, thus obtaining 1.5 g of Precursor 3. The product contained 13.4% of epoxy groups (calculated value is 13%).

$^1$H NMR (200 MHz, CDCl$_3$): δ=5.4 (CH=CH), 4.0 (CH$_2$—O), 2.8 (epoxy protons), 2.2 (CH$_2$—CO).

Example 12

Preparation of amphiphilic 13-amino-12-hydroxyoctadec-9-enoic acid 4-(13-amino-12-hydroxyoctadec-9-enoyloxy)butyl ester

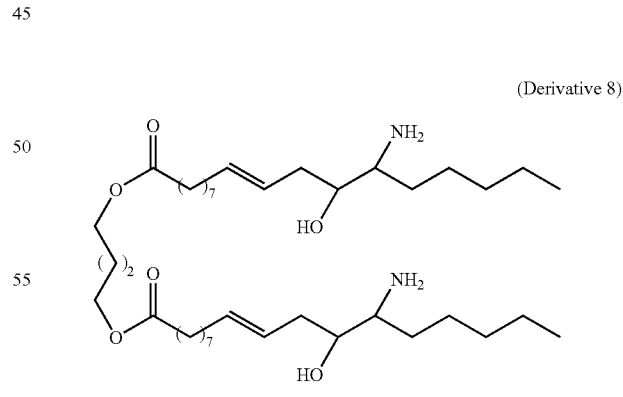

(Derivative 8)

Derivative 8 was prepared in two steps from diester Precursor 3 as shown in Scheme 6, as follows:

To 0.5 g of the Precursor 3 in 40 ml of dry methanol containing 50 μl of triethylamine, 0.3 g of sodium azide was added. The reaction mixture was refluxed for 48 hours. After cooling, the solvent was removed under reduced pressure and the residue was dissolved in ether, washed with water, and dried over anhydrous sodium sulfate. The ether was evaporated and the product was chromatographically purified.

Next, the product was dissolved in 12 ml of methanol and treated with 0.1 g 10% Pd—C. The dark reaction mixture was hydrogenated under atmospheric pressure at room temperature for 12 h. After filtration of the catalyst, the methanolic solution was concentrated and purified by column chromatography (silica gel with a chloroform:methanol eluent in a ratio of 1:1) to obtain Derivative 8.

Elemental analysis: Calculated for $C_{40}H_{79}N_2O_6$ (MW=684) N, 4.1%, Found: N, 3.8%.

Example 13

Preparation of Amphiphilic Derivative 9

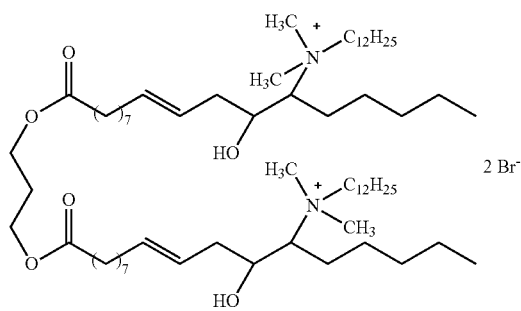

Derivative 9 was prepared from Derivative 8 by sequential alkylation with methyl iodide and dodecyl bromide as shown in Scheme 6, as follows:

To a mixture of 2 g (2.9 mmol) of Derivative 8 and 4.0 g 1,8-bis(dimethylamino) naphthalene (acting as a proton sponge) in 50 ml nitromethane, 2.7 g (19 mmol) methyl iodide was added. The mixture was stirred and heated at 60° C. for 48 h. After cooling at room temperature, the reaction mixture was filtered and the solvent was removed under reduced pressure to give 2 g of the tertiary amine.

Next, a mixture of 2 g of the tertiary methyl amine (2.6 mmol) and 6.7g (27 mmol) of dodecylbromide in 50 ml dibutyl ether was stirred at the reflux temperature for 24 h. Then the reaction was cooled and the solvent removed, thus obtaining Derivative 9.

$^1$H NMR (200 MHz, CDCl$_3$): δ=3.3 [N$^+$(CH$_3$)$_2$ and N$^+$—CH$_2$]; 3.6 (N$^+$—CH);

$^{13}$C NMR (200 MHz, CDCl$_3$): δ=45.6 [N$^+$(CH$_3$)$_2$]; 64.0 (N$^+$—CH$_2$); 80.9 (N$^+$—CH).

Elemental analysis: calculated for $C_{68}H_{138}O_6N_2Br_2$ (MW=1239): N, 2.25%, Br, 12.9%;

Found: N, 2.04%; Br, 11.0%

Example 14

Synthesis of 11-(3-pentyloxiranyl)-undec-9-enoic acid {2-[11-(3-pentyloxiranyl)undec-9-enoylamino]ethyl}amide

[Trivial name: N,N'-ethylene bis (vernolamide)]

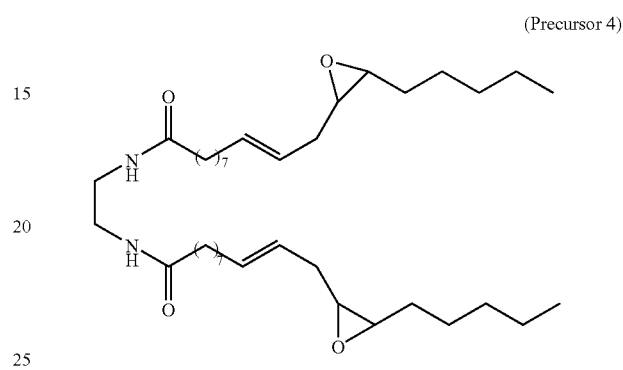

(Precursor 4)

Precursor 4 was prepared in two ways: from trivernolin, according to Grinberg and Kolot [Grinberg and Kolot, 1994] or from methyl vernolate, as shown in Scheme 7, as follows:

Method (a): From Trivernolin

A mixture of vernonia oil (2 g, 0.002 mol, based on molecular weight of 926) and ethylene diamine (0.36 g, 0.006 mol) was heated at 60° C. for 5 hours. After cooling, chloroform was added and the reaction mixture was washed 4-5 times with 100 ml water in order to remove the unreacted diamine. The organic layer was separated, dried over anhydrous magnesium sulfate and evaporated under reduced pressure to give a semi-solid product. Hexane (50 ml) was added to the residue to separate unreacted vernonia oil to give a product containing both the desired diamide and the monoamino amide (according to TLC). The fractions containing the diamide were eluted with a 9:1 mixture of chloroform:methanol. The pure Precursor 4 was obtained in 65% yield. The amount of epoxy groups by titration was 10%.

Method (b): From Methyl Vernolate

To a solution containing methyl vernolate (3.1 g, 0.01 mol) and 1,2-ethylenediamine (0.3 g, 0.005 mol), 0.6 ml of 2N sodium methoxide was added and the solution was heated at 60° C. for 4 hours. After cooling to room temperature, the reaction mixture was triturated with hexane and the precipitate was filtered. The precipitate was washed with water until neutral to give 2.46 g (82% yield) of Precursor 4. Purification was achieved by washing the product with methanol, thus giving the diamide in 80-85% yield.

Mp=125-128° C.;

IR (KBr Pellet, cm$^{-1}$): 3330 (NH), 1630 and 1540 (amide I and II), 820 and 840 (epoxy);

$^1$H NMR (500 MHz, CDCl$_3$): δ=0.9 (CH), 1.30-1.52 ((CH$_2$)$_n$), 2.05 (CH=CH—CH$_2$-epoxy), 2.13 (NH—CO—CH$_2$—), 2.89-2.94 (epoxy), 3.37 (CH$_2$—N), 5.2-5.6 (CH=CH, 6.34 (NH—C);

$^{13}$C NMR (500 MHz, CDCl$_3$): δ=13.95 (CH$_3$), 22.54 (CH$_3$—CH$_2$—), 40.16 (NH—CH$_2$—), 56.4-57.1 (epoxy), 123.9-132.4 (CH=CH), 174.3 (CO amide).

Elemental Analysis for $C_{38}H_{68}O_4N_2$: Calculated C, 74.03, H, 11.04, N, 4.54. Found C, 73.87, H, 11.31, N, 4.34.

Example 15

Preparation of chloroacetic acid 12-{2-[13-(2-chloroacetoxy)-12-hydroxyoctadec-9-enoylamino]ethylcarbamoyl}-2-hydroxy-1-pentyldodec-4-enyl ester (Precursor 5)

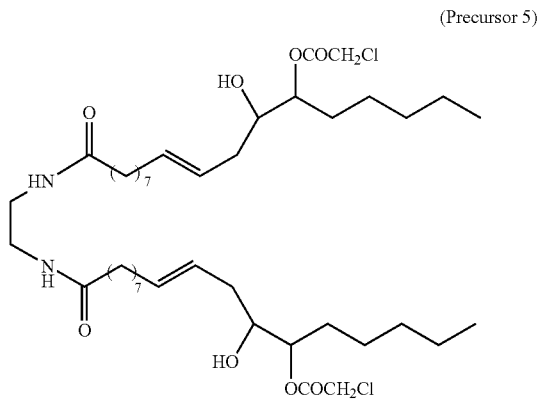

Precursor 5 was prepared from Precursor 4 as shown in Scheme 8, as follows:

A mixture of the Precursor 4 (3.08 g, 5 mmol) and chloroacetic acid (1.23 g, 13 mmol) was heated at 100° C. for 3.5 hours under a nitrogen atmosphere. The reaction mixture was dissolved in chloroform and washed with 5% aqueous sodium bicarbonate (2-3 times) and water (3 times). The organic layer was dried over sodium sulfate and the solvent was evaporated under reduced pressure, thus giving Precursor 5. Yield of the product 3.9 g (97% yield). The course of the reaction was monitored by examination of the epoxy-group amount in the reaction mixture. The amount of epoxy group in this product was 0.3%.

An alternative procedure involves the addition of chloroacetic acid to a preheated solution of the precursor in toluene at 60° C. After the addition, the temperature was raised to and maintained at 90° C. for 10 hours. After cooling, the mixture was worked up as described above. The yield of Precursor 5 was 95% with only 0.2% of epoxy group remaining.

IR (neat, cm$^{-1}$): 3330 (OH), 1730 and 1180 (ester), 1280 and 1300 (chloro acetate), 780 (C—Cl);

$^1$H NMR (200 MHz, CDCl$_3$): δ=0.81 (CH$_3$), 3.28 (CH2-NH), 3.65 (—H—OH), 4.05 (CH$_2$—Cl), 4.90 (—CH—O—CO—CH$_2$—Cl), 5.40 (CH=CH), 6.65 (NH);

$^{13}$C NMR (500 MHz, CDCl$_3$): δ=13.89, (CH$_3$),39.68 (—CH2-NH), 40.98 (CH$_2$—Cl), 71.59 and 71.98 (—CH—OH), 78.32 (—CH$_2$—O—COCH$_2$Cl), 123.42-124.57 and 133.20-133.29 (—CH=CH—), 167.08 (—CHO—CO—CH$_2$Cl), 167.21 (—O—CO—CH$_2$-Cl), 174.60 (—NH—CO);

Elemental Analysis Calculated For $C_{42}H_{74}O_8N_2Cl_2$ (M.W.=805): N, 3.48, Cl, 8.82. Found N, 3.4, Cl, 7.84.

Example 16

Preparation of Amphiphilic Derivative 10

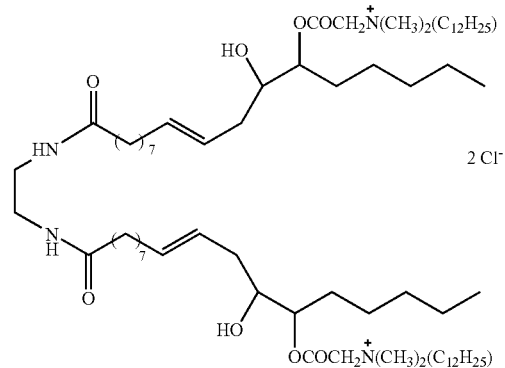

Derivative 10 was prepared from Precursor 5 as shown in Scheme 8, as follows:

A mixture of the Precursor 5 (1.61 g, 2 mmol), dimethyl-dodecylamine (0.85 g, 4 mmol) and 3.7 ml iso-propanol was stirred for 3 hours at 80° C. The solvent was evaporated at room temperature under reduced pressure, thus obtaining Derivative 10. The amount of chloride ion in the product as determined by argentometric titration was 4.9% (calculated 5.76%). Yield of quaternization was 85%.

IR (neat, cm$^{-1}$): 3300 (OH), 1740 (ester group), 1630 and 1540 (amide I and II), 1466 (NCH$_3$);

$^1$H NMR (200 MHz, CDCl$_3$): δ=0.80 (CH$_3$), 3.27 (—C H$_2$—NH), 3.40 (CH$_2$—N(CH$_3$)$_2$—CH$_2$—), 3.49 (—N (CH$_3$)$_2$ —CH$_2$—CH$_2$—), 3.65 (—O—CO—CH$_2$—N (CH$_3$)$_2$—), 4.88 (—CH—O—CO), 5,19, 5.25-5.38 (—CH=CH—), 7.72 (—NHCO);

$^{13}$C NMR (500 MHz, CDCl$_3$): δ=13.91 (CH$_3$); 39.42 (—CH$_2$—NH—), 51.42 and 51.61 (CH$_2$—N(CH$_3$)$_2$—CH$_2$—), 61.42 (N(CH$_3$)$_2$—CH$_2$—CH$_2$—), 64.84 (—CO—CH$_2$—N(CH$_3$)$_2$—), 71.36 and 71.66 (—CH—OH), 79.80 (—CH—O—CO—CH$_2$—), 123.44 and 124.66, 132.14-133.22 (CH=CH—), 164.48 (CH—O—CO—CH$_2$—N(CH$_3$)$_2$), 174.33 (CH$_3$—O—CO);

Elemental Analysis Calculated For $C_{70}H_{136}N_4O_8Cl_2$ (M.W.=123 1): N, 455, Cl, 5.76. Found N, 4.50 and Cl, 4.9.

Example 17

Preparation of 2-hydroxy-12-[2-(12-hydroxy-13-sulfinoxyoctadec-9-enoylamino)-ethylcarbamoyl]-1-pentyldodec4-enyl ester sulfonate (Derivative 11)

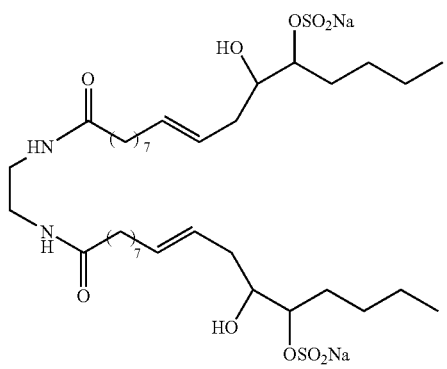

To a solution of sodium bisulfite (0.78 g, 7.5 mmol) in 10 ml water, Precursor 4 was added (3.08 g, 5 mmol) in 20 ml iso-propanol followed by a 75% solution 0.01 g of t-butyl peracetate in toluene. The reaction mixture was heated at 90° C. for 16 hours. The titration of the epoxy groups at the end of the reaction showed a 20% yield.

Example 18

Preparation of 11-(3-pentyloxiranyl)undec-9-enoic acid {3-[11-(3-pentyloxiranyl)undec-9-enoylamino] propyl}amide Trivial name: N,N'-propylenebis(vernolamide)

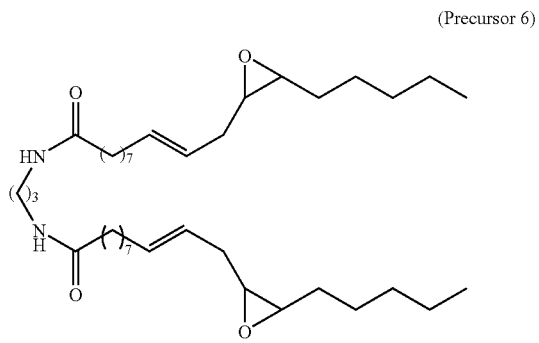

(Precursor 6)

Precursor 6 was prepared from methyl vernolate and propylenediamine as shown in Scheme 10, according to the procedure described in Example 1(f).

Mp=123-125° C.;

$^1$H NMR (200 MHz, CDCl$_3$): δ=2.88-2.95 (epoxy), 3.23-3.32 (CH$_2$—N), 5.34 and 5.52 (—CH=CH—), 6.2 (NH);

Elemental Analysis Calculated for C$_{39}$H$_{70}$N$_2$O$_4$: C, 78.28, H, 11.11, N, 4.44. Found C, 73.9, H, 11.37, N, 4.35.

Example 19

Preparation of chloroacetic acid 12-{3-[13-(2-chloroacetoxy)-12-hydroxyoctadec-9-enoylamino]propylcarbamoyl}-2-hydroxy-1-pentyldodec-4-enyl ester

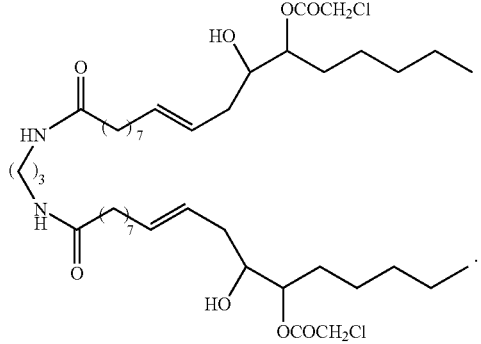

(Precursor 7)

Precursor 7 is prepared by reacting Precursor 6 with haloacetic acid in a procedure similar to that described in Example 1(a) and shown in Scheme 10.

Example 20

Preparation of amphiphilic Derivative 12

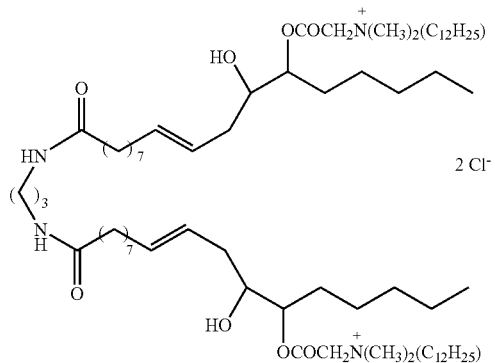

2 Cl$^-$

Derivative 12 is prepared by reacting Precursor 7 with dimethyl dodecylamine according to the procedure described in Example 1(e) and shown in Scheme 10.

Example 21

Preparation of 11-(3-pentyloxiranyl)undec-9-enoic acid {4-[11-(3-pentyloxiranyl)undec-9-enoylamino] butyl}amide

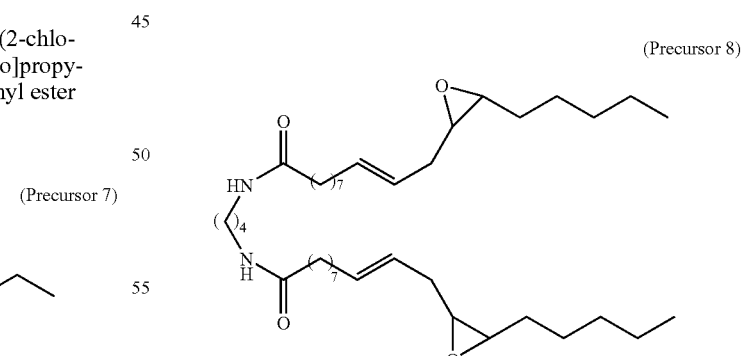

(Precursor 8)

Precursor 8 was prepared from methyl vernolate and 1,4-diaminobutane according to the procedure described in Example 1(f) and shown in Scheme 11.

Mp=122-124° C.;

Elemental Analysis: calculated N % 4.35, found 4.20.

Example 22

Preparation of 11-(3-pentyloxiranyl)undec-9-enoic acid {6-[11-(3-pentyloxiranyl)undec-9-enoylamino]hexyl}amide

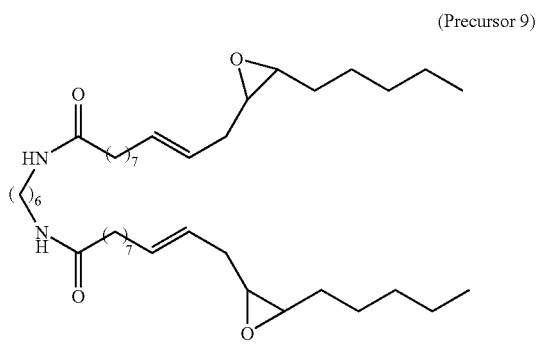
(Precursor 9)

Precursor 9 was prepared from methyl vernolate and 1,6-diaminohexane according to the procedure described in Example 1(f) and shown in Scheme 11.

Mp=123-124° C.;
Elemental Analysis: calculated N % 4.17, found 4.13.

Example 23

Preparation of 11-(3-pentyloxiranyl)-undec-9-enoic acid (2-({2-[11-(3-pentyloxiranyl)-undec-9-enoylamino]ethylamino}ethyl)amide

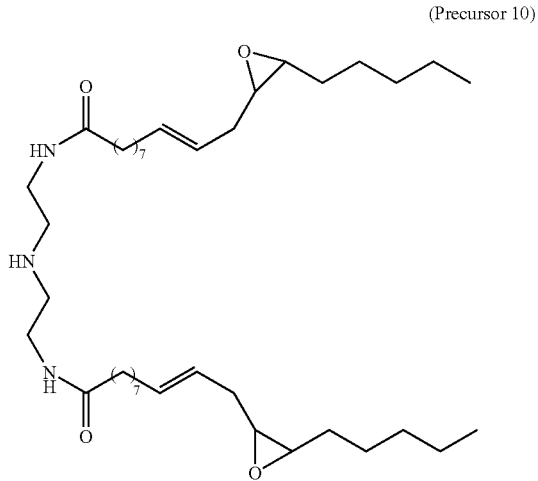
(Precursor 10)

Precursor 10 was prepared from diethylene triamine and methyl vernolate or trivernolin as shown in Scheme 12, as follows:

A mixture of 9.26 g (10 mmol of vernonia oil based on a molecular weight 926) and 2.06 g (20 mmol) diethylenetriamine (DETA) was heated at 60° C. for 6 h.

In order to remove the unreacted starting materials, the reaction mixture was triturated with 200 ml diethyl ether. The precipitate (7.4 g) that contained a mixture of diamides was filtered and washed with diethyl ether. The absence of vernonia oil was detected by TLC (eluent n-hexane:diethyl ether 1.5:1 v/v). The absence of DETA in the product was detected with phenolphthalein. The product, containing one main spot with $R_f$=0.6, was isolated in a 50% yield from the mixture by silica gel chromatography using chloroform with increasing amounts of methanol as eluent.

IR (KBr, cm$^{-1}$): 3330, 1630 and 1540 (secondary amide), 1120 (carbon-nitrogen stretch absorption of a secondary amine (R—CH2-NH—R)], 840 and 820 (epoxy group).

$^1$H NMR (500 MHz, CDCl$_3$): δ=0.84-0.90 (CH$_3$), 2.72-2.75 (—H$_2$C—NH—CH$_2$—), 2.88-2.91 (epoxy protons), 3.30-3.33 (—NH—CH$_2$—CH$_2$—NH—CO), 5.46-5.50 (—CH=CH—), 6.07 (—NH—CO—);

$^{13}$C NMR (500 MHz, CDCl$_3$): δ=13.98 (CH$_3$), 39.03 (—CH$_2$—NH—CO), 48.522 (—H$_2$C—NH—CH$_2$—), 56.55 and 57.22 (epoxy carbons), 123.89 and 132.54 (CH=CH), 173.59 (NH—CO—);

Elemental Analysis: calculated for C$_{40}$H$_{273}$O$_4$N$_3$ (M.W.=659%): N, 6.37%, Found N, 6.1%.

Example 24

Preparation of Amphiphilic Derivative 13

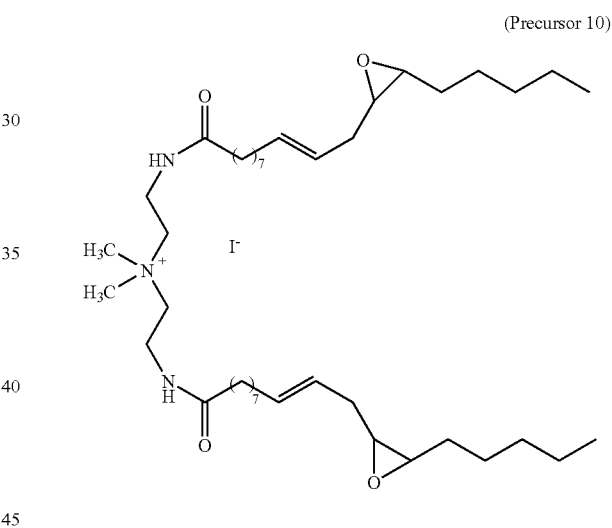
(Precursor 10)

Derivative 13 was prepared in one step by reacting Precursor 10 with excess methyl iodide, as shown in Scheme 12, as follows:

Precursor 10 (6.59 g, 10 mmol) was dissolved in 170 ml dry ethyl acetate at 60° C. and then 1,2,2,6,6-pentamethylpiperidine (1.55 g, 10 mmol) was added. Excess of methyl iodide (28.4 g, 200 mmol) was gradually added to reaction mixture. The reaction was heated at 60° C. for 2 hours and then allowed to stand overnight at room temperature. The pentamethylpiperidine hydroiodide that precipitated was removed by filtration and the filtrate was evaporated under reduced pressure to give 5.93 g (90% yield) of Derivative 13 as a white product with melting point of 63-65° C. The amount of iodide ion in the product as determined by argentometric titration was 12.5% (Calculated value for C$_{42}$H$_{78}$O$_4$N$_3$I, M.W=815 is 15.57%.)

IR (KBr, cm$^{-1}$): 3330, 1640, 1560 (secondary amide), 840 and 820 (epoxy group);

$^1$H NMR (200 MHz, CDCl$_3$): δ=0.85-0.89 (CH$_3$), 2.81-2.92 (epoxy protons), 3.33 [N$^+$(CH$_3$)$_2$], 3.75 (H$_2$C—H$_2$C—N$^+$—CH$_2$—CH$_2$—), 5.29-5,54 (CH=CH—), 7.52 (NH—CO);

$^{13}$C NMR (200 MHz, CDCl$_3$): δ=13.91 (CH$_3$), 33.62 (—CH$_2$—NH—CO—), 36.19 (—NH—CO—CH$_2$—), 52.37 (N$^+$(CH$_3$)$_2$), 56.49 and 57.13 (epoxy carbons), 63.24 (—H$_2$C—N—CH$_2$), 123.79 and 132.47 (CH=CH), 174.60 (NH—CO—).

Derivative 13 was also prepared in two steps from Precursor 10 by first mono-methylating the free amino group of Precursor 10, followed by quaternization of the methylated precursor with methyl iodide, as follows:

Precursor 10 (6.56 g, 10 mmol) was dissolved in 30 ml of dry toluene at 65° C. To this solution anhydrous potassium carbonate (0.69 g, 5 mmol) and methyl iodide (1.42 g,10 mmol) were added and the reaction mixture was stirred at 65° C. for 15 hours. The potassium iodide was filtered and the residue was dissolved in chloroform and washed with water 3-4 times. The organic phase was separated, dried over Na$_2$SO$_4$ and evaporated under reduced pressure. The diamide mixture containing tertiary amine group was purified by column chromatography using acetone:methanol 1:1 v/v as the eluent to give 70% yield of the mono-methylated product.

IR (KBr, cm$^{-1}$): 3330, 1640, 1550(secondary amide), 2780 (tertiary amine), 840, 820(epoxy group);

$^1$H NMR (500 MHz, CDCl$_3$): δ=0.87-0.9 (CH$_3$), 2.23 (—N—CH3), (2.47-2.50 (CH$_2$—N—CH$_2$), 2.89-2.91 (epoxy protons), 3.3-3.33 (CH$_2$—CH$_2$—N—CH$_2$—CH$_2$—), 5.28-5.23(CH=CH), 6.10 (NH—CO);

$^{13}$C NMR (500 MHz, CDCl$_3$): δ=13.99 (CH$_3$), 42.28 (N—CH$_3$), 56.53 (CH$_2$—N—CH$_2$), 57.22(epoxy carbons), 124.34 and 132.54 (CH=CH), 173.48 (NH—CO).

The mono-methylated form of Precursor 10 was dissolved in 50 ml of dry acetone at 60° C. and a threefold excess of methyl iodide (4.26 g, 30 mmol) in 50 ml of dry acetone was added during 10 minutes. The reaction mixture was stirred and heated at 60° C. for 2 h. After cooling and removal of the solvent under reduced pressure, diethyl ether was added to the residue and the precipitate was then filtered to give a white powder of Derivative 13 (60% yield) having a melting point of 63-65° C. The amount of iodide ion determined by argentometric titration was 12.2%.

The IR and NMR spectra were identical with the compound obtained in one step by exhaustive methylation of Precursor 10, as was shown hereinabove.

Example 25

Preparation of Amphiphilic Derivative 14

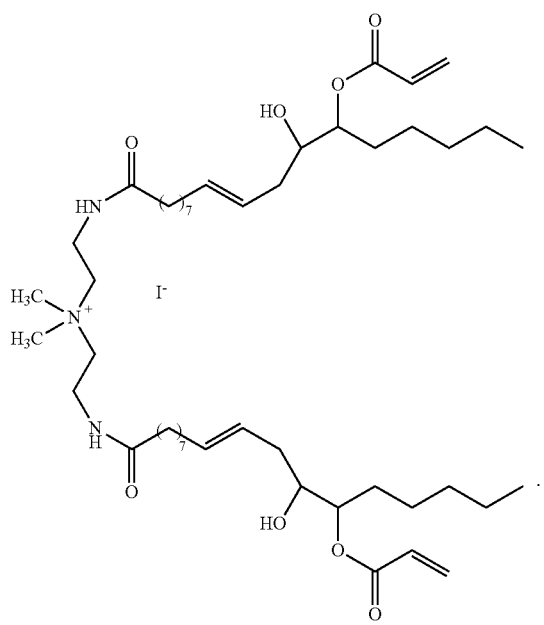

Derivative 14 was prepared by reacting Derivative 13 with acrylic acid according to the procedure described in Example 1(a), as shown in Scheme 12.

Example 26

Preparation of amphiphilic 11-(3-pentyloxiranyl)undec-9-enoic acid [12-(2-{2-[11-(3-pentyloxiranyl)undec-9-enoylamino]ethylamino}ethylamino)ethyl]amide (Derivative 15)

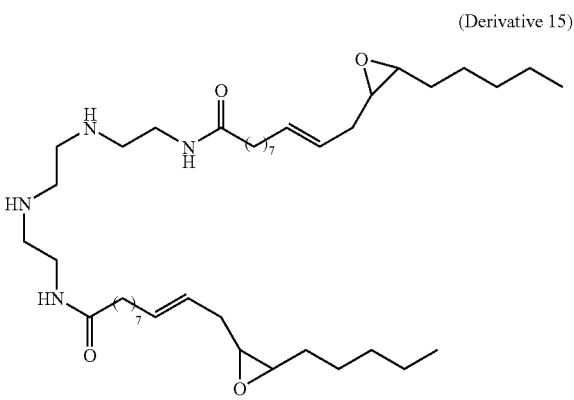

Derivative 15 was prepared from triethylene tetramine and trivernolin as shown in Scheme 13, as follows:

A mixture of 9.26 g trivernolin (10 mmol of vernonia oil based on a molecular weight of 926) and 2.92 g (20mmol) triethylene tetramine was heated at 60° C. for 7 h. The reaction mixture was triturated with 200 ml diethyl ether in order to remove the unreacted starting material. The precipitate obtained was filtered, washed with diethyl ether and the product, 2.02 g in weight, was isolated by column chromatography with chloroform: methanol 1:9 v/v as the eluent.

Elemental analysis: Calculated for C$_{42}$H$_{78}$O$_4$N$_4$ (MW=702): N, 7.98%; Found 7.2%.

The IR and NMR spectra confirmed the structure of the molecule.

Example 27

Preparation of amphiphilic 11-(3-pentyloxiranyl)-undec-9-enoic acid 2-aminoethyl amide Trivial name: N-(2-aminoethyl)vernolamide (Derivative 16)

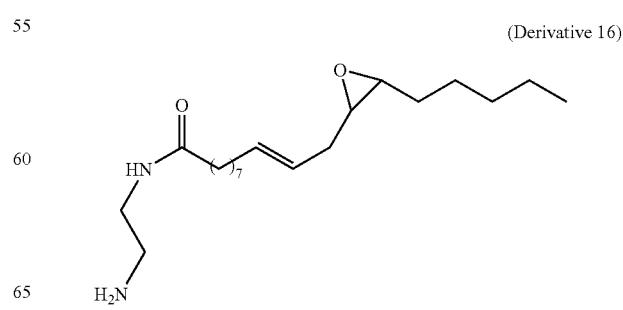

Derivative 16 was prepared by the reaction of methyl vernolate with 3 equivalents of ethylenediamine as shown in Scheme 14 and as follows:

A solution of 3.1 g (0.01 mol) methyl vernolate and 1.8 g (0.03 mol) 1,2-ethylenediamine was heated at 40° C. for 5 minutes. Then 0.6 ml of a 2N solution of sodium methoxide (0.0648 g, 0.012 mol) in absolute methanol was added and the reaction mixture was heated at 40° C. for 3 hours. TLC showed that no more methyl vernolate was present in the reaction mixture. Thus, the reaction mixture was dissolved in chloroform and washed with water (×3 times). After separation of the organic layer, it was dried over anhydrous sodium sulfate and the solvent was evaporated under reduced pressure. The crude product was purified by column chromatography on silica gel 60, eluted chloroform containing increasing amounts of methanol ($R_f$=0.17). Derivative 16 was obtained in 67% yield (2.09 g) and exhibited a melting point of 115-116° C. HPLC of Derivative 16 showed one peak with a retention time of 4.54 minutes.

Mp=116-117° C.;

IR (KBr pellet) $cm^{-1}$: 3330 (NH), 1630 and 1540 (amide I and II bands), 820 and 840 (epoxy groups).

$^1$H NMR (200 MHz, $CDCl_3$): δ=0.9 (3 H, $CH_3$), 1.30 (m, $(CH_2)_n$) 1.67 (2H, $CH_2NH_2$), 2.02 (2H, CH=CH—$CH_2$ epoxy), 2.22 (2H, —NH—CO—$CH_2$) 2.83 (2H, —C$\underline{H}_2$—$NH_2$), 2.93 (2H, epoxy protons), 3.34 (2H, —NH—C$\underline{H}_2$) 5.46 (2H, CH=CH), 6.12 (1H, CO—NH);

$^{13}$C NMR ($CDCl_3$): δ=13.98 ($CH_3$), 22.57 ($CH_3$—$CH_2$), 36.78 (—$CH_2$—CO—NH), 41.32 (CONH—$CH_2$), 41.71 (CONH—$\underline{C}H_2$—$CH$—$NH_2$), 123.86 and 132.53 (CH=CH), 173.46 ($\underline{C}O$—NH);

Elemental Analysis: calculated N % 8.28; found 8.80.

Example 28

Preparation of amphiphilic 11-(3-pentyloxiranyl)undec-9-enoic acid (3-aminopropyl)amide

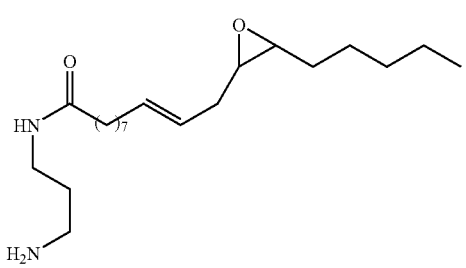

(Derivative 17)

Derivative 17 was prepared from methyl vernolate and 1,3-diaminopropane according to the procedure described in Example 1(f) and shown in Scheme 14.

Mp=114-115° C.;

Elemental Analysis: calculated N % 7.95, found 7.90.

Example 29

Preparation of amphiphilic 11-(3-pentyloxiranyl)undec-9-enoic acid (3-aminobutyl)amide

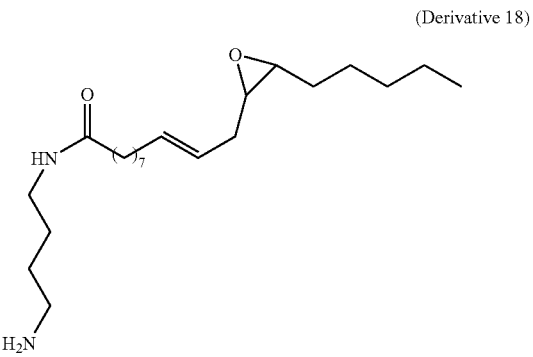

(Derivative 18)

Derivative 18 was prepared from methyl vernolate and 1,4-diaminobutane according to the procedure described in Example 1(f) and shown in Scheme 14.

Mp=118-119° C.;

Elemental Analysis: calculated N % 7.65, found 7.53.

Example 30

Preparation of amphiphilic 11-(3-pentyloxiranyl)undec-9-enoic acid (3-aminohexyl)amide

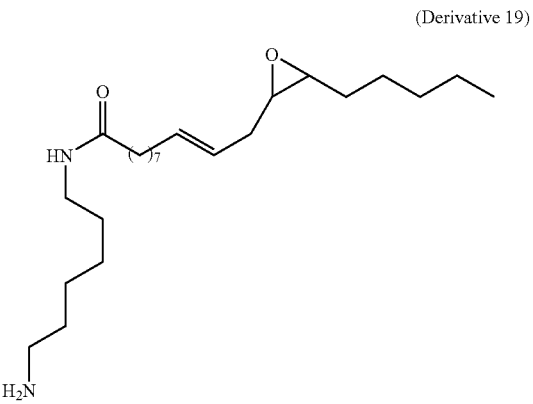

(Derivative 19)

Derivative 19 was prepared from methyl vernolate and 1,6-diaminohexane according to the procedure described in Example 1(f) and shown in Scheme 14.

Mp=118-119° C.;

Elemental analysis: N % 7.11, found 7.08%.

Example 31

Preparation of Derivatives 20 and 21

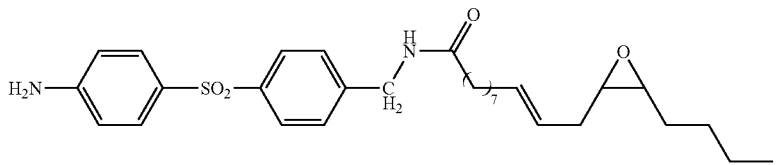

Derivative 20 was prepared in one step from methyl vernolate and p-aminophenyl-p-aminomethylphenylsulfone [Wenner, 1957] as shown in Scheme 15, as follows:

A solution of methyl vernolate (3.1 g, 10 mmol) and p-aminophenyl-p-aminomethyphenylsulfone (2.62 g, 10 mmol) in 20 ml dry methanol was heated at 50° C. for 10 minutes. To this solution, 0.6 ml of a 2N sodium methoxide solution in absolute methanol was added and the reaction mixture was heated at 50° C. for 3 h. The reaction mixture was dissolved in chloroform and washed with water. The organic layer was dried and the solvent removed under reduced pressure. The pure Derivative 20 was separated from the residue by column chromatography using chloroform with increasing amounts of methanol as the eluent.

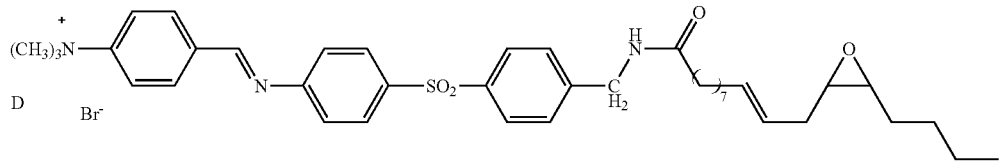

Derivative 21 was obtained from Derivative 20 as shown in Scheme 15 as follows:

The condensation of the Derivative 20 with (p-formylphenyl) trimethyl ammonium bromide [Kunitake and Okahata, 1980] was achieved in refluxing ethanol for about 2 h.

Example 32

Preparation of Amphiphilic Derivative 22

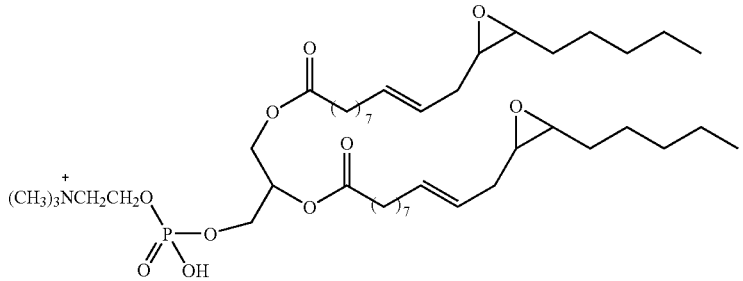

Derivative 22 is prepared in two steps according to the procedure of Hirt and Berchtold [Hirt and Berchtold, 1958].

The phosphoccholine moiety was introduced into the triglyceride Precursor 11 by phosphorylation with (2-bromoethyl)phosphodichloridate in toluene, followed by hydrolysis, thus obtaining Precursor 12. Precursor 12 was then treated with trimethyl amine according to the procedure described in Example 1(e), to give Derivative 22, as shown in Scheme 16.

Alternative procedures with other useful phosphorylating agents were employed for vernonia diglycerides, as described by Eibel and Nicksh [Eibel and Nicksh, 1978; also Hansen et al, 1982]. Phosphocholine analogues with head groups containing additional methylene groups between the phosphorous and the nitrogen functionalities or with N-alkyl groups larger than N-methyl were prepared according to Ali and Bittman [Ali and Bittman, 1989].

Example 33

Preparation of 13-(2-chloroacetoxy)-12-hydroxyoctadec-9-enoic acid 2,3-bis-[13-(2-chloroacetoxy)-12-hydroxyoctadec-9-enoyloxy]propylester (Precursor 13)

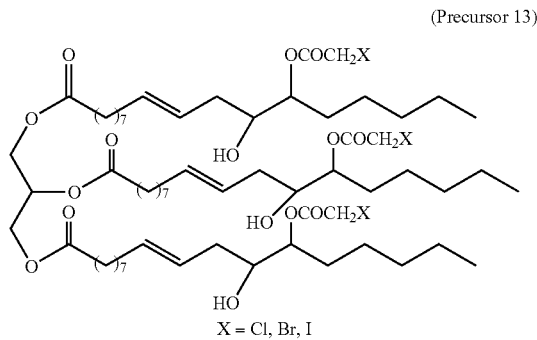

X = Cl, Br, I

Precursor 13 was prepared from trivernolin as shown in Scheme 17, as follows:

A mixture of 13.23 g (0.01 mol) vernonia oil (contains 70% of vemolic acid by gas chromatography) and chloroacetic acid (3.69 g, 0.039 mol) was dissolved in 50 ml toluene and the solution was heated at 90° C. for 22 hours. The course of the reaction was monitored by TLC. After cooling to room temperature, diethyl ether was added and the reaction mixture was first washed with a 5% sodium bicarbonate solution (×2 times), and with water (×4 times) and then dried over sodium sulfate. The solvent was removed under reduced pressure to yield 13.83 g (80% yield) of the tris-chloroacetoxy product designated Precursor 13.

IR (neat, cm$^{-1}$): 3450 (OH), 1280 and 1300 (chloroacetate group), and 780 (C—Cl);
$^1$H NMR (500 MHz, CDCl$_3$): δ=0.78 (CH$_2$), 3.59 (—CH—OH), 4.01-4.03 (—OCO—CH$_2$—Cl), $\overline{4}$.07 and 4.20 ($\overline{—CH_2}$—OCO), 4.80-4.86 (—CH$\overline{—}$O—CO—CH$_2$Cl), 5.17 (—O$\overline{CO}$—CH$_2$—CH—OCO—), 5.24-5.47 (—CH═CH—);
$^{13}$C NMR (500 MHz, CDCl$_3$): δ=13.90 (CH$_3$), 40.90 (—CH$_2$—Cl), 62.02 (CH—CH$_2$—OCO), 68.$\overline{82}$ (—OCO—$\overline{CH_2}$—CH—O—CO—), $\overline{71}$.86 and 72.19 (—CH—OH), 78.16 ($\overline{—}$CH—OCOCH$_2$—Cl), 123.27 and 123.$\overline{96}$; 127.82 and 128.$\overline{00}$; 129.92 and 130.12; 133.5 and 133.65 (—CH═CH—), 166.94 and 167.09 (—CH—O—CO—CH$_2$Cl), $\overline{172}$.76 and 173.18 (—CO—O—CH$_2$—CH) and (—OCO—CH$_2$—CH—O—CO);

Elemental Analysis: Calculated for C$_{63}$H$_{107}$O$_{15}$Cl$_3$ (M.W.=1209.5): Cl, 8.8% (Cl for tris-chloroacetate of vernonia oil=8.80×0.7=6.16%). Found: Cl, 5.635%.

Similarly to Precursor 13 prepared hereinabove, the trisbromoacetoxy was prepared. A solution of 9.26 g (0.01 mol) of trivernolin and 5.42 g (0.01 mol) bromoacetic acid in 40 ml toluene was heated at 90° C. for 24 hours. After cooling to room temperature, diethyl ether was added and the reaction mixture was dissolved in chloroform and washed twice with a 5% solution of sodium bicarbonate, and then several times with water. After phase separation, the organic layer was dried over sodium sulfate and the solvent was removed under reduced pressure to yield 11.2 g (85% yield) of the trisbromoacetoxy product. The product contained 0.2% of epoxy groups.

Elemental analysis: calculated for C$_{63}$H$_{107}$Br$_3$O$_{15}$ (MW=1343) Br, 17.85%; Found Br, 17.6%.
IR (neat, cm$^{-1}$): 3450 (OH), 1280 (bromoacetate group);
$^1$H NMR (200 MHz, CDCl$_3$): δ=3.81-3.90 (—CH—Br);
$^{13}$C NMR (500 MHz, CDCl$_3$): δ=25.86 (—CH$_2$—Br).

The tris-iodoacetoxy precursor was also prepared according to this procedure, by utilizing iodoacetic acid.

Example 34

Preparation of Amphiphilic Derivative 23

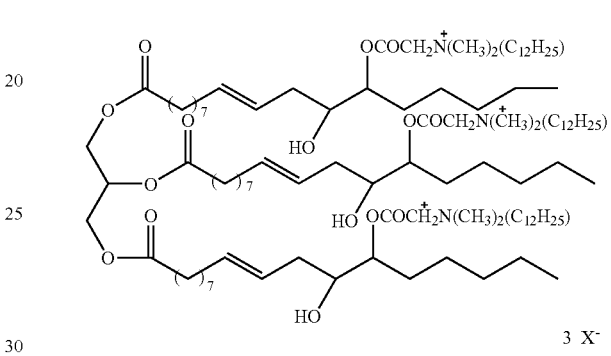

3 X$^-$

Derivative 23 was prepared from Precursor 13 as shown in Scheme 17, as follows:

The crude tris-chloroacetoxy Precursor 13 (1.73 g containing 1.21 g of tris-chloroacetoxy of trivernolin, 1 mmol) and N,N-dimethyldodecylamine (0.64 g, 3 mmol) were refluxed in 3.5 ml of acetone for 3 hours. The solvent was removed under reduced pressure and the residue was dried under vacuum at room temperature to give Derivative 23 as viscous oil. The chloride ion amount of this product as determined by argentometric titration was equal to 3.49% (theoretical 4.03%). Yield of quaternization was equal to 86.6

IR (neat, cm$^{-1}$): 3300, 1740, 1160, 1235, and 1200;
$^1$H NMR (500 MHz, CDCl$_3$): δ=0.79-0.81 (CH$_3$), 3.43 and 3.45 (CH$_2$—N(CH$_3$)$_2$—CH$_2$), 3.52 (—$\overline{N}$(CH$_3$)$_2$—CH$_2$—CH$_2$), 3.66 (—CH—OH), 4.6 (OCO—C$\overline{H_2}$—N(CH$_3$)$_2$—), 4.07 and 4.$\overline{22}$ (—CH$_2$—O—CO—), 4.83-$\overline{4.86}$ (—CH—O—CO—CH$_2$—N$\overline{(CH_3)_2}$), 5.20-5.42 (—OCO—CH$_2$—CH—O—CO and CH═CH—);
$^{13}$C NMR (500 MHz, CDCl$_3$): δ=13.$\overline{91}$, ($\overline{CH}_3$), 51.29 and 51.64 (CH$_2$—N(CH$_3$)$_2$CH$_2$), 61.42 N(C$\overline{H_3}$)$_2$CH$_2$—CH$_2$), 61.86 (CH—$\overline{CH}_2$—O—CO), 64.54 (—CO—CH$_2$—N(CH$_3$)$_2$—), 68.65 (—O—CO—CH$_2$—$\overline{CH}$—O—CO—), 71.20 and 71.67 (—CH—OH), 79.56 (—$\overline{CH}$—O—CO—CH$_2$—N(CH$_3$)$_2$—), 12$\overline{3}$.01 and 133.14 (—$\overline{CH}$═CH—), 164.59 and 164.77 (—CH—O—$\overline{CO}$—$\overline{CH}_2$—N(CH$_3$)$_2$), 172.61 and 173.01 (—$\overline{CO}$—O—CH$_2$—CH and —OCO—CH$_2$—CH—O—$\overline{CO}$—);

Elemental Analysis: Calculated for C$_{105}$H$_{200}$O$_{15}$N$_3$Cl$_3$ (M.W.=1848.5): Cl, 5.76; N, 2.27. (70% of product): Cl=5.76×0.7=4.03%; N=2.27×0.7=1.59%. Found: Cl, 4.0; N, 1.85.

Alternatively, the synthesis Derivative 23 was carried out in iso-propanol as the solvent at 80° C. for 4 hours: found % Cl-3.38% (Calc. 4.03%), and in toluene at 76° C. for 72 hours:

found % Cl-3.30%. The yield was 84% and 82%, respectively. The IR and NMR spectra were identical to those above.

Derivative 23 is also obtained from the tris-bromoacetoxy precursor, under conditions identical to those described hereinabove.

Example 35

Preparation of Amphiphilic Derivative 24

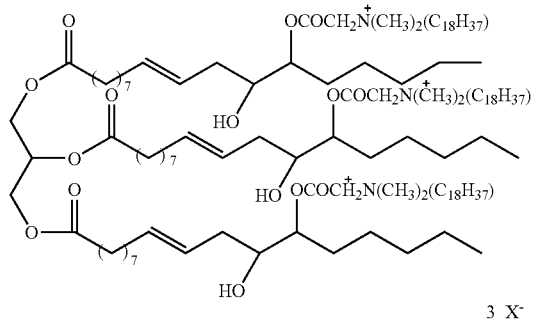

Derivative 24 was prepared from Precursor 13 as shown in Scheme 17, as follows:

The crude tris-iodoacetoxy, Precursor 13, (2.11 g, containing 1.48 g of tris-iodoacetoxy of trivernolin, 1 mmol) and N,N,N-dimethyloctadecylamine (0.89 g, 3 mmol) were refluxed in 4.5 ml of acetone for 3 hours. The solvent was removed under reduced pressure and the residue was dried under vacuum at room temperature to give Derivative 24 as a viscous liquid. The iodide ion amount of this product, as determined by argentometric titration, was equal to 10.8% (theoretical value is 11.2%). Yield of quaternization was equal to 96.4%.

Example 36

Preparation of Amphiphilic Derivative 25

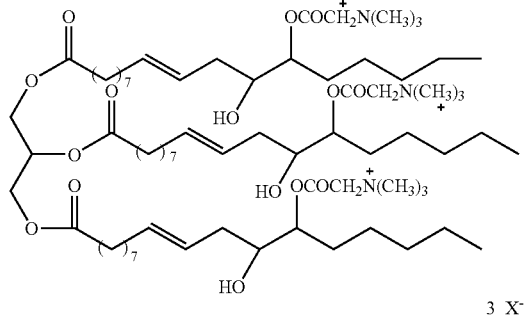

Derivative 25 was prepared from Precursor 13 as shown in Scheme 17, as follows:

A solution of the crude tris-iodoacetoxy Precursor 13 (21.1 g containing 14.84 g of tris-iodoacetoxy of trivernolin, 10 mmol) in 25 ml dry acetone was treated with 9 ml of a 25% solution of N,N,N-trimethylamine in methanol. This solution was placed in a 100 ml Pyrex reagent bottle that was closed with a tightly fitting rubber stopper and was allowed to stand at room temperature for 24 hours. The solvent was evaporated under reduced pressure to give Derivative 25. The amount of iodide ions in the product obtained was found equal to 16%.

Example 37

Preparation of 13-azido-12-hydroxyoctadec-9-enoic acid 2,3-bis-(13-azido-12-hydroxyoctadec-9-enoyloxy)propyl ester (Precursor 14)

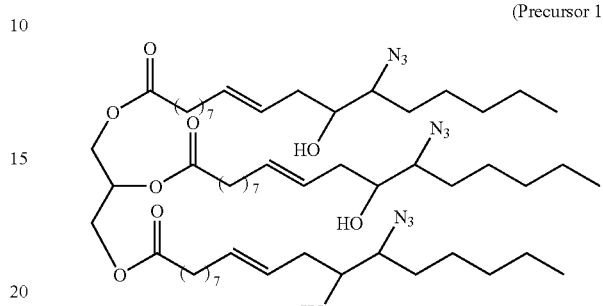

Precursor 14 as shown in Scheme 18 was prepared according to Example 1(b) by three different methods from vernonia oil or from purified trivernolin and sodium azide.

Example 38

Preparation of amphiphilic 13-amino-12-hydroxyoctadec-9-enoic acid 2,3-bis-(13-amino-12-hydroxyoctadec-9-enoyloxy)propyl ester (Derivative 26)

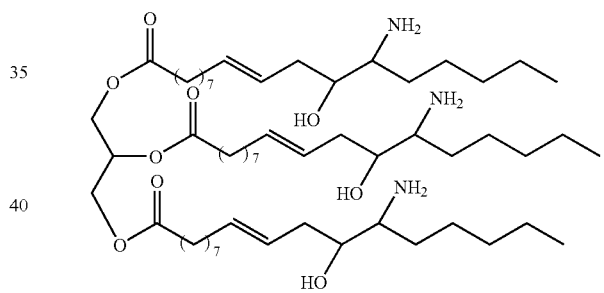

Derivative 26 was prepared, as shown in Scheme 18 by the reduction of Precursor 14, according to procedures described in Example 3.

Example 39

Preparation of Amphiphilic Derivative 27

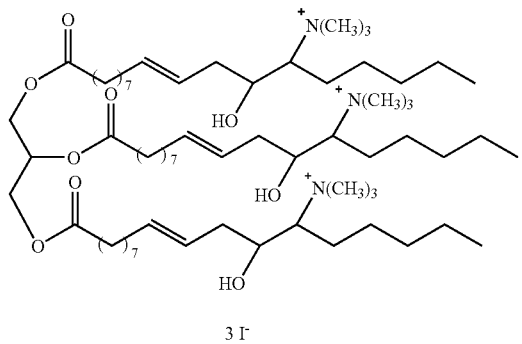

Derivative 27 was prepared, as shown in Scheme 18, by exhaustive methylation of Derivative 26 with methyl iodide, according to the procedure described in Example 24.

Example 40

Preparation of 11-bromo-11(3-pentyloxiranyl)undec-9-enoic acid methyl ether

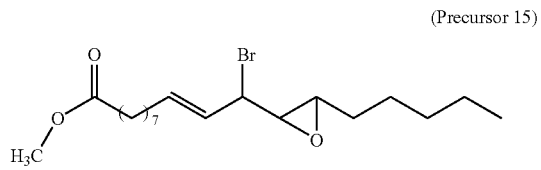

(Precursor 15)

Precursor 15 was prepared by selective bromination of methyl vernolate as shown in Scheme 19, as follows:

A solution of 400 mg (1.3 mmol) of the methyl vernolate and 235 mg (1.3 mmol) of N-bromosuccinimide (NBS) in carbon tetrachloride (15 ml) was refluxed under a lamp (300 W) for 3 h. Filtration of the solid succinimide and evaporation of the solvent gave Precursor 15 (430 mg). The mixture was purified by column chromatography (140 g of $SiO_2$) with a hexane:ether 10:1 solution as the eluent thus obtaining 60% of the desired Precursor 15.

IR $cm^{-1}$: 1730 (ester carbonyl), 850, 820 (epoxy group).

$^1$H-NMR (δ, ppm): 0.91 (3H at C-18, ), 2.28 (2 H at C-2.), 3.02 (2H at C-12 and C-13, epoxy protons), 3.67 (3H, $OCH_3$), 4.49 and 4.67 (H at C-11, CHBr), 5.90 (2H at C-9 and C-10, olefinic protons);

Elemental analysis: Calculated for $C_{19}H_{33}BrO_3$: Br, 20.56%, found 20.4%.

Example 41

Preparation of 11-bromo-13-(2-chloroacetoxy)-12-hydroxyoctadec-9-enoic acid methyl ester

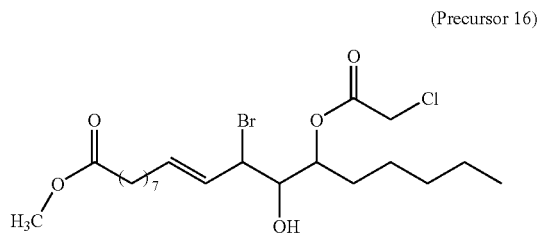

(Precursor 16)

Precursor 16 was prepared from Precursor 15 by haloacetic acid epoxide ring opening as shown in Scheme 19, as follows:

A mixture of 3.89 (10 mmol) of 11-bromo methyl vernolate and chloroacetic acid (1.13 g, 0.012 mol) in 25 ml toluene was heated for 14 hours at 90° C. After cooling diethyl ether was added to the reaction mixture and the organic phase was washed with water, separated, dried and the solvent evaporated. The mixture of products obtained was purified by column chromatography with hexane:diethyl ether (1:1 v/v) as eluent.

$^1$H NMR (200 MHz, $CDCl_3$): δ=4.09 ($CH_2$—Cl), 4.67 (C$H_2$—Br), 4.93 (C$H$—O—CO—$CH_2$—Cl);

Elemental analysis: Calculated for $C_{21}H_{36}O_5BrCl$ (MW=483.5): Br, 16.52%; Cl, 7.34%, found: Br, 16.35%; Cl, 7.2%.

Example 42

Preparation of Derivative 28

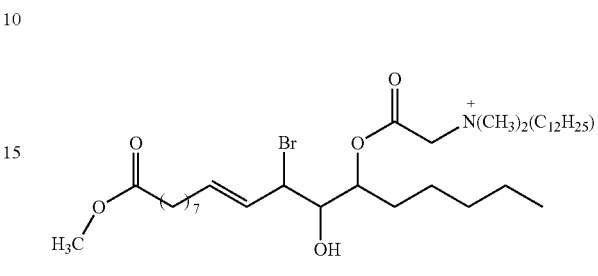

Derivative 28 was prepared from Precursor 16 and dimethyldodecylamine as shown in Scheme 19, as follows:

A mixture of 4.43 g (10 mmol) of the Precursor 16 and dimethyldodecylamine (2.13 g, 10 mmol) in 10 ml iso-propanol was stirred and heated for 3 h at 80° C. The solvent was removed under reduced pressure to give 6.7 g of the ammonium salt. The yield of the quaternization was 90%.

$^1$H NMR (200 MHz, $CDCl_3$): δ=3.45 [$N^+(CH_3)$], 3.54 [$N^+(CH_3)$—$CH_2$—$CH_2$], 4.71 [—O—CO—$CH_2$—$N^+(CH_3)$];

Elemental analysis: Calculated for $C_{35}H_{67}NO_5BrCl$ (MW=696.5) $Cl^-$, 5.10%: Found: (argentometric titration) Cl, 4.6%.

Example 43

Preparation of Precursor 17

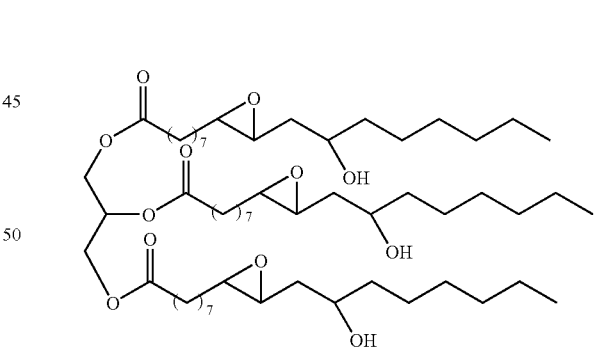

Precursor 17 was prepared in one step from castor oil as shown in Scheme 20, as follows:

To a mixture of castor oil 9.24 g (10 mmol) and 6.8 g $NaHCO_3$ in 100 ml benzene, m-chloroperbenzoic acid (7.6 g, 33 )mmol) was added slowly during 1 hour at 15-17° C. with vigorous stirring. The mixture was stirred for an additional 1.5 hour at room temperature and then it was treated with 10% sodium sulfite in a separatory finnel until a negative test with starch-iodide paper was obtained. The organic layer was washed with a 5% sodium bicarbonate solution and then with water. The solvent was removed under reduced pressure to give 8.46 g (90% yield) of epoxidized castor oil Precursor 17 with 11.8% amount of epoxy groups (calculated 13.4%).

Example 44

Preparation of Precursor 18

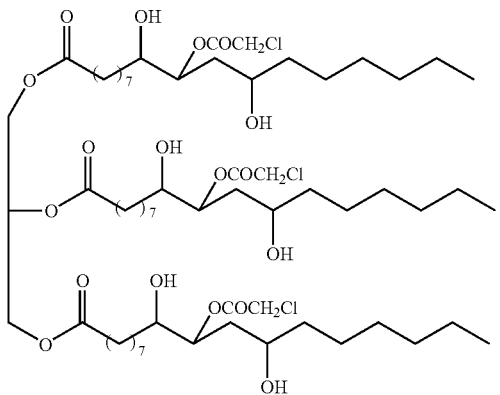

Precursor 18 was prepared from Precursor 17 as shown in Scheme 20, as follows:

Epoxidized castor oil, Precursor 17, 10.4 g (10 mmol) and 3.68 g (39 mmol) of chloroacetic acid were reacted as described in Example 33. The chloroacetate Precursor 18 was obtained in 90% yield (11 g).

Example 45

Preparation of Amphiphilic Derivative 29

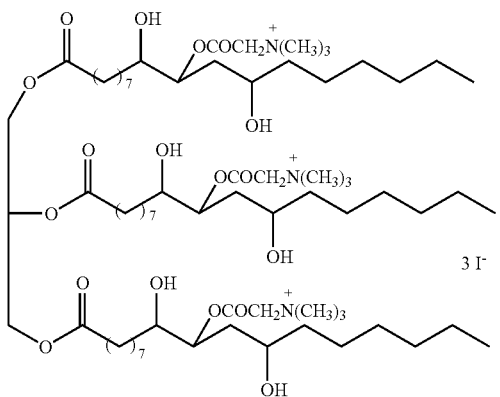

Derivative 29 was prepared from Precursor 18 by the addition of trimethyl amine according to the procedure described in Example 1(e) and as shown in Scheme 20.

Example 46

Preparation of Vesicles

Two main methods were used to prepare the vesicles: In method (1), 100-200 µl of the amphiphilic derivative dissolved in methanol was injected into 2-4 ml of an aqueous solution which contained the compound to be encapsulated. The mixture was sonicated in a bath sonicator (Branson 2510) for a short (1,2,5,10 min) or long (60 min) period, depending on the desired vesicle size (dozen or hundred nanometer) and uniformity. In method (2), the amphiphilic derivative dissolved in methanol (250-1000 µl) was added to a 50-ml round-bottom flask, the solvent was removed under reduced pressure by a rotary evaporator and a thin oily film was formed on the flask bottom. An aqueous solution containing the compound desired to encapsulate (1-4 ml) was added to the flask and the mixture was sonicated in a bath sonicator for 1-5 min at 60° C.

Figure 2:
FIG. 2: TEM photograph nanovesicles of Derivative 2 encapsulating water, showing the internal structure of the vesicles. The TEM experiment was carried out using negative staining technique, employing a 1% uranyl acetate solution.
Figure 3:
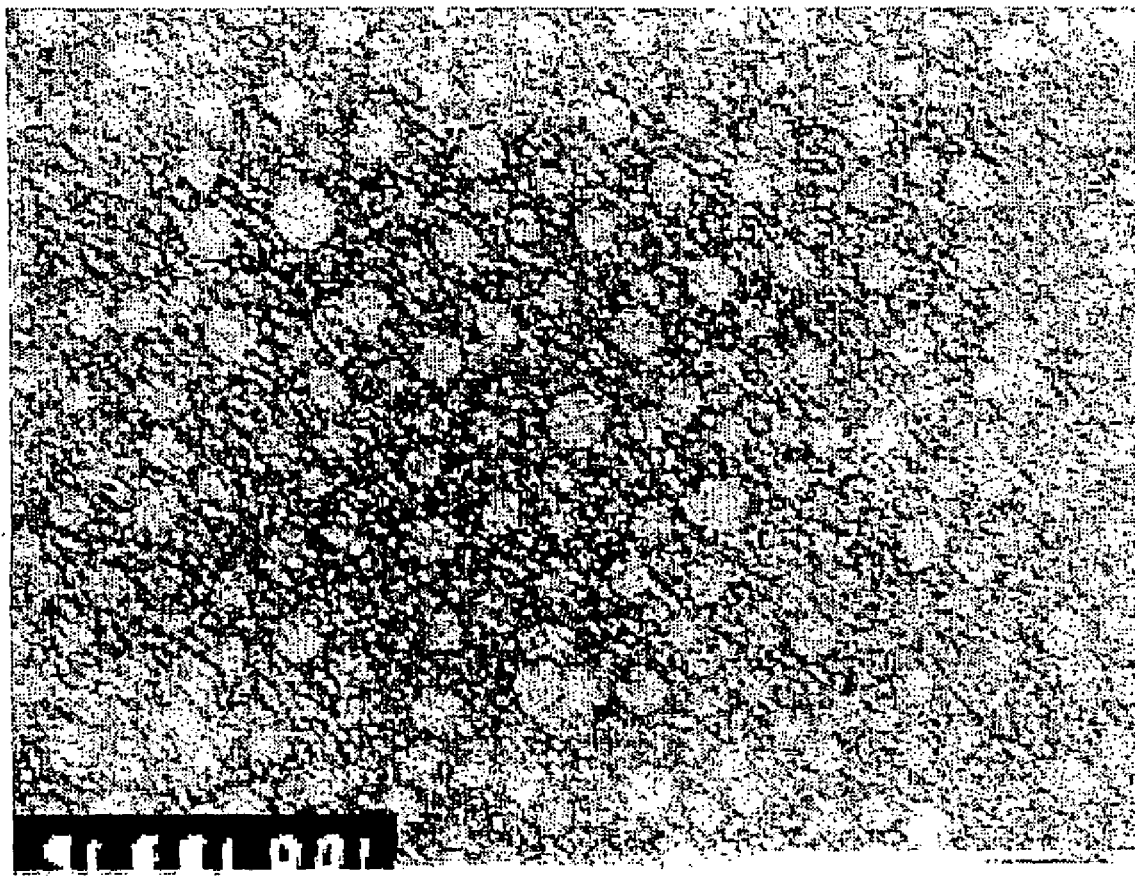
FIG. 3: TEM photograph nanovesicles of Derivative 10.
Figure 4:
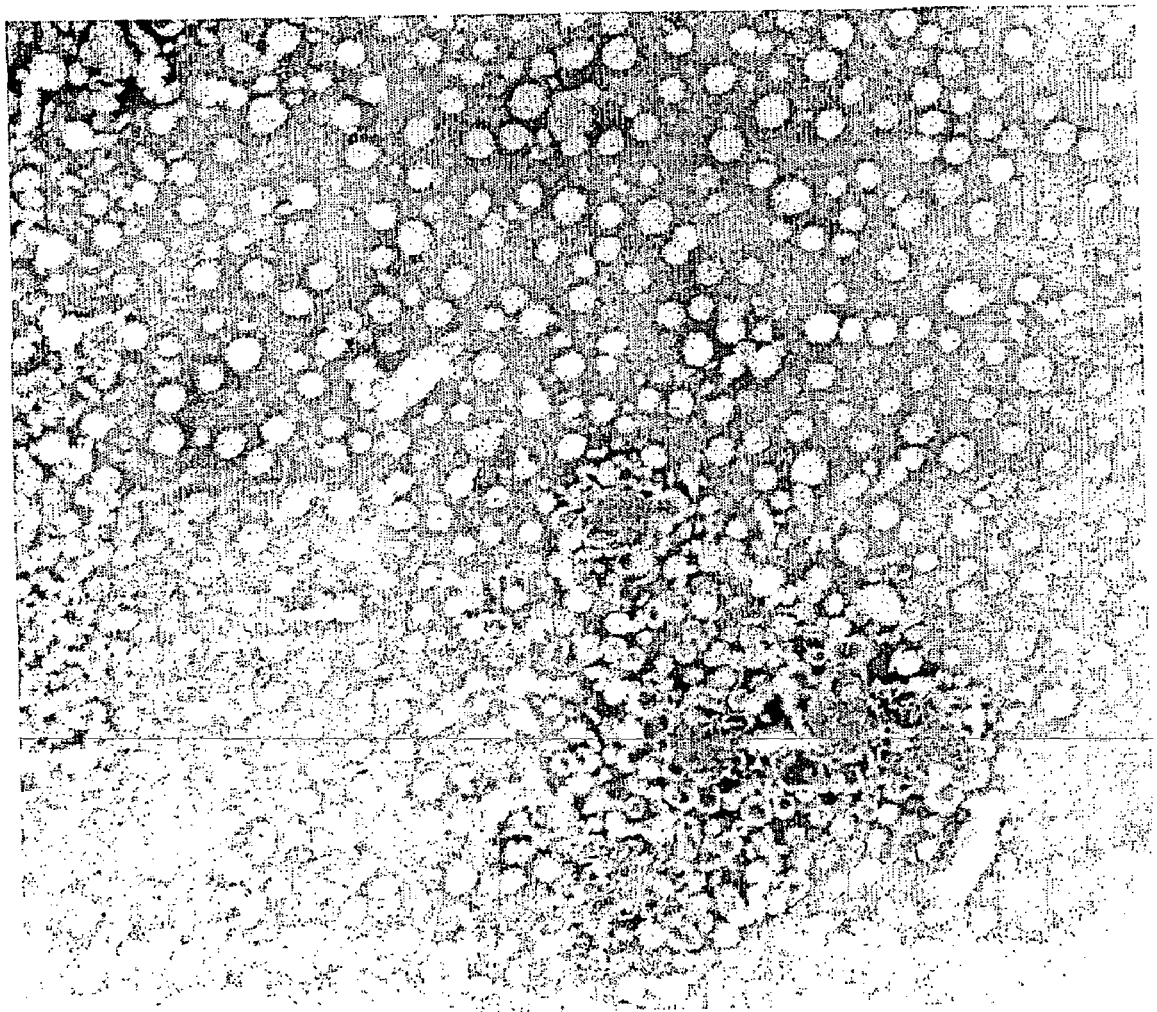
FIG. 4: TEM photograph of L-alpha-phosphatidyl choline (L-alpha-Lecithin) liposomes. The formed liposomes were used as positive control for the comparison with the vesicles prepared from the various vernonia oil derivatives.

TEM (transmission electron microscopy) experiments were carried out using negative staining technique, employing saturated uranyl acetate solution (after centrifuge). The grid was immersed in the vesicle solution for 1.5 minutes and then was stained in the uranyl acetate solution for 1.5 min. The grid (300 mesh copper Formvar/carbon) was then dried at room temperature on filter paper. FIG. 1 shows a TEM photo of nanovesicles prepared from Derivative 2 encapsulating 2% uranyl acetate. The vesicles prepared were of different sizes ranging from 10 to 100 nm. FIG. 2 shows a TEM photo of nanovesicles of Derivative 2 wherein the internal structure of the vesicle is shown. Uranyl acetate was used in this picture for the purpose of staining only. The vesicles shown in FIG. 2 contain no uranyl acetate in their cavity. FIG. 3 shows a TEM picture of nanovesicles prepared from Derivative 10 and stained with uranyl acetate. FIG. 4 shows the triglyceride phosphatidylcholine liposome, which served as a positive control. Derivatives of vernonia oil and the solvent used for vesicle preparation served as a negative controls and showed no vesicle formation (not shown).

The TEM pictures of vesicles of the vernonia oil Derivative 2 (FIG. 1 and 2) and of Derivative 10 (FIG. 3) along with the picture shown for the control triglyceride phosphatidylcholine liposome (FIG. 4) demonstrated the possibility of forming nonasized vesicles from the amphiphilic derivatives of the invention such as Derivative 2.

For preparation of samples for AFM (atomic force microscopy) experiments, 10 µl of the liposome solution were placed on a freshly cleaved mica surface. After 2 minutes, the surface was rinsed with 1-2 ml water, dried with a stream of nitrogen and further dried in a desiccator.

For confocal experiments, to the oily film on the flask bottom, $6.68 \times 10^{-6}$ M rhodamine (tetramethylrhodamine-5-2'-deoxy-uridine-5'-triphosphate) solution or $2 \times 10^{-6}$ g/ml dichlorofluorescein solution were added and the mixture was sonicated in a bath sonicator for 1-5 min. DNA plasmid (ng/µl) stained in rhodamine or FITC; ULSIS Alexa Fluor ® 488 Nucleic Acid Labeling Kit) was added to a solution of 20 µl of vesicles, the mixture was spread on a microscope slide and dried at room temperature.

In order to evaluate the vesicle stability, the solutions were left at room temperature and the size and structure of the liposomes were examined by means of TEM once in a week during 59 days.

TABLE 1

Summary of the stability study of three nanoliposomes produced from Derivatives 23, 2 and the Cu-complex of Derivative 15.

| | Days from Initiation of the Study | | | | | | |
|---|---|---|---|---|---|---|---|
| | 0 | 10 | 14 | 21 | 28 | 45 | 59 |
| Derivative 23 | +* | + | + | + | + | + | + |
| Derivative 2 | + | + | + | ± | ± | − | |
| Cu-Derivative 15 | + | + | + | + | + | + | |

The symbol (+*) represents intact liposomes, (±) represent liposomes that partially lost vesicle shape, and the symbol (−) represents liposomes that completely lost their vesicle shape.

Figure 5:
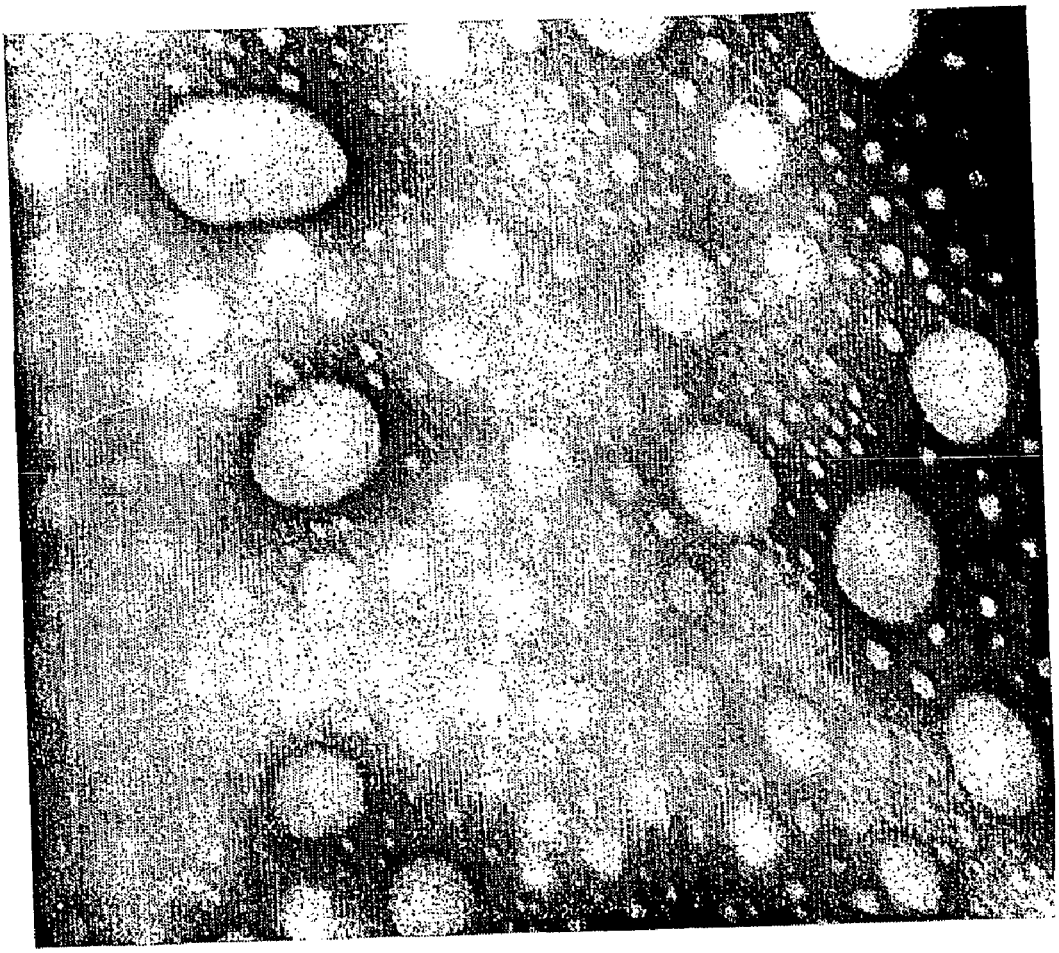
FIG. 5: TEM photograph of 21-day old vesicles of Derivative 23 left at room temperature. Twenty-one days after their preparation, Derivative 23 vesicles remained in their original shape and with their membrane intact. The whole, intact structures and cavities are clearly visible.
Figure 6:
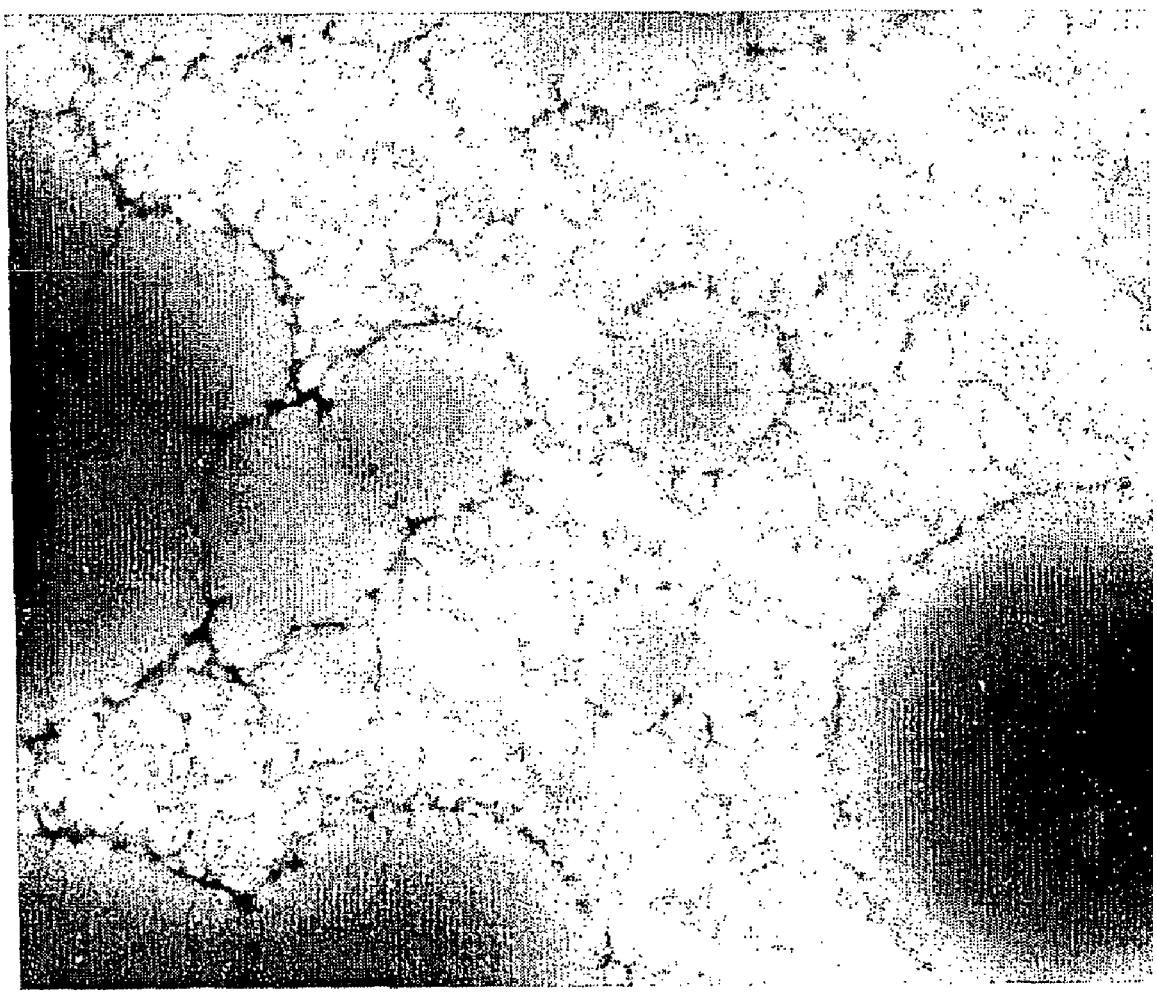
FIG. 6: TEM picture of 59-day old nanovesicles of Derivative 23. The photograph clearly shows fully structured and nicely shaped vesicles even after 59 days of storage at room temperature.

Ten days after the initiation of the study, some clusterization and aggregation of liposomes could be observed in the three derivatives. After 21 days, Derivative 2 vesicles seemed to partially lose their membrane integrity and after 45 days only oily spots appeared in place of the Derivative 2 vesicles. At the same time, vesicles could still appear in the preparation of the Cu-complex of Derivative 15 that also started to partially lose their integrity. Derivative 23 vesicles remained in their original shape even after 59 days. FIG. 5 shows the TEM picture of Derivative 23 vesicles 21 days after preparation. The vesicles appear whole with no damage to their membrane integrity. FIG. 6 is the picture of the Derivative 23 vesicles, showing a different area of the slide, illustrating the integrity of the vesicles 59 days from the time of their preparation.

Example 47

Encapsulation

A solution of amphiphilic Derivative 2 or Derivative 23 (0.1 g) in 1 ml ethanol was mixed with 1 ml of a 2% solution of uranyl acetate in deionized water (uranyl acetate is electron-opaque and can be visualized by electron microscopy in the core of the vesicles when it is encapsulated). The mixture was sonicated for 20 seconds, incubated in ice water for about 30 minutes, then applied to carbon film on a 300-mesh copper grid. The grids were then dried in vacuum and subjected to TEM. FIG. 2 shows the encapsulation of uranyl acetate by vesicles of Derivative 2. The picture clearly illustrates the efficacy of the encapsulation process.

Figure 7:
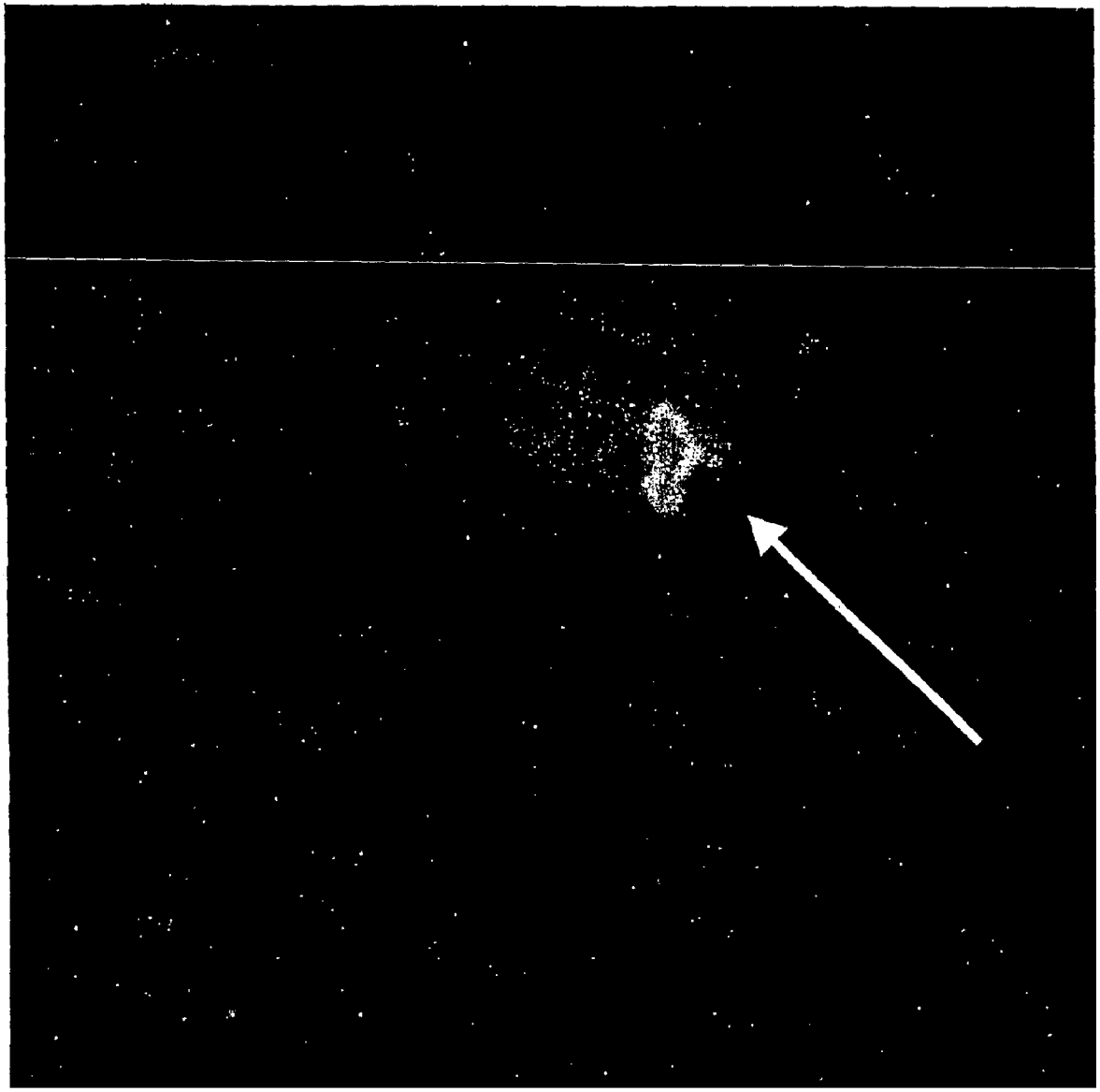
FIG. 7: Confocal image of Derivative 23 nanovesicles encapsulating DNA plasmid (4 kb). The encapsulation of the DNA plasmid was achieved by mixing the amphiphilic Derivative 23 (200 µl) with 300 micromoles of rodamine stained DNA followed by sonication. The vesicle was stained with FITC (ULSIS Alexa Fluor 488 Nucleic acid labelling kit). In the photo the arrow points to the DNA plasmid situated within the vesicle walls.

The same encapsulation procedure was used to encapsulate a DNA fragment, as shown in FIG. 7, and other nucleic acids, pesticides (e.g. 2,4-dichlorophenoxyacetic acid, not shown), trace elements (e.g. iron oxide, not shown) and proteins (e.g. Bt toxin, not shown).

Example 48

Figure 8:
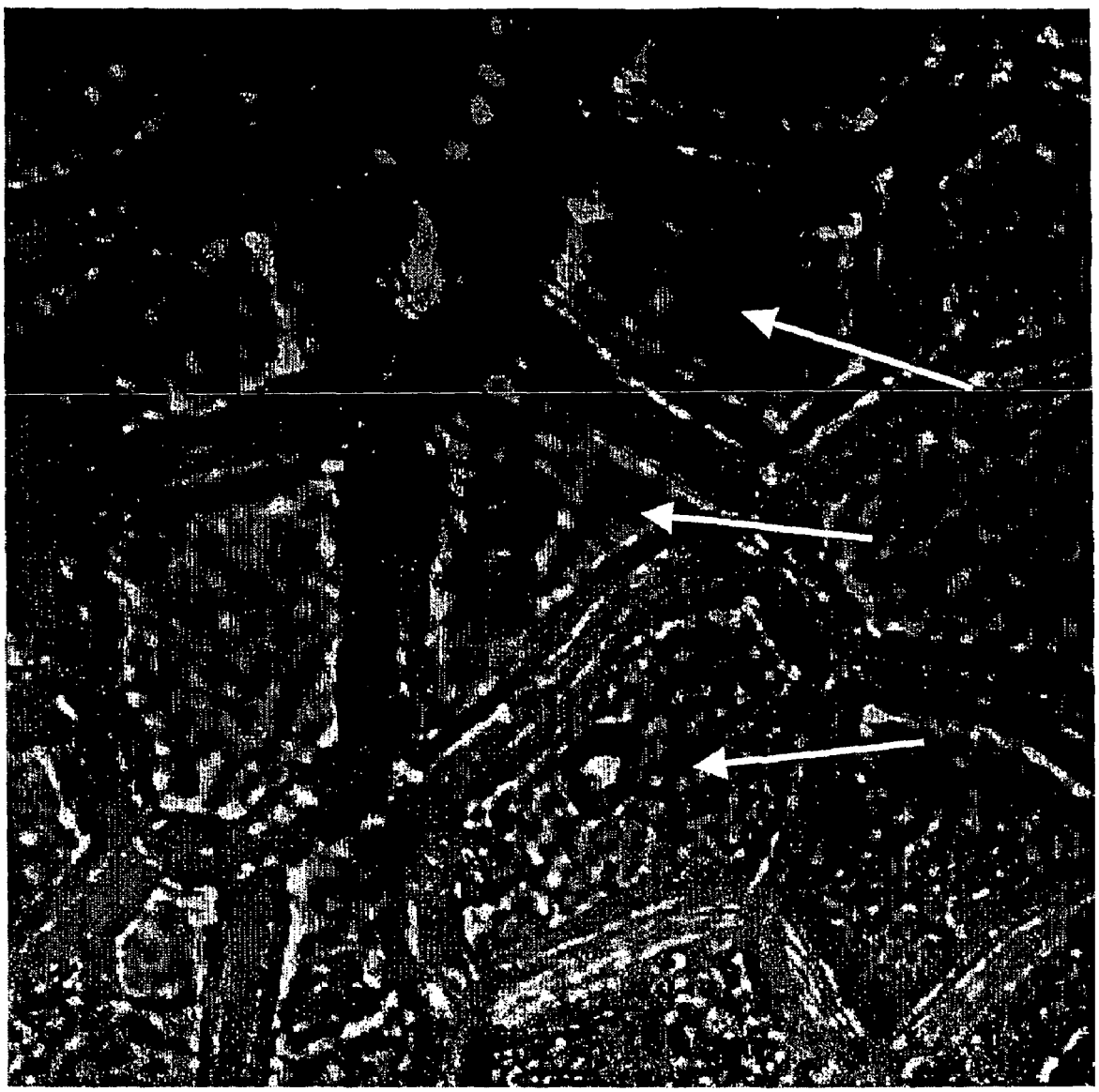
FIG. 8: Confocal image of Derivative 23 vesicles on the inner side of a citrus grandis abaxial side leaf isolated cuticle membrane. Ten micro liters of the vesicles were placed on the cuticle membranes isolated from the abaxial (upper) side of citrus grandis leaf, using the procedure described by Schonherr and Baur (1995). One, three and five days later the isolated cuticle membranes were analyzed in a Confocal microscopy system. As is clearly shown in the photo, nanovesicles (marked with arrows) were observed in the inner side of the cuticle.

Vernonia oil nanovesicle penetration through biological membranes In order to test the ability of nano-vesicles to penetrate and pass through biological membranes, a set of experiments using isolated plant cuticle membrane (known as a model for penetration studies [Schonherr and Baur, 1995]) was performed. Derivative 2 vesicles were used to encapsulate uranyl acetate as described in Example 42. Ten microliters of the vesicles were subjected to cuticle membranes isolated from the abaxial (upper) side of citrus grandis leaf, using the procedure described by Schonherr and Baur (1995). One, three and five days later the isolated cuticle membranes were analyzed in a Confocal microscopy system. As is clearly shown in FIG. 8, nano-vesicles were observed in the inner side of the cuticle, indicating that the nano-vesicles penetrated through the cuticle membrane. Similar results were obtained after one day, three and five days from application of the vesicles to the outer side of the cuticle. This showed the stability of the vesicles and their ability to pass through biological membranes and even through highly complicated cuticle membranes.

Example 49

Controlled release of materials through vernonia oil nanovesicles Vernonia oil nanovesicles encapsulating uranyl acetate, that showed high degree of stability such as Derivative 2, were transferred to a medium containing acidic buffer at pH 4.7. These vesicles were analyzed microscopically one, three and five days later. The integrity of the vesicle membrane was affected and the material was released out of the vesicle, while in the control treatment that was kept in neutral pH; the integrity of the vesicles was maintained and the material was still encapsulated in all the tested periods. Quantification of the rate of release of the material (Table 2) shows that already 24 hours after changing the vesicle medium to acidic, one half of the encapsulated material was released from the vesicles.

TABLE 2

Effect of pH on the integrity of the nano vesicles of Derivative 2 and the material release capacity.

| | Days | | | |
|---|---|---|---|---|
| | 0 | 1 | 3 | 5 |
| Control (neutral pH) | 0% | 0% | 0% | 0% |
| Acidic buffer pH (4.7) | 0% | 50% | 80% | 80% |

The data represents % of deformed vesicles that lost the encapsulated material.

Example 50

DNA Complexation

Purified Derivative 4 was used to complex with a DNA plasmid (purchased from Sigma Chemicals, 5 ng/microliter, stained in FITC; ULSIS Alexa Fluor® 488 Nucleic acid labeling kit) or rhodamine. The complexation was achieved by mixing the amphiphilic Derivative 4 (200 microliters containing 600 micromoles of the compound) with 300 micromoles of the DNA sample and letting it shake gently for a short period of time. The mixture is not sonicated to prevent vesicle formation in which the DNA is encapsulated. The sample was then incubated in a culture containing bronchial epithelial cells. Examination with a confocal microscope of the cells showed a significantly greater uptake of DNA by the cells in samples containing the DNA complexant as compared to the non-complexed DNA samples.

Example 51

Metal Ions Complexation

The Cu(II) complex of the Derivative 15 containing 3.8% Cu was characterized by UV-visible spectroscopy. A 50 nm shift of the methanolic solution containing the complex was observed in comparison with the absorbance of the starting copper (II) salt.

Example 52

Vesicle Formation Having Bilayer Membranes

Derivative 10 was made into vesicles according to Example 41. A TEM analysis as described in Example 41 showed vesicles of 350 rim in size. The same method was used to encapsulate $^{14}$C-methylated albumin (purchased from Sigma Chemicals) by adding 0.2 mg of the tagged albumin. The vesicles were purified by filtration and the presence of radioactivity in the purified sample indicated encapsulation. When these vesicles were incubated with bronchial epithelial cells measurement of radioactivity showed a significantly greater uptake of the albumin as compared with the non-encapsulated albumin.

Example 53

Preparation of Crosslinked Vesicles by Free Radicals through Double Bonds

Vesicles of Derivative 14 were placed in a solution containing 0.1% potassium persulfate for 60 minutes. The resultant vesicles had significantly better stability in 20% ethanol solutions while the non cross-linked vesicles were destroyed.

References

Ali, A.; Bittman, R., Chem. Phys. Lipids, 50, 11-21 (1989)
Benita, Simon (editor), "Microencapsulation Methods and Industrial Applications", Marcel Dekker, Inc. (1996)
Boder, H,. Ringdorf, H., Skuia, J. "Liposomes from Polymerizable Glycolipids", Angew. Chem. Int. Ed. Engl. 20, 91-92 (1981)
Eibl, H.; Nicksh, A., Chem. Phys. Lipids, 22, 1-8 (1978)
J. Fendler, J. Membrane Mimetic Chemistry, "Vesicles", Chapter 6, pp. 113-183, John Wiley & Sons (1982)
Fuhrhop J-H., Mathieu, J., "Routes to Functional Vesicle Membranes without Proteins", Angew. Chem. Int. Ed. Engl. 23, 100-113 (1984)
Grinberg, S.; Kolot, V.; Mills, D., Industrial Crops and Products, 3, 113-119 (1994)
Hansen, W. J.; Marari, R.; Wedmit, Y.; Baumann, W. J., Lipids, 17, 453-459 (1982)
Hirt, R.; Berchtold, R; Pharm. Chem. Helv., 33, 349-356 (1958)
Kunitake, T.; Okahata, Y. J., "Totally Synthetic Bilayer Membranes", J. Am. Chem. Soc., 99,3860-3861 (1977)
Kunitake, T.; Okahata, Y. J., J. Am. Chem. Soc., 102, 549 (1980)
Kunitake, T., N. Nak, K. K. Takarabe, M. Nagai, A. Tsuge and H. Yanagi, "Vesicles of Polymeric Bilayer and Monolayer Membranes", J Am. Chem. Soc., 103, 5945-5947 (1981a);
Kunitake, T., Okahata, Y. J., Shimomura, M., Yasunami, S., "Formation of Stable Bilayer Assemblies in Water from Single Chain Amphiphiles. Relationship Between the Amphiphiles Structure and Aggregate Morphology", J Am. Chem. Soc., 103, 5401-5413 (1981b)
Schönherr, J., Baur, P., Pest. Sci., 42, 185-208 (1994)
Sumida Y. et al., "New pH-sensitive vesicles, release control of trapped materials from the inner aqueous phase of the vesicle made from triple chain amphiphiles bearing two carboxyl groups", Langmuir 17, 609-612 (2001)
Toshinori and J. Sunamoto, "Recent Aspects in the Use of Liposomes in Biotechnology and Medicine", Prog. Lipid Res., 31:345 (1992)
Wenner, J., J. Org. Chem., 22, 1508 (1957)

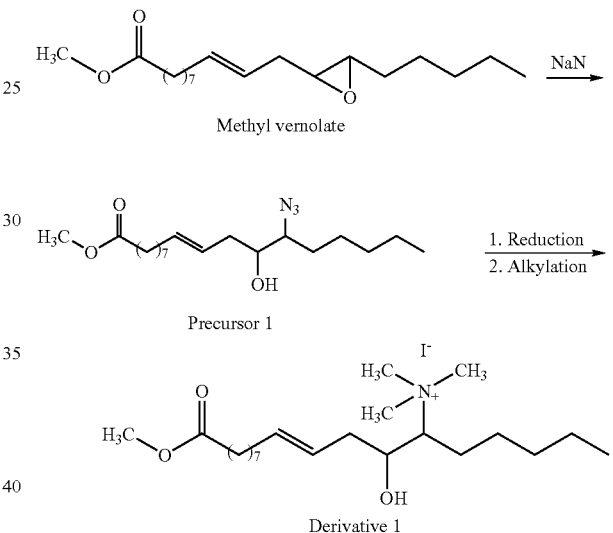

SCHEME 1

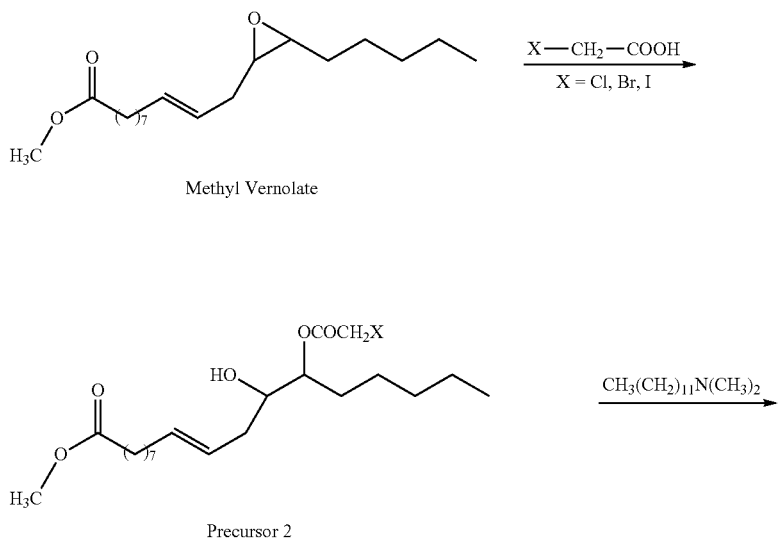

SCHEME 2

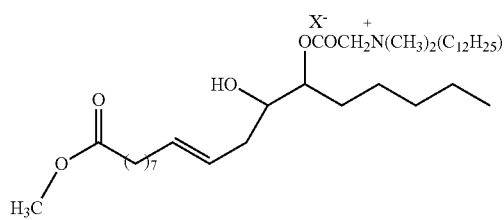
Derivative 2
SCHEME 3
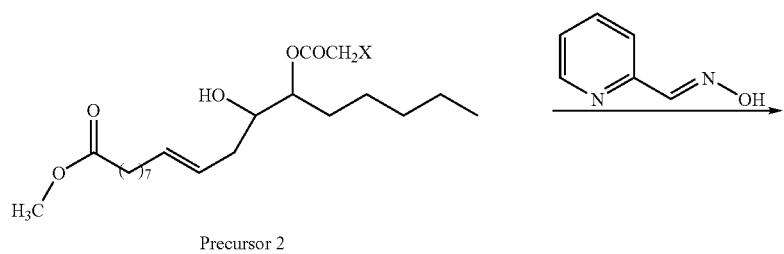
Precursor 2
X = Br, I
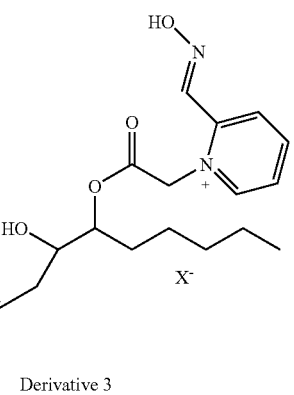
Derivative 3
SCHEME 4
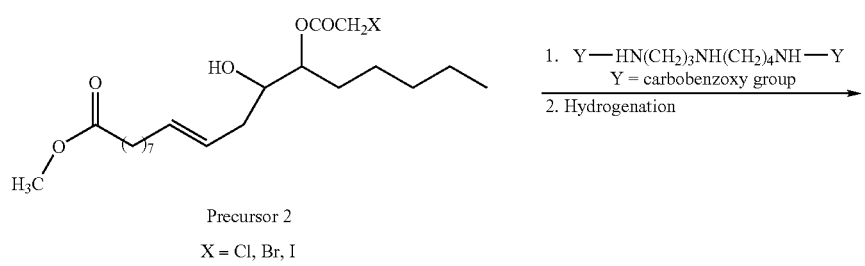
Precursor 2
X = Cl, Br, I

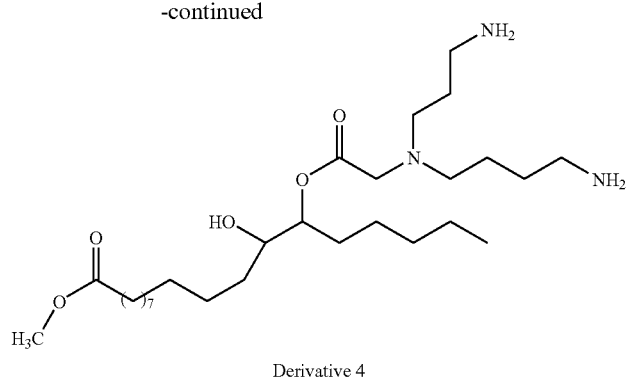
Derivative 4
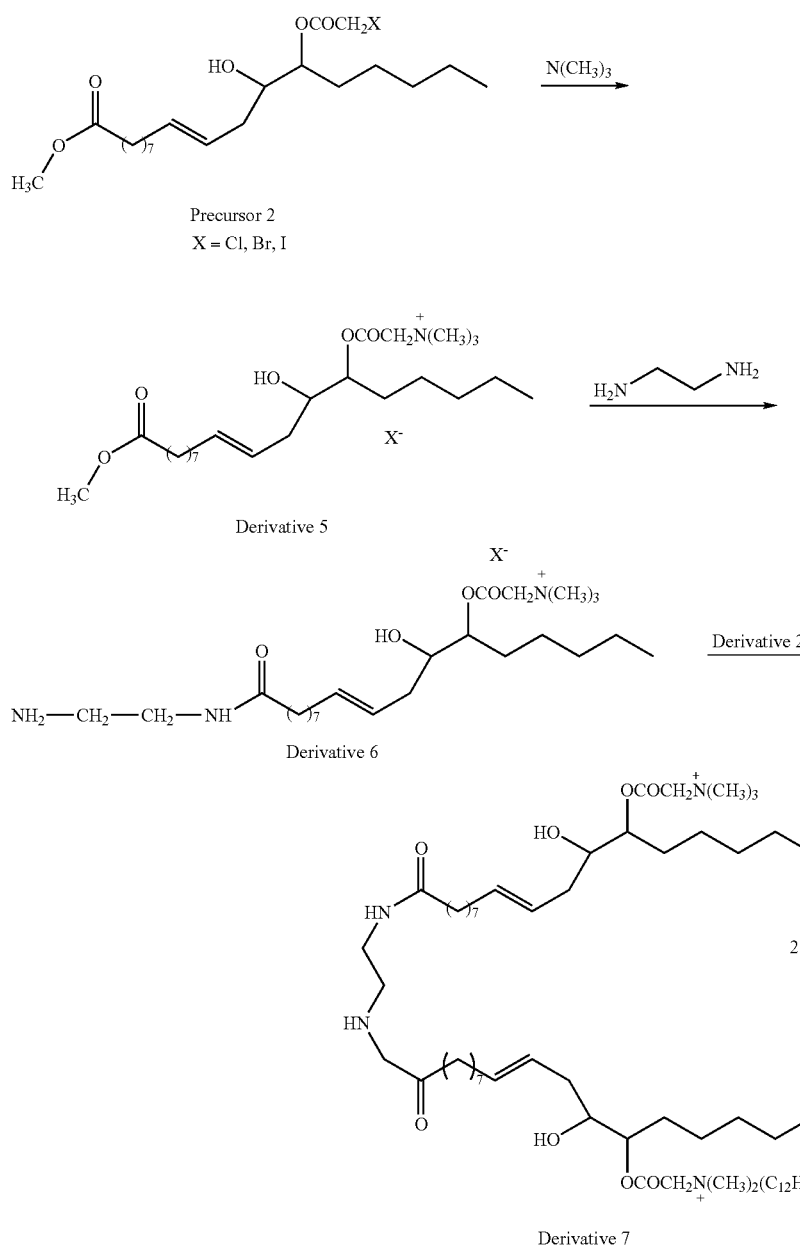

SCHEME 6
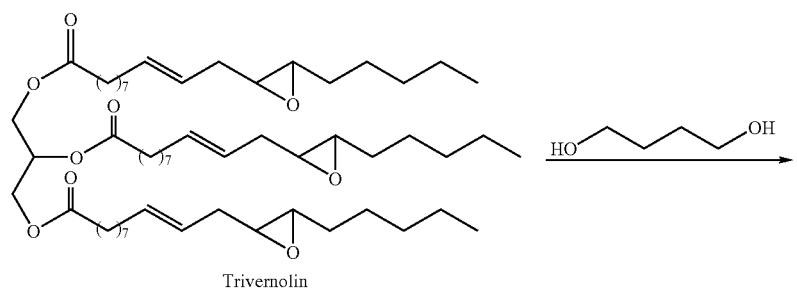
Trivernolin
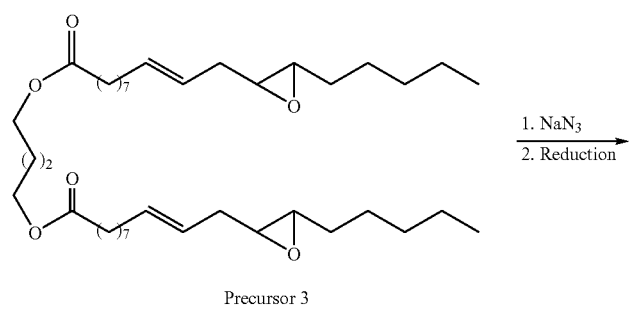
Precursor 3
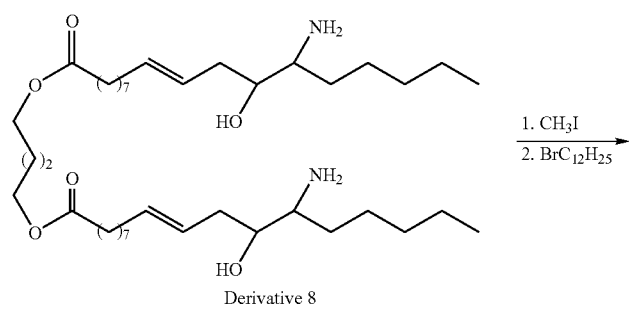
Derivative 8
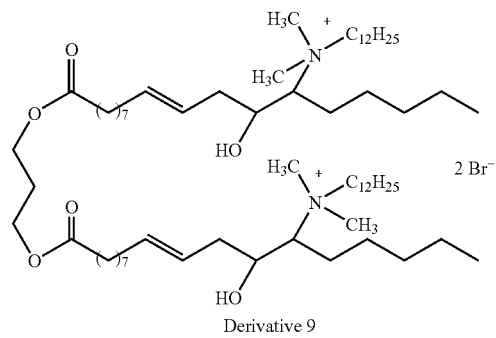
Derivative 9

SCHEME 7
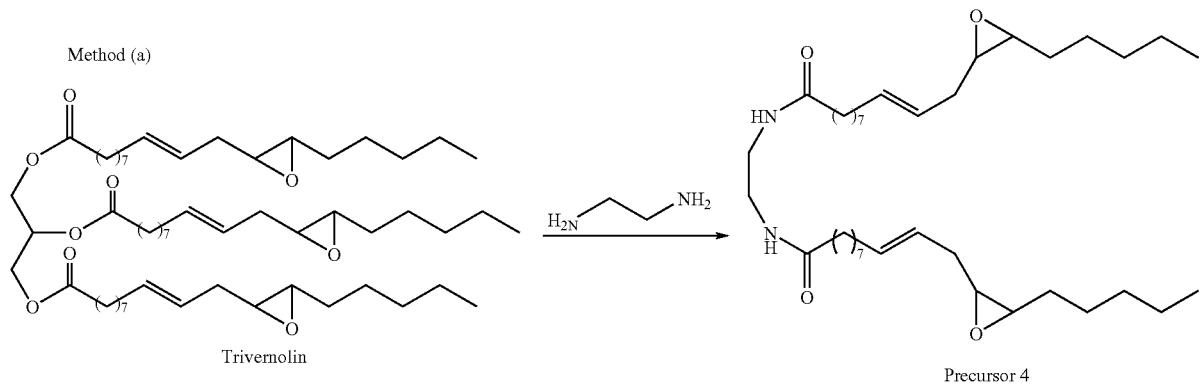
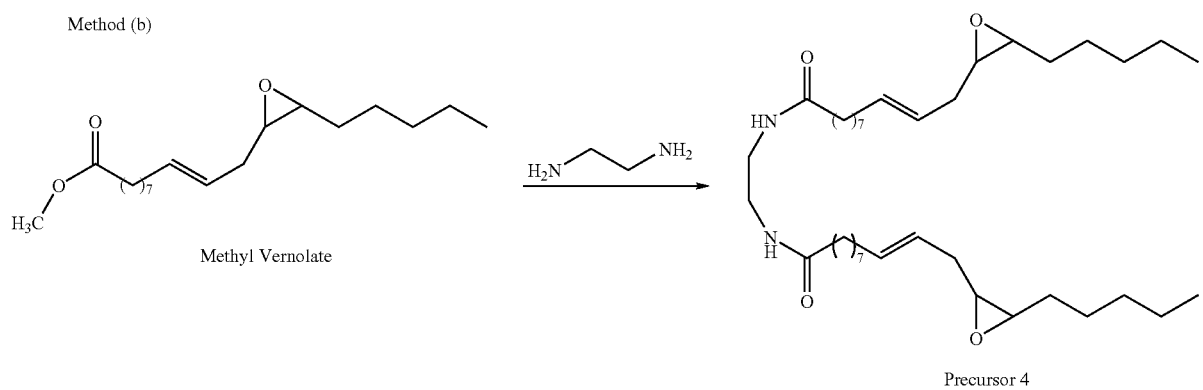
SCHEME 8
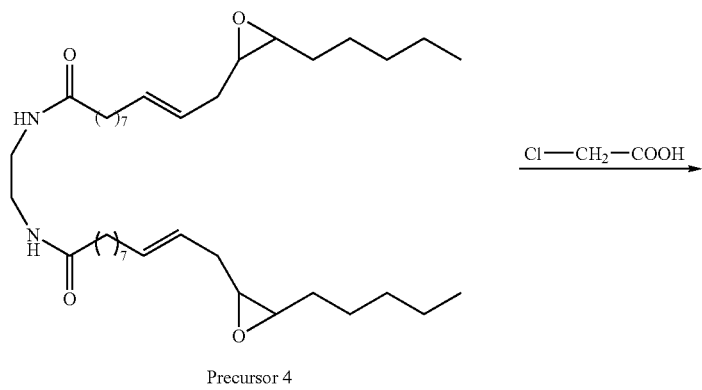

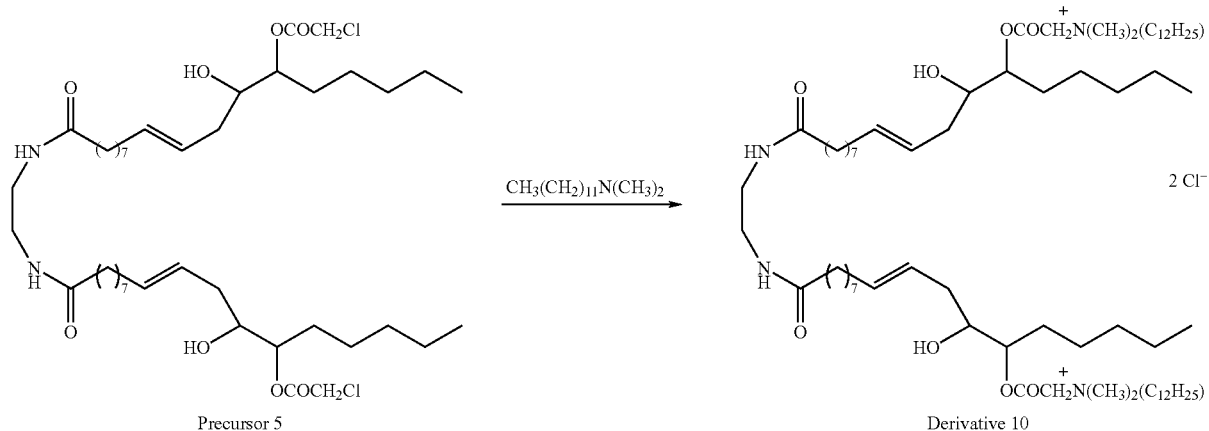
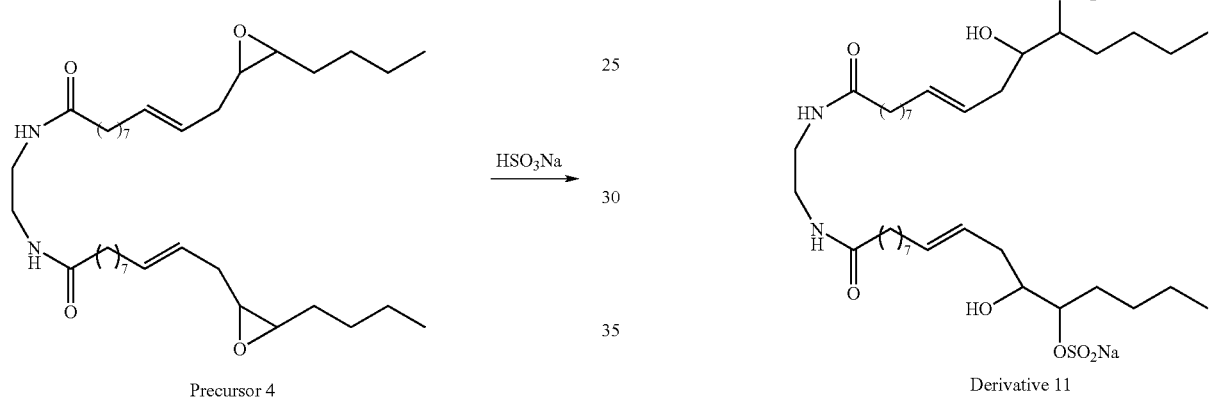
SCHEME 10
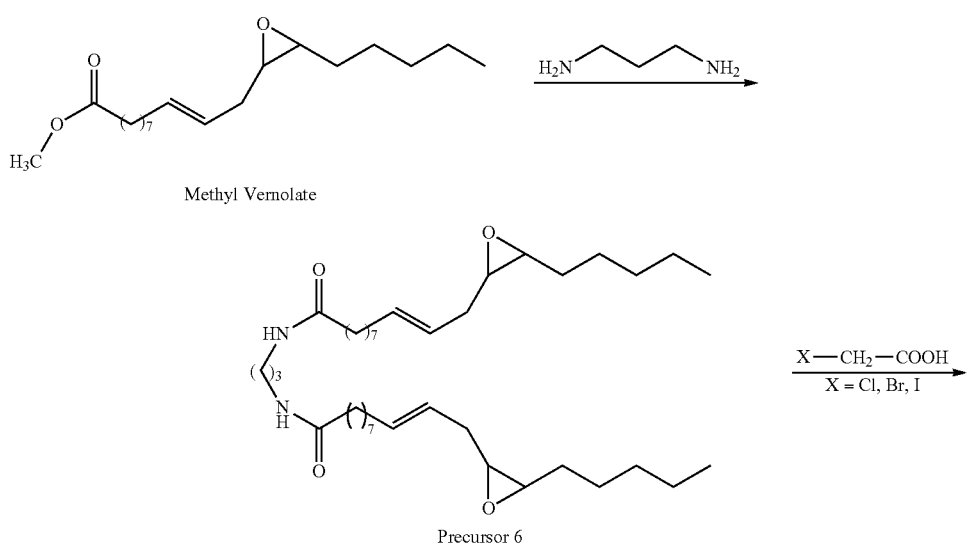

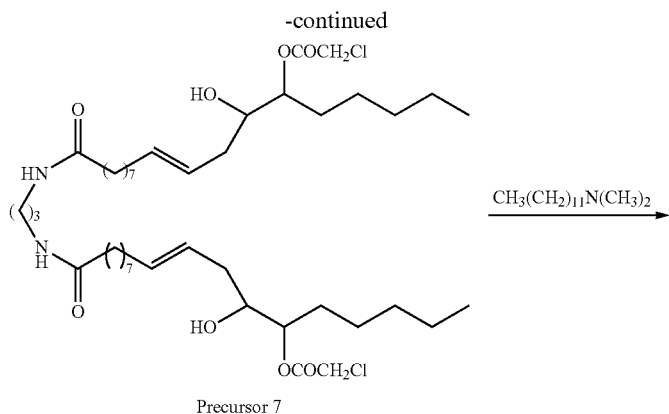
Precursor 7
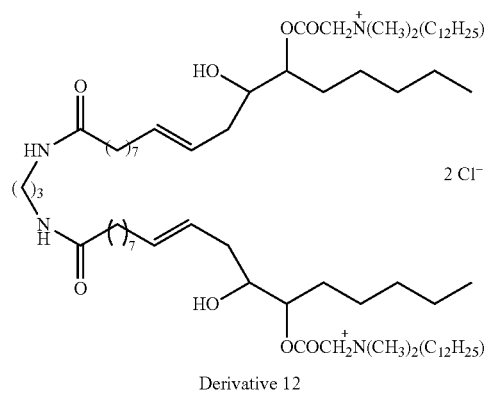
Derivative 12
SCHEME 11
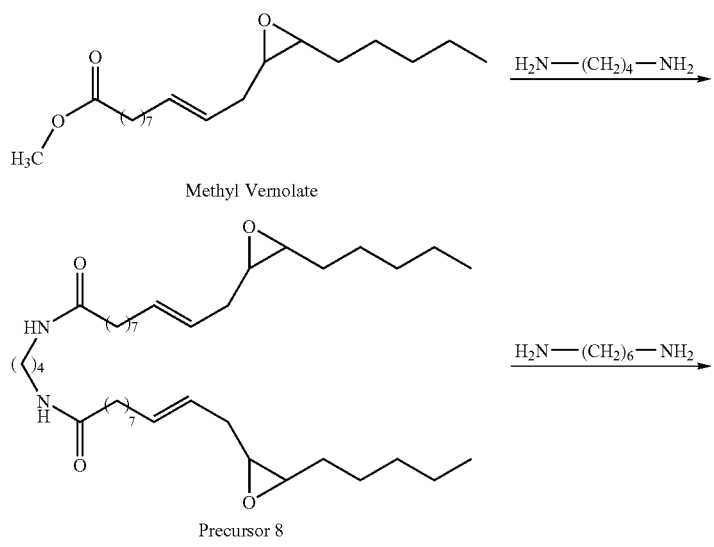
Precursor 8

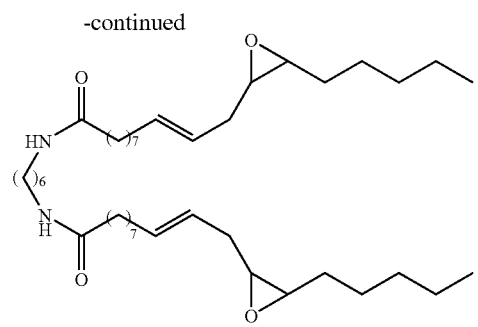
Precursor 9
SCHEME 12
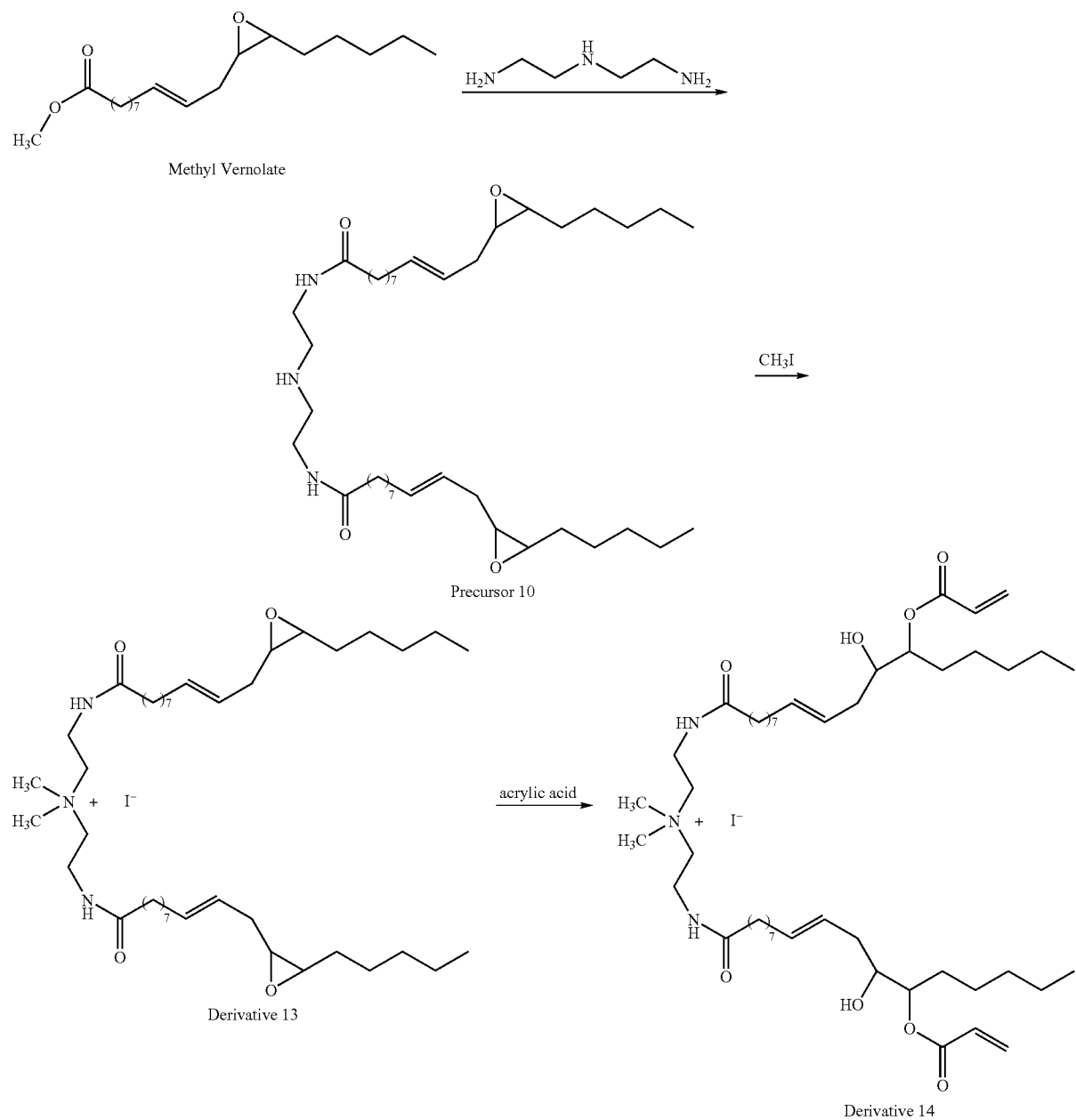

SCHEME 13
Trivernolin →(Triethylene tetramine)→
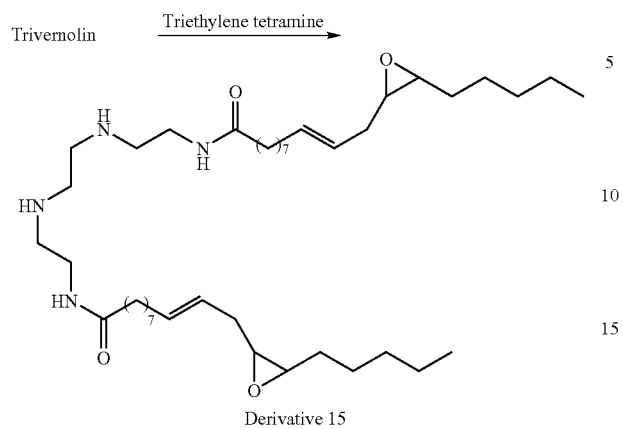
Derivative 15
SCHEME 14
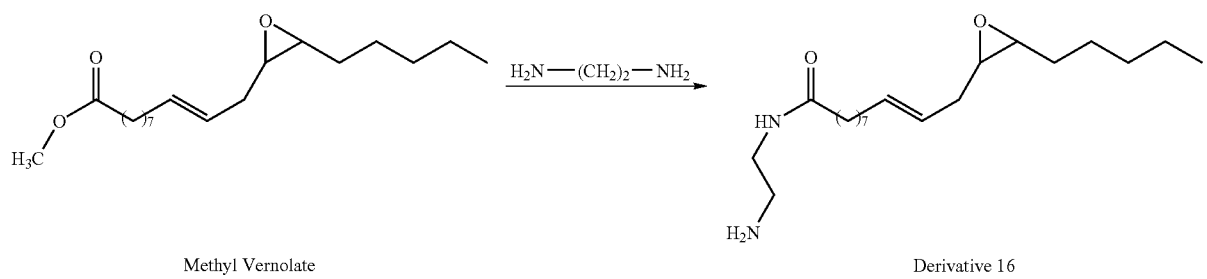
Methyl Vernolate → (H$_2$N—(CH$_2$)$_2$—NH$_2$) → Derivative 16
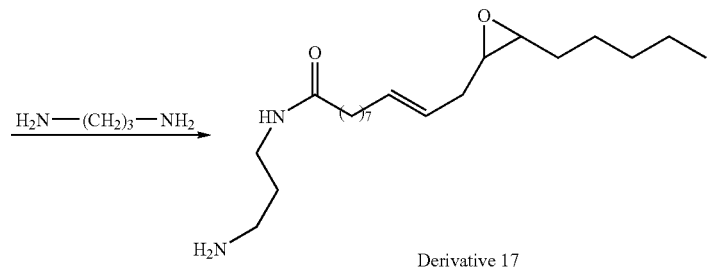
H$_2$N—(CH$_2$)$_3$—NH$_2$ → Derivative 17
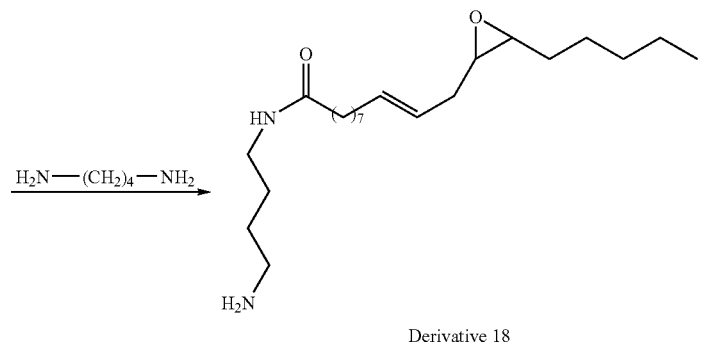
H$_2$N—(CH$_2$)$_4$—NH$_2$ → Derivative 18

-continued
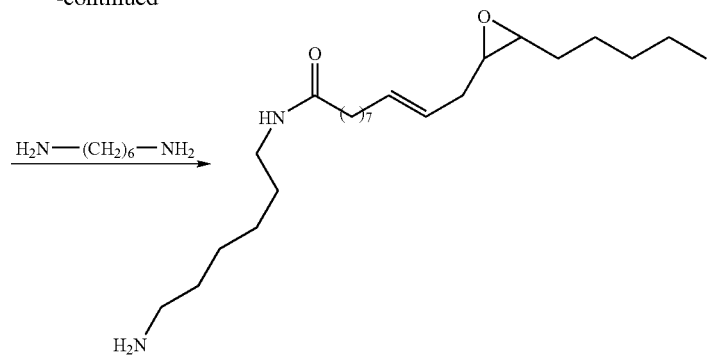
Derivative 19
SCHEME 15
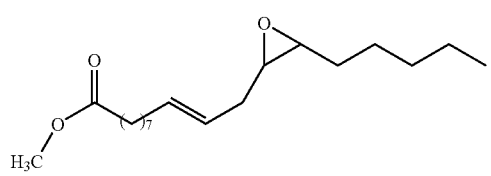
Methyl Vernolate
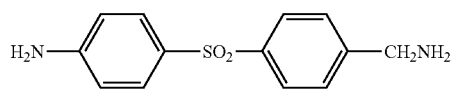
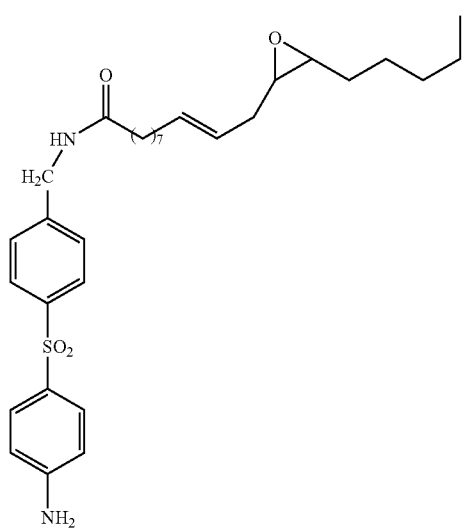
Derivative 20
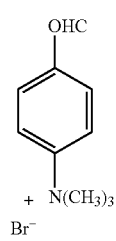
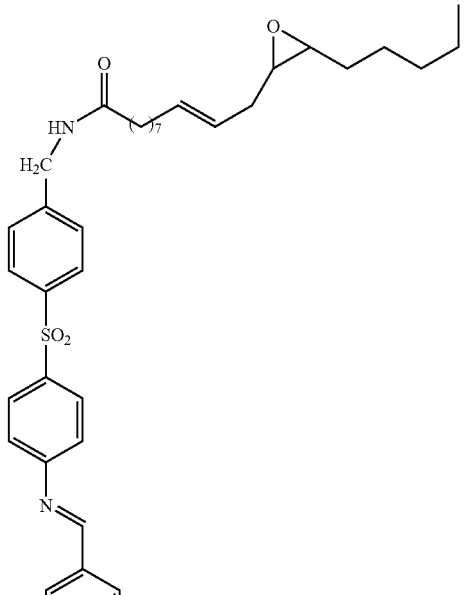
Derivative 21

SCHEME 16
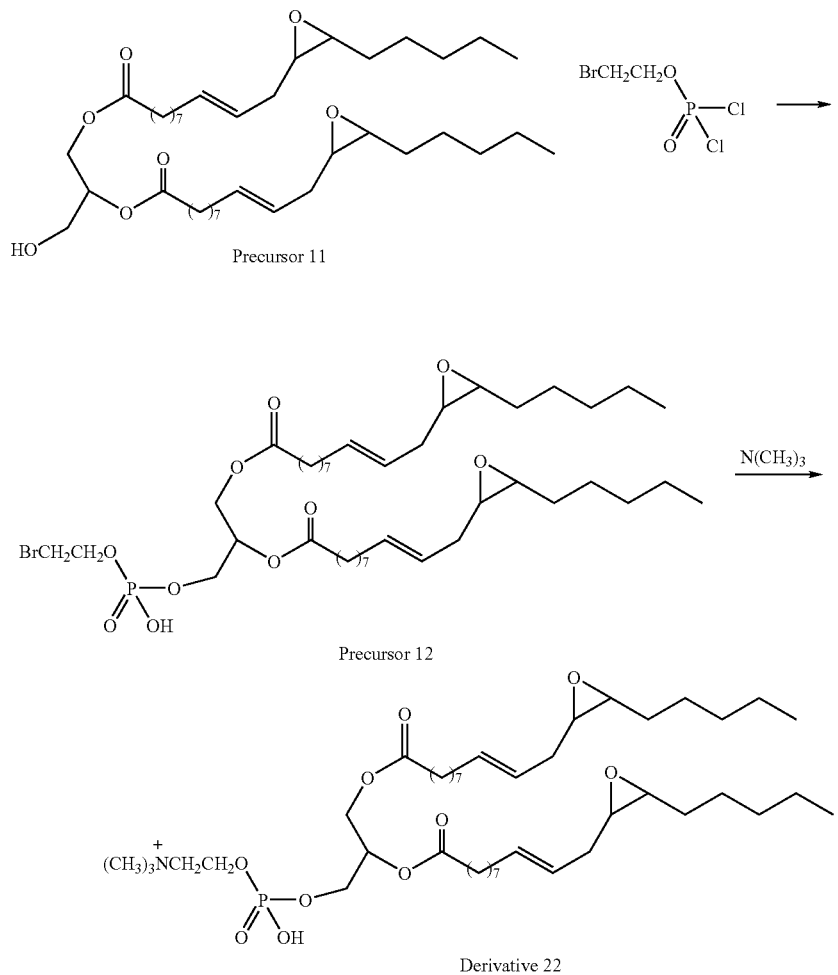
SCHEME 17
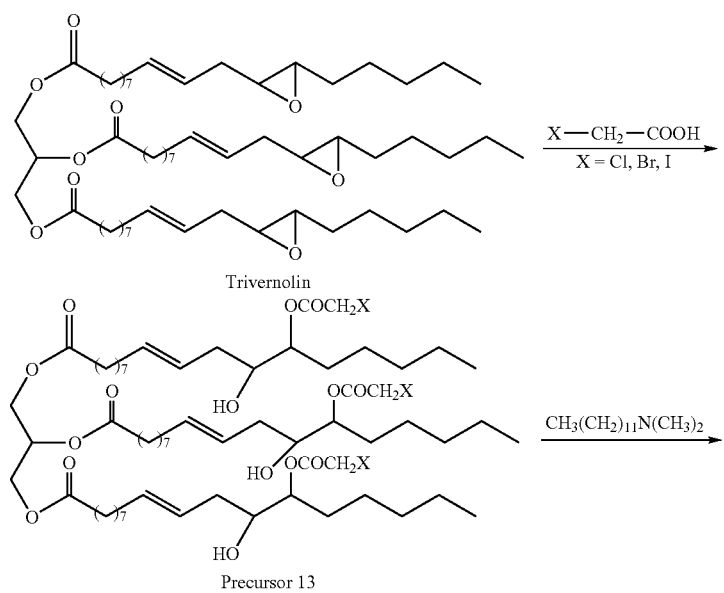

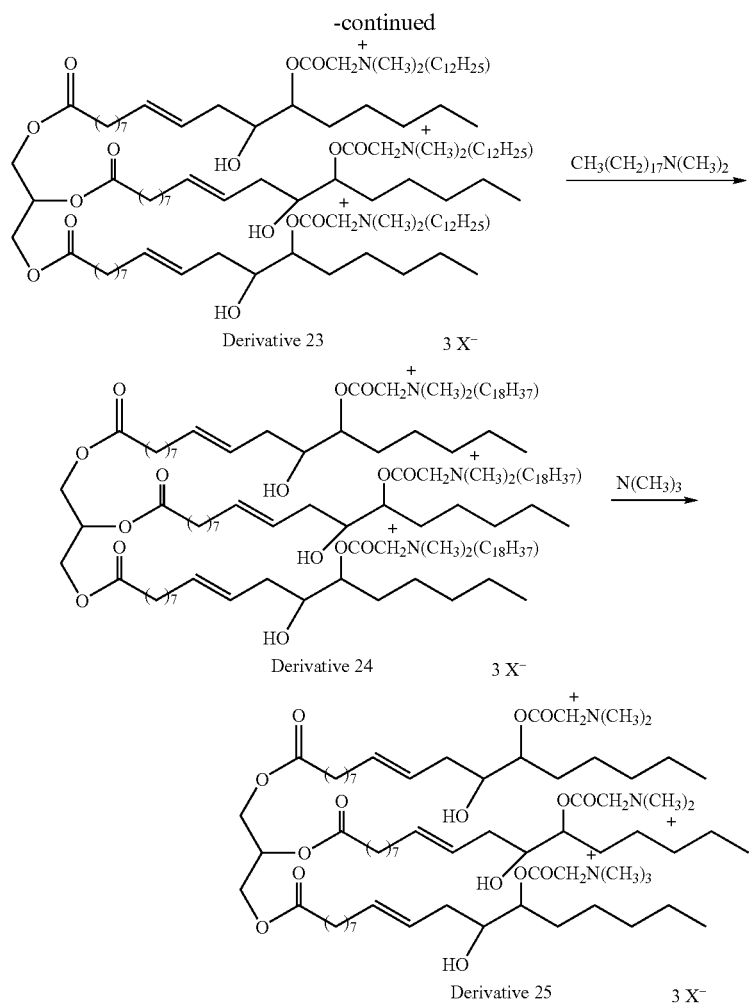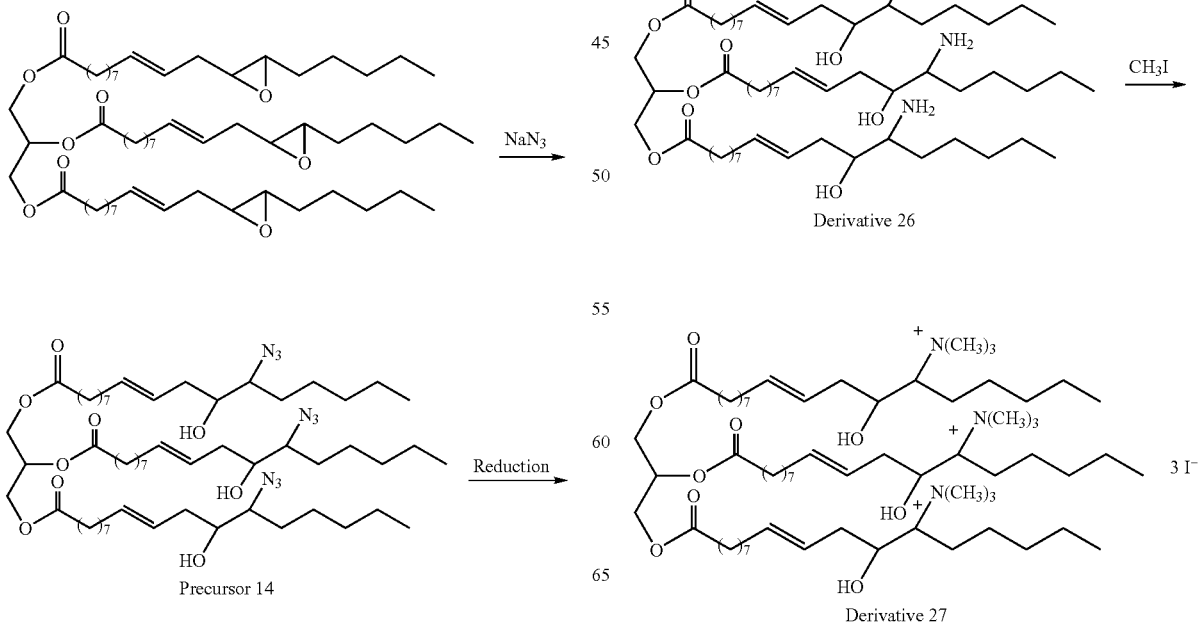
SCHEME 18

SCHEME 19
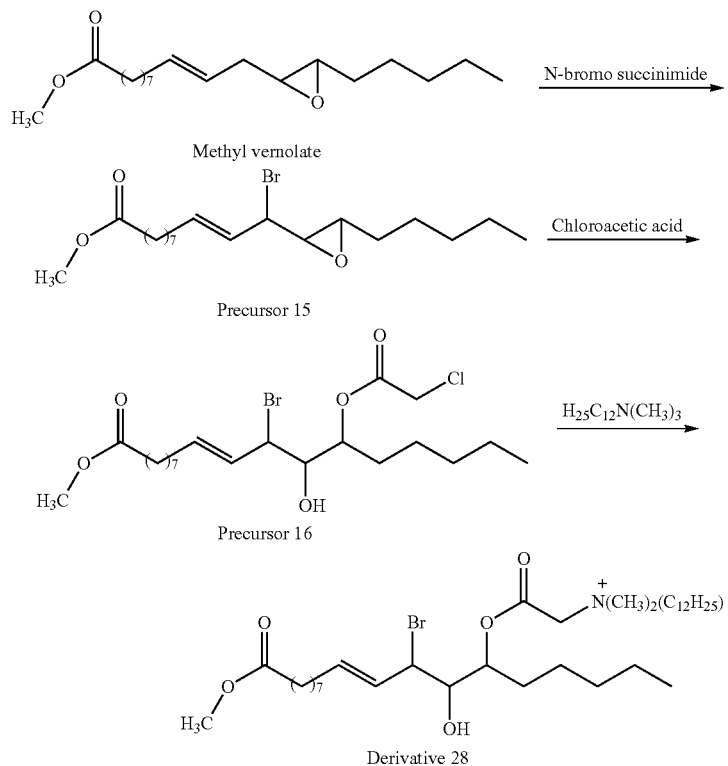
SCHEME 20
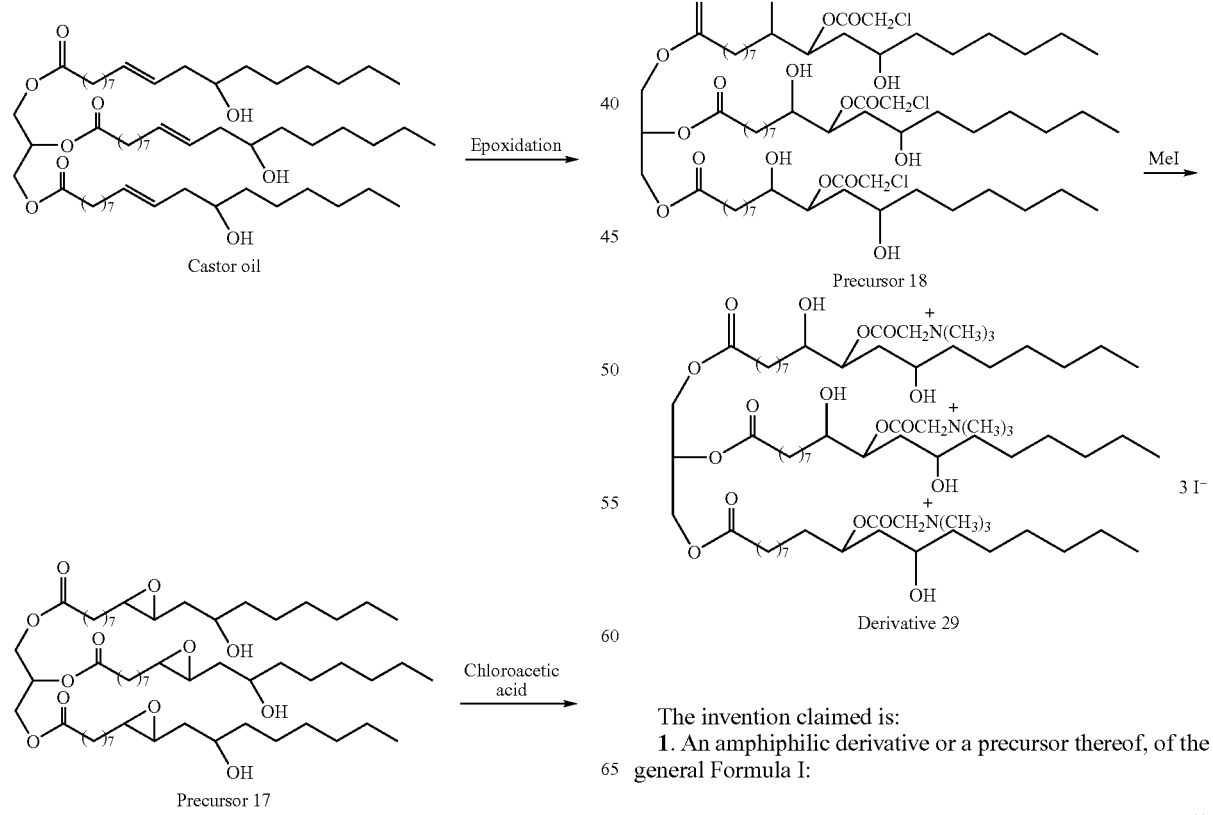
The invention claimed is:
1. An amphiphilic derivative or a precursor thereof, of the general Formula I:
$$A_1\text{-CO}—R_1—R_2—R_3—R_4—R_5 \quad (I)$$

wherein $R_1$ is $C_5$-$C_{10}$ alkylene;

$R_2$ is 2,3-oxiranylene, —CH=CH—(CH$_2$)$_n$—, —CH$_2$—CH(X)—, —CH(X)—CH(X)—, —(CH=CH—CH(X))$_m$—, —(CH$_2$—CH(X)—CH$_2$)$_o$—, or —(CH(X)—CH(X)—CH$_2$)$_p$—, wherein X is halogen, hydroxy, amino, —O—CO—(CH$_2$)$_n$—R$_{26}$, or —N$^+$(R$_{22}$R$_{23}$R$_{24}$), n is an integer from 0 to 7, and m, o, and p are integers from 1 to 3;

$R_3$ is $C_1$-$C_4$ alkylene, optionally substituted by halogen, amino or hydroxy;

$R_4$ is 2,3-oxiranylene, —CH(OH)—CH(R$_{25}$)—, —CH$_2$—CH(R$_{25}$)—, —CH(OH)—CH(X)—, and —CH(OH)—CH(O—CO—R$_6$—R$_7$—R$_8$—R$_9$—R$_{10}$)—, wherein X is as defined above in $R_2$;

$R_5$ is $C_1$-$C_{11}$ alkyl, and wherein the total sum of carbon atoms in the $R_1$—$R_2$—$R_3$—R4—$R_5$ chain is at most 23;

$A_1$ is —NH—R$_0$, —O—R$_0$, —S—R$_0$, or —O—PO(OH)—O—R$_0$;

$R_0$ is $C_1$-$C_6$ alkyl, or a residue selected from the groups (a)-(h) below, wherein A$_1$ can only be —O—R$_0$ when R$_0$ is $C_1$-$C_6$ alkyl or one of the groups (f), (g), or (h):

(a) —R$_{11}$-Q$_1$—CO—R$_6$—R$_7$—R$_8$—R$_9$—R$_{10}$;
(b) —R$_{17}$-Q$_1$—CO—R$_{12}$—R$_{13}$—R$_{14}$—R$_{15}$—R$_{16}$;
(c) —R$_{19}$-Q$_1$—R$_{18}$;
(d) —R$_{19}$-Q$_1$—R$_{20}$—G;
(e) —CH$_2$—CH(OR$_{21}$)—CH$_2$—OR$_{21}$;

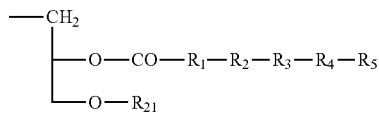

(f)

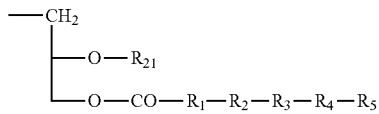

(g)

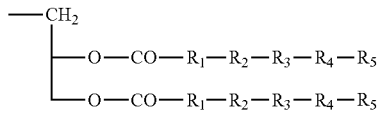

(h)

$R_6$ is $C_2$-$C_{10}$ alkylene;

$R_7$ is a covalent bond or as defined for $R_2$ above;

$R_8$ is a covalent bond or $C_1$-$C_4$ alkylene;

$R_9$ is a covalent bond, $C_1$-$C_{14}$ alkylene, or as defined for $R_4$ above;

$R_{10}$ is $C_1$-$C_{11}$ alkyl;

$Q_1$ is a covalent bond, —NH—, —O—, —S—, or —O—PO(OH)—O—;

$R_{11}$ is a spacer group selected from: $C_1$-$C_6$ alkylene, $C_6$-$C_{14}$ arylene, —($C_6$-$C_{14}$ arylene)—R$_{28}$—($C_6$-$C_{14}$ arylene)—, —(CH$_2$—CH$_2$—O)$_n$—CH$_2$—CH$_2$—, —(CH$_2$—CH$_2$—NH)$_m$—CH$_2$—CH$_2$—, —(CH$_2$—CH$_2$—S)$_o$—CH$_2$—CH$_2$—, —(CH(CH$_3$)—CH$_2$)$_p$—, —CH(CH$_3$)—(CH$_2$)$_q$—CH(CH$_3$)—, and —CH$_2$—CH(CH$_2$—O—R$_{21}$)—, wherein the $C_6$-$C_{14}$ arylene groups may be substituted each by R$_{27}$, and n, m, o, p and q are integers from 1 to 6;

$R_{12}$ is as defined for $R_6$ above;
$R_{13}$ is as defined for $R_7$ above;
$R_{14}$ is as defined for $R_8$ above;
$R_{15}$ is as defined for $R_9$ above;
$R_{16}$ is as defined for $R_{10}$ above;

$R_{17}$ is as defined for $R_{11}$ above or is a group —(CH$_2$)$_n$—N$^+$R$_{22}$R$_{23}$—(CH$_2$)$_m$— or —(CH$_2$)$_O$ —NR$_{22}$—(CH$_2$)$_p$—, wherein n, m, o and p are integers from 1 to 4;

G is hydrogen, or a molecule selected from the group consisting of a protein, a polypeptide, an antibody, a polynucleotide, a DNA or a DNA fragment, RNA or RNA fragment, a polysaccharide, a plasmid, and a chemotherapeutic agent;

$R_{18}$ is hydrogen; —NR$_{22}$R$_{23}$; —N$^+$R$_{22}$R$_{23}$R$_{24}$; —N=CH—(C$_6$-$C_{14}$ arylene)—N$^+$R$_{22}$R$_{23}$R$_{24}$; $C_1$-$C_8$ alkyl [optionally substituted by $C_6$—$C_{14}$ aryl or by R$_{29}$]; $C_6$-$C_{14}$ aryl; $C_4$-$C_9$ heteroaryl containing one or more heteroatoms selected from N, O, and S, said $C_6$-$C_{14}$ aryl and $C_4$-$C_9$ heteroaryl being optionally substituted by $C_1$-$C_6$ alkyl, —(CH$_2$)$_n$—NH$_2$, —COOH, —SH, —SO$_3$H, —O—SO$_2$H, or —O—PO(OH)$_2$; —(CH$_2$)$_{m-(C_6}$-$C_{14}$ arylene) —R$_{29}$; —(CH$_2$)$_O$—(C$_6$-$C_{14}$ arylene)—(CH$_2$)$_p$ —R$_{29}$; —O—PO(OH)—O—CH$_2$—CH$_2$—N$^+$(CH$_3$)$_3$; —O—PO(OH)—O—CH$_2$—CH$_2$—NH$_2$; or —O—PO(OH)—O—CH$_2$—CH(COO$^-$)—NH$_3^+$; wherein n is an integer from 1 to 6, m and o are integers from 1 to 20, and p is an integer from 0 to 20;

$R_{19}$ is as defined for $R_{11}$ above, or is a spacer group selected from —CH$_2$—(C$_6$-$C_{14}$ arylene) —R$_{28}$—(C$_6$-$C_{14}$ arylene) —; bi (C$_6$-$C_{14}$) arylene; bi ($C_4$-$C_9$) heteroarylene; and $C_4$-$C_9$ heteroarylene, wherein said bi($C_4$-$C_9$)heteroarylene and $C_4$-$C_9$ heteroarylene each contain one or more heteroatoms selected from N, O, and S, and are optionally substituted by —OH, —COOH, —SH, —SO$_3$H, —O—SO$_2$H, and —O—PO(OH)$_2$;

$R_{20}$ is $C_1$-$C_8$ alkylene, optionally substituted by $C_6$-$C_{14}$ aryl or R$_{29}$; $C_6$-$C_{14}$ arylene; or $C_4$-$C_9$ heteroarylene containing one or more heteroatoms selected from N, O, and S, said $C_6$-$C_{14}$ arylene and $C_4$-$C_9$ heteroarylene being optionally substituted by $C_1$-$C_6$ alkyl, —(CH$_2$)$_n$—NH$_2$, —COOH, —SH, —SO$_3$H, —O—SO$_2$H, or —O—PO(OH)$_2$;

$R_{21}$ is —O—PO(OH)$_2$, —O—PO(OH) —O—CH$_2$—CH$_2$—X, wherein X is as defined for $R_2$, or —O—PO(OH)—O—CH$_2$—CH(COO$^-$)—NH$_3^+$;

$R_{22}$, $R_{23}$, and $R_{24}$, independently of each other, are each hydrogen; $C_1$-$C_{20}$ alkyl or $C_6$-$C_{14}$ aryl, said $C_1$-$C_{20}$ alkyl and $C_6$-$C_{14}$ aryl being optionally substituted by halogen, $C_6$-$C_{14}$ aryl, —OH, —NH$_2$—, —SH, —COOH, —SO$_3$H, —O—SO$_2$H, —O—PO(OH)$_2$, —O—PO(OH)—O—(CH$_2$)$_2$—NH$_3^+$, or —O—PO(OH)—O—CH$_2$—CH(COO$^-$)—NH$_3^+$; or $R_{24}$ is absent and $R_{22}$ and $R_{23}$ together with the N atom to which they are attached form an aromatic or non-aromatic heterocyclic ring optionally charged in the N atom, said heterocyclic ring optionally containing a further heteroatom selected from N, O, and S, and further being optionally substituted by —NH$_2$, —COOH, —CH=N—OH, —OH, —SO$_3$H, and —O—PO(OH)$_2$;

$R_{25}$ is N$_3$; —O—CO—(C$_2$-$C_6$ alkenyl), —O—CO—(CH$_2$)$_n$—R$_{26}$; —(CH$_2$)$_m$—O—SO$_2$H; —O—SO$_2$H; —(CH$_2$)$_o$—COOH; —(CH$_2$)$_p$—O—PO(OH)$_2$; —O—PO(OH)$_2$; —O—PO(OH) —O—(CH$_2$)$_q$—N$^+$R$_{22}$R$_{23}$R$_{24}$; —N$^+$R$_{22}$R$_{23}$R$_{24}$; —NR$_{22}$R$_{23}$; —N$^+$(CH$_3$)$_2$—R$_{30}$; —SR$_{31}$; —R$_{32}$—(C$_6$-$C_{14}$ arylene) —R$_{26}$; or —R$_{32}$—(C$_6$-$C_{14}$ arylene)—(CH$_2$)$_r$—R$_{26}$, wherein n, m, o, p, and q are integers from 1 to 14, and r is an integer from 1 to 3;

$R_{26}$ is halogen; $-NR_{22}R_{23}$; $-N^+R_{22}R_{23}R_{24}$; $-COOH$; $-SO_3H$; $-O-PO(OH)_2$; $-NH-(CH_2)_n-SO_3H$; $-NH-(CH_2)_m-COOH$; $-NH-(CH_2)_o-O-PO(OH)_2$; $-O-PO(OH)-NH-PO(OH)-O-$; $-N^+(CH_3)_2-R_{30}$; $-O-PO(OH)-O-(CH_2)_2-N^+R_{22}R_{23}R_{24}$; $-O-PO(OH)-O-(CH_2)_2-NH_3^+$; and $-O-PO(OH)-O-CH_2-CH(COO^-)-NH_3^+$; wherein n, m, and o are integers from 1 to 3;

$R_{27}$ is $-(CH_2)_n-NR_{22}R_{23}-$, $-NH-(CH_2)_m-SO_3H$, $-NH-(CH_2)_o-COOH$, $-NH-(CH_2)_p-O-PO(OH)_2$, $-NH-PO(OH)_2$, $-NH-(CH_3)_2-R_{30}$, $-NH-(CH_2)_n-O-PO(OH)-O-(CH_2)_2-NH_3^+$, or $-NH-(CH_2)_q-O-PO(OH)-O-CH_2-CH(COO^-)-NH_3^+$, wherein n, m, o, p, and q are integers from 0 to 3;

$R_{28}$ is $C_2$-$C_4$ alkylene, $-C(CH_3)_2-$, $-O-$, $-NH-$, $-S-$, or $-SO_2$;

$R_{29}$ is $-COOH$, $-NR_{22}R_{23}$, $-(CH_2)_n-N^+R_{22}R_{23}R_{24}-$, wherein n is an integer from 0 to 3; and as defined for $R_{27}$ above;

$R_{30}$ is $-CH_2-CH=CH_2$, $-CO-CH=CH_2$, $-CO-C(CH_3)=CH_2$, $-(CH_2)_n-N^+R_{22}R_{23}R_{24}$, $-(CH_2)_m-NH-(CH_2)_o-SO_3H$, $-(CH_2)_p-NH-(CH_2)_q-COOH$, $-(CH_2)_r-NH-(CH_2)_s-O-PO(OH)_2$, $-PO(OH)_2$, or $-O-PO(OH)-O-(CH_2)_2-N^+R_{22}R_{23}R_{24}$, wherein n, m, p, q, r, and s are integers from 0 to 3;

$R_{31}$ is hydrogen, $C_2$-$C_6$ alkenyl with a terminal double bond, $-CO-CH=CH_2$, or $-CO-C(CH_3)=CH-NR_{22}R_{23}$;

$R_{32}$ is $-NH-$, $-O-$, $-S-$, $-CH_2-NH-$, $-CH_2-S-$, or $-CH_2-O-$; and salts thereof, with the proviso that the compounds vernolic acid, trivernolin, N,N'-ethylene bis (vernolamide), N,N'-propylene bis (vernolamide), and 1,2-bis (2-aminoethoxy)ethane N,N' bis (vernolamide), are excluded, and wherein $R_2$ and/or $R_4$ is substituted by at least one polar, ionic and/or epoxy group and/or by at least one moiety containing at least one polar, ionic and/or epoxy group, said at least one polar, ionic and/or epoxy group and at least one moiety containing at least one polar, ionic and/or epoxy group being substitutions in any combination of 1-2, 1-2-3, 1-2-3-4, 1-2-4-5, 1-2-3-4-5, 1-2-4, 1-2-5, 1-3-4, 1-3, 1-5, 1-4, or 1-2-6 positions of the chain, the position 1 being arbitrarily assigned to the substitution most remote from the CO group, provided that at least one of said polar or ionic group is a polar or ionic head group.

2. An amphiphilic derivative or a precursor thereof according to claim 1, of the formula Ia:

$$R_0-O-CO-R_1-R_2-R_3-R_4-R_5 \quad \text{(Ia)}$$

wherein
$R_1$ is $C_5$-$C_{10}$ alkylene;
$R_2$ is $-CH=CH-(CH_2)_n-$, $-CH_2-CH(X)-$, $-CH(X)-CH(X)-$, $-(CH=CH-CH(X))_m-$, $-(CH_2-CH(X)-CH_2)_o-$, or $-(CH(X)-CH(X)-CH_2)_p-$, wherein X is halogen, amino, or $-N^{30}(R_{22}R_{23}R_{24})$, n is an integer from 0 to 7, and m, o, and p are integers from 1 to 3;
$R_3$ is $C_2$-$C_4$ alkylene, optionally substituted by halogen, amino or hydroxy;
$R_4$ is 2,3-oxiranylene, $-CH(OH)-CH(R_{25})-$, $-CH_2-CH(R_{25})-$, $-CH(OH)-CH(X)-$, or $-CH(OH)-CH(O-CO-R_6-R_7-R_8-R_9-R_{10})-$, wherein X is as defined above in $R_2$;

$R_5$ is $C_1$-$C_{11}$ alkyl, wherein the total sum of carbon atoms in the $R_2-R_2-R_2-R_4-R_5$ chain is at most 23;
$R_0$ is $C_1$-$C_6$ alkyl or one of the groups (f), (g), or (h) as defined in claim 1; and
wherein $R_6$, $R_7$, $R_8$, $R_9$, $R_{10}$, $R_{22}$, $R_{23}$, $R_{24}$ and $R_{25}$ are as defined in claim 1.

3. An amphiphilic derivative or a precursor thereof according to claim 2 of the formula Ib:

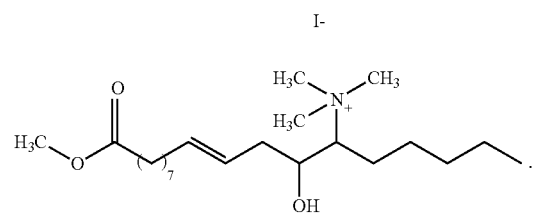

(Ib)

wherein $R_0$, $R_1$, $R_2$, $R_3$, $R_5$, and $R_{25}$ are as defined in claim 2.

4. An amphiphilic derivative according to claim 3 herein designated Derivative 1 of the formula:

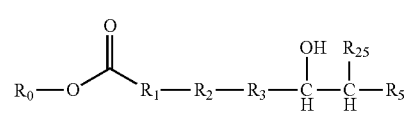

5. An amphiphilic derivative according to claim 3 of formula Ib, wherein $R_{25}$ is $-O-CO-(CH_2)_n-R_{26}$, wherein n is an integer from 1 to 14, and $R_0$, $R_1$, $R_2$, $R_3$, $R_5$ and $R_{26}$ are as defined in claim 3.

6. An amphiphilic derivative according to claim 1 of the formula Ic:

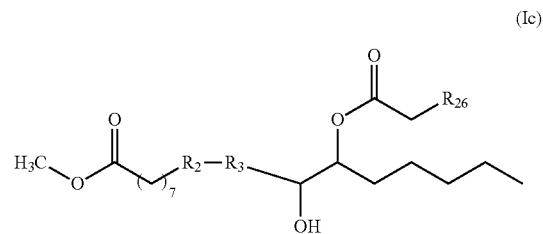

(Ic)

wherein
$R_2$ is $-CH=CH-(CH_2)_n-$ or $-CH_2-CH(X)-$, wherein X is hydrogen, halogen, or amino, and n is an integer from 0 to 7;
$R_3$ is $-CH_2-$ or $-CH(Br)-$; and
$R_{26}$ is halogen; $-NR_{22}R_{23}$; $-N^+R_{22}R_{23}R_{24}$; $-COOH$; $-SO_3H$; $-O-PO(OH)_2$; $-NH-(CH_2)_n-SO_3H$; $-NH-(CH_2)_m-COOH$; $-NH-(CH_2)_o-O-PO(OH)_2$; $-O-PO(OH)-NH-PO(OH)-O-$; $-N^+(CH_3)_2-R_{30}$; $-O-PO(OH)-O-(CH_2)_2-N^+R_{22}R_{23}R_{24}$; $-O-PO(OH)-O-(CH_2)_2-NH_3^+$; and $-O-PO(OH)-O-CH_2-CH(COO^-)-NH_3^+$; wherein n, m, and o are integers from 1 to 3; and wherein $R_{22}$, $R_{23}$, $R_{24}$, and $R_{30}$ are as defined in claim 1.

7. An amphiphilic derivative according to claim 6 herein designated Derivative 2, 3, 4, 5 and 28:

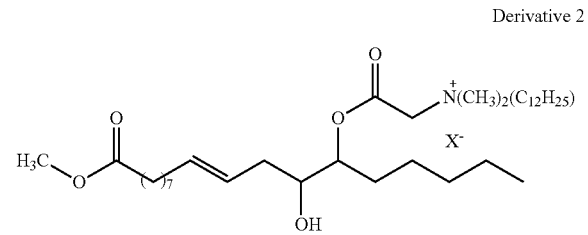
Derivative 2

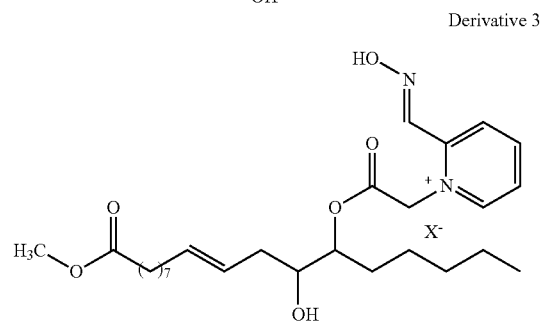
Derivative 3

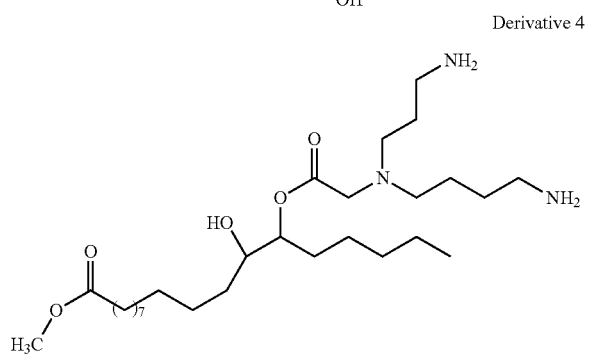
Derivative 4

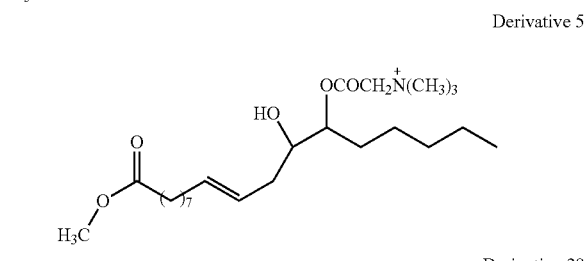
Derivative 5

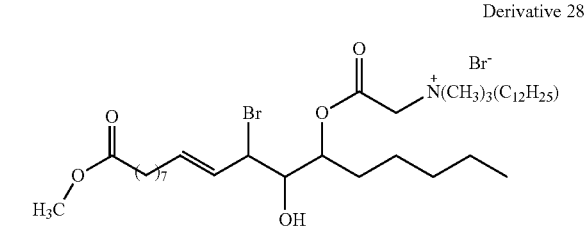
Derivative 28 wherein $X^-$ is a counter ion $Cl^-$, $Br^-$, or $I^-$.

8. An amphiphilic derivative or a precursor thereof according to claim 1 of the formula Id:

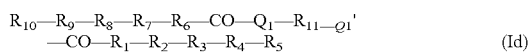
(Id)

wherein $Q_1$ and $Q_1'$, the same or different, represent —NH—, —O—, —S— or —O—PO(OH)—O—; $R_{11}$ is the spacer group $C_1$-$C_6$ alkylene or —($CH_2$—$CH_2$—NH)$_m$—$CH_2$—$CH_2$—; $R_4$ and $R_9$, the same or different, are each 2,3-oxiranylene or —CH(OH)—CH($R_{25}$)—, wherein m is an integer from 1 to 6, and $R_1$, $R_2$, $R_3$, $R_5$, $R_6$, $R_7$, $R_8$, $R_{10}$, and $R_{25}$ are as defined in claim 1.

9. An amphiphilic derivative according to claim 8, wherein $Q_1$ and $Q_1'$ are —O— and $R_{25}$ is —$N^+R_{22}R_{23}R_{24}$ or —$NR_{22}R_{23}$.

10. An amphiphilic derivative according to claim 9 herein designated Derivative 8 and Derivative 9 of the formulas:

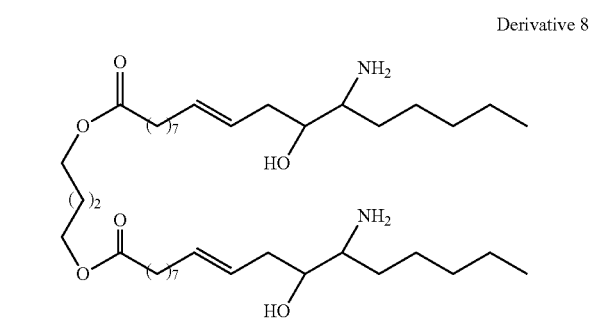
Derivative 8

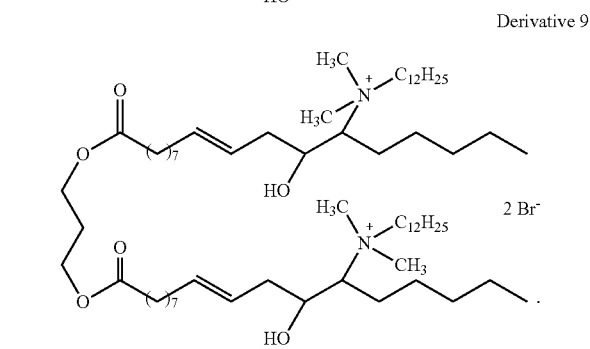
Derivative 9

11. An amphiphilic derivative according to claim 8, wherein $Q_1$ and $Q_1'$ are —NH—, and $R_{25}$ is —O—$SO_2$H.

12. An amphiphilic derivative according to claim 11 herein designated Derivative 11 of the formula:

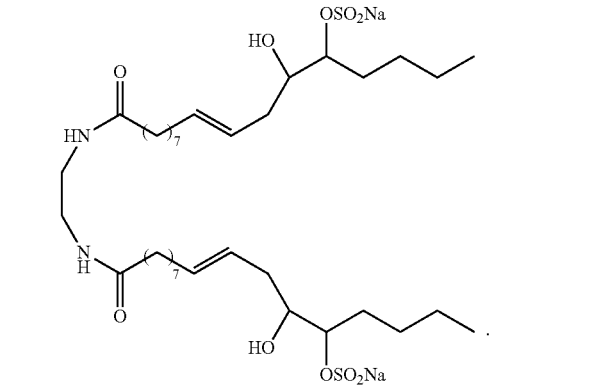

13. An amphiphilic derivative according to claim 8, wherein $Q_1$ and $Q_1'$ are —NH—; $R_4$ is —CH(OH)—CH($R_{25}$)—, and $R_9$ is —CH(OH)—CH($R'_{25}$)—, wherein $R_{25}$ and $R'_{25}$, the same or different, are each —O—CO—($CH_2$)$_n$—$R_{26}$, wherein $R_{26}$ is halogen; —$NR_{22}R$; —$N^+R_{22}R_{23}R_{24}$; —COOH; —$SO_3$H; —O—PO(OH)$_2$; —NH—($CH_2$)$_n$—$SO_3$H; —NH—($CH_2$)$_m$—COOH; —NH—($CH_2$)$_o$—O—PO(OH)$_2$; —O—PO(OH)—

NH—PO(OH)—O—; —N$^+$(CH$_3$)$_2$—R$_{30}$; —O—PO(OH)—O—(CH$_2$)$_2$—N$^+$R$_{22}$R$_{23}$R$_{24}$; —O—PO(OH)—O—(CH$_2$)$_2$—NH$_3^+$; and —O—PO(OH)—O—CH$_2$—CH(COO$^-$)—NH$_3^+$; and wherein n, m, and o are integers from 1 to 3.

14. An amphiphilic derivative according to claim 13 of the formula Ie:

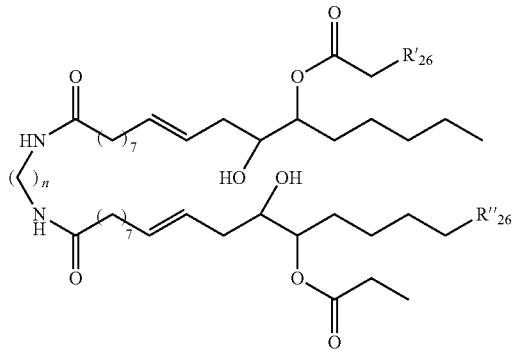

wherein n is an integer from 1 to 6, and R'$_{26}$ and R"$_{26}$, the same or different, are each as defined for R$_{26}$.

15. An amphiphilic derivative according to claim 14 herein designated Derivative 7, 10, and 12:

Derivative 7

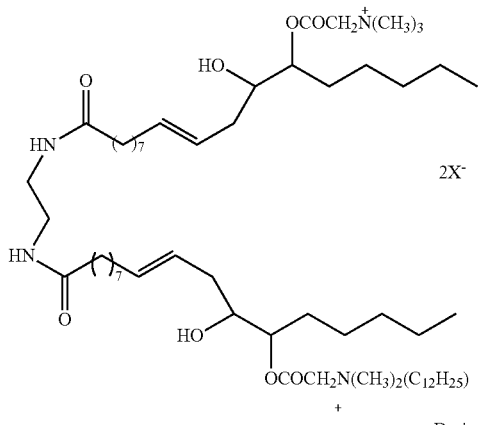

Derivative 10

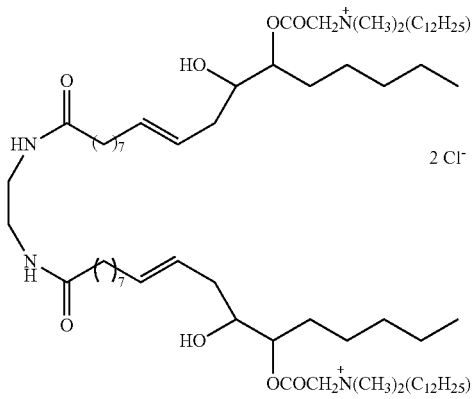

Derivative 12

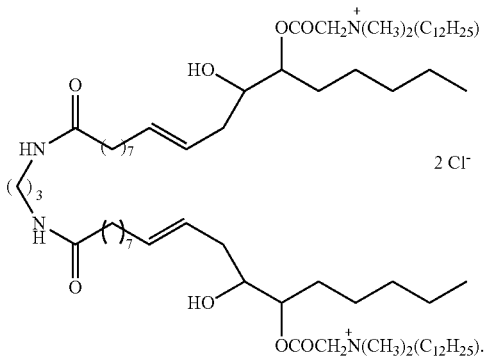

16. An amphiphilic derivative according to claim 8 of the formula Id, wherein R$_4$ and R$_9$ are each 2,3-oxiranylene and R$_{11}$ is —(CH$_2$—CH$_2$—NH)$_m$—CH$_2$—CH$_2$—, wherein m is an integer from 1 to 6.

17. An amphiphilic derivative according to claim 16 herein designated Derivative 15:

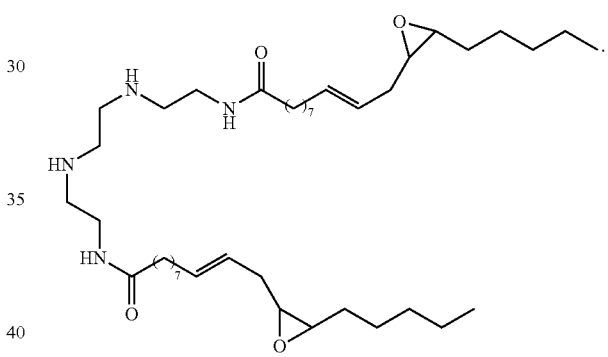

18. An amphiphilic derivative according to claim 1 of the formula If:

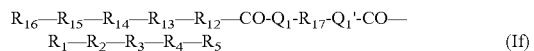

wherein

Q$_1$ and Q$_1$', the same or different, represent —NH—, —O—, —S—, or —O—PO(OH)—O—;

R$_{17}$ is —(CH$_2$)$_n$—N$^+$R$_{22}$R$_{23}$—(CH$_2$)$_m$—or (CH$_2$)$_o$—NR$_{22}$—(CH$_2$)$_p$—, wherein n, m, o and p are integers from 1 to 4; C$_1$-C$_6$ alkylene, C$_6$-C$_{24}$ arylene, —(C$_6$-C$_{14}$ arylene)—R$_{28}$—(C$_6$-C$_{14}$ arylene)—(CH$_2$—CH$_2$—O)$_n$—CH$_2$—CH$_2$—, —(CH$_2$—CH$_2$—NH)$_m$—CH$_2$—CH$_2$—, —(CH$_2$—CH$_2$—S)$_o$—CH$_2$—CH$_2$—, —(CH(CH$_3$)—CH$_2$)$_p$—, —CH(CH$_3$)—(CH$_2$)$_q$—CH(CH$_3$)—, and —CH$_2$—CH(CH$_2$—O—R$_{21}$)—, wherein the C$_6$-C$_{14}$ arylene groups may be substituted each by R$_{27}$, and n, m, o, p and q are integers from 1 to 6;

R$_4$ and R$_{15}$ independently of each other are 2,3-oxiranylene or —CH(OH)—CH(R$_{25}$)—;

and R$_1$, R$_2$, R$_3$, R$_5$, R$_6$, R$_{12}$, R$_{13}$, R$_{14}$, R$_{16}$, R$_{21}$, R$_{22}$, R$_{23}$, R$_{25}$ and R$_{28}$ are as defined in claim 1.

19. An amphiphilic derivative according to claim 18 of the formula Ig:

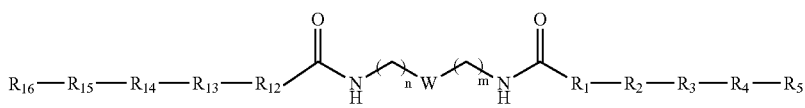

(Ig)

wherein W is $-N^+R_{22}R_{23}$ or $-NR_{22}$, n and m are integers from 1 to 4; and $R_4$ and $R_{15}$ are each 2,3-oxiranylene or $-CH(OH)-CH(R_{25})-$.

20. An amphiphilic derivative according to claim 19 herein designated Derivative 13 and 14:

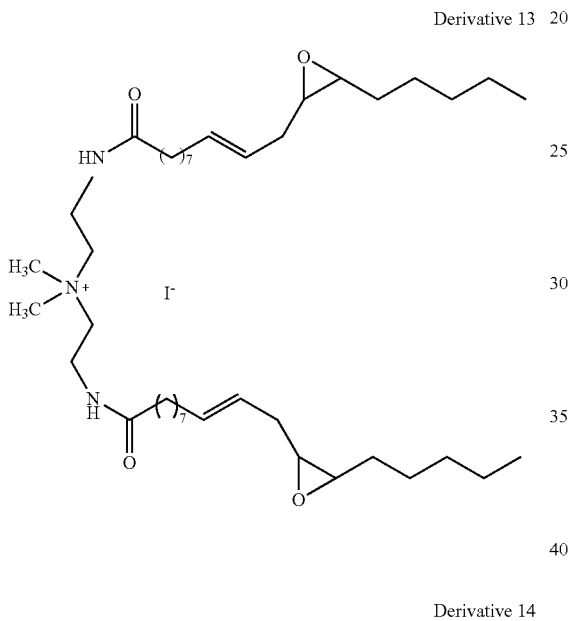

Derivative 13

Derivative 14

21. An amphiphilic derivative according to claim 1 of the formula Ih:

$$R_{18}\text{-}Q_1\text{-}R_{19}\text{-}Q_1'\text{-}CO-R_1-R_2-R_3-R_4-R_5 \quad (Ih)$$

wherein $Q_1$ represents a covalent bond, $-NH-$, $-O-$, $-S-$, or $-O-PO(OH)-O-$;

$Q_1'$ represents $-NH-$, $-S-$, or $-O-PO(OH)-O-$;

$R_4$ is 2,3-oxiranylene or $-CH(OH)-CH(R_{25})-$;

$R_{18}$ is hydrogen, $-NR_{22}R_{23}$, $-N^+R_{22}R_{23}R_{24}$, $-N=CH-(C_6\text{-}C_{14}$ arylene$)-N^+R_{22}R_{23}R_{24}$, $C_1\text{-}C_8$ alkyl, optionally substituted by $C_6\text{-}C_{14}$ aryl or $R_{29}$; $C_6\text{-}C_{24}$ aryl; $C_4\text{-}C_9$ heteroaryl containing one or more heteroatoms selected from N, O, and S, said $C_6\text{-}C_{14}$ aryl and $C_4\text{-}C_9$ heteroaryl being optionally substituted by $C_1\text{-}C_6$ alkyl, $-(CH_2)_n-NH_2$, $-COOH$, $-SH$, $-SO_3H$, $-O-SO_2H$, or $-O-PO(OH)_2$; $-(CH_2)_m-(C_6\text{-}C_{14}$ arylene$)\text{-}R_{29}$, $-(CH_2)_o-(C_6\text{-}C_{14}$ arylene$)\text{-}(CH_2)_p-R_{29}$, $-O-PO(OH)-O-CH_2-CH_2-N(CH_3)_3^+$, $-O-PO(OH)-O-CH_2-CH_2-NH_2$, or $-O-PO(OH)-O-CH_2-CH(COO^-)-NH_3^+$; wherein n is an integer from 1 to 6, m and o are integers from 1 to 20, and p is an integer from 0 to 20;

$R_{19}$ is $C_2\text{-}C_6$ alkylene, $-CH_2-(C_6\text{-}C_{14}$ arylene$)\text{-}R_{28}-(C_6\text{-}C_{14}$ arylene$)-$;

and $R_2$, $R_2$, $R_3$, $R_5$, $R_{22}$, $R_{23}$, $R_{24}$, $R_{25}$, and $R_{29}$ are as defined in claim 1.

22. An amphiphilic derivative according to claim 21, wherein $R_4$ is 2,3-oxiranylene or $-CH(OH)-CH(R_{25})-$, $R_{18}$ is hydrogen, and $R_{19}$ is $C_1\text{-}C_6$ alkylene.

23. An amphiphilic derivative according to claim 22 herein designated Derivative 16, 17, 18, 19 and Derivative 6:

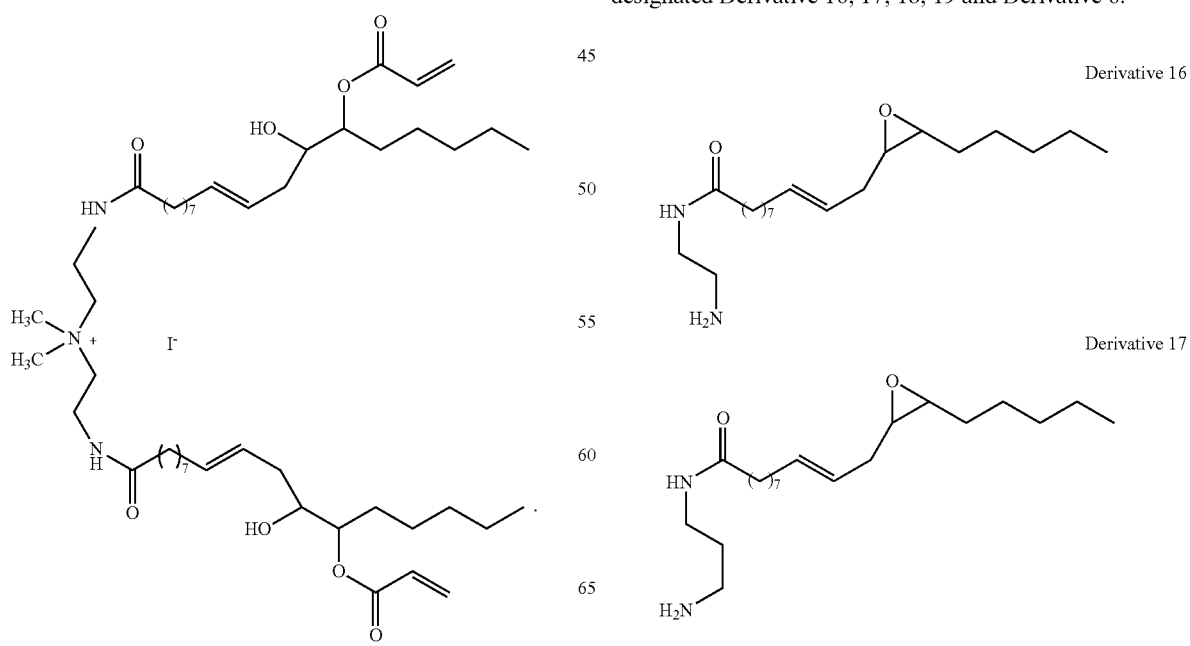

Derivative 16

Derivative 17

-continued

Derivative 18

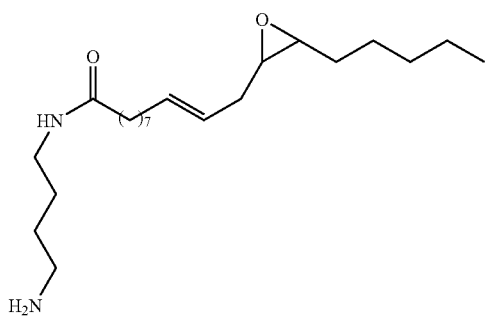

Derivative 19

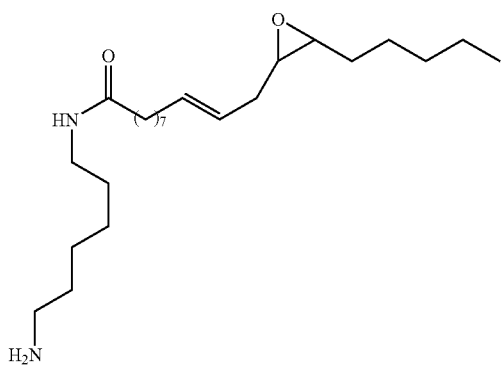

-continued

Derivative 6

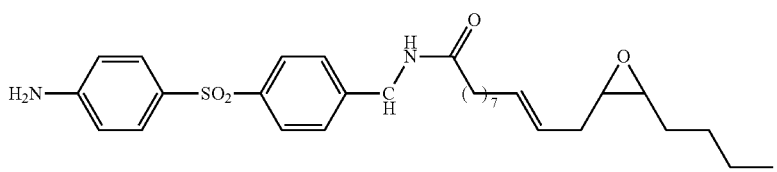

wherein X– is a counterion Cl⁻, Br⁻ or I⁻.

24. An amphiphilic derivative according to claim 21, wherein $Q_1{}'$ is —NH—; $Q_1$ is a covalent bond; $R_4$ is 2,3-oxiranylene or —CH(OH)—CH($R_{25}$)—; and $R_{18}$ is hydrogen, —$NR_{22}R_{23}$, —$N^+R_{22}R_{23}R_{24}$, or —N=C—($C_6$-$C_{14}$ Arylene)-$N^+R_{22}R_{23}R_{24}$; $R_{19}$ is $C_1$-$C_6$ alkylene or —$CH_2$—($C_6$-$C_{14}$ arylene)-$R_{28}$—($C_6$-$C_{14}$ arylene)-.

25. An amphiphilic derivative according to claim 24 herein designated Derivative 20 and 21:

Derivative 20

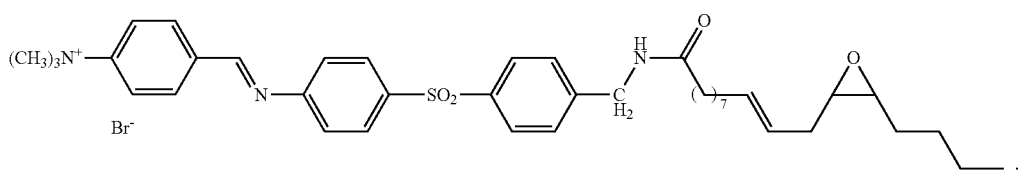

Derivative 21

26. An amphiphilic derivative according to claim 1 of the formula Ii:

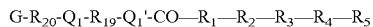
(Ii)

wherein $Q_1$ and $Q_1'$, the same or different, represent a covalent bond, —NH—, —O—, —S—, or —O—PO(OH)—O—;

$R_4$ is 2,3-oxiranylene or —CH(OH)—CH($R_{25}$)—;

$R_{19}$ is $C_1$-$C_6$ alkylene, —CH$_2$—(C$_6$-C$_{14}$ arylene) -$R_{28}$-(C$_6$C$_{14}$ arylene)-;

$R_{20}$ is $C_1$-$C_8$ alkylene, optionally substituted by $C_6$-$C_{14}$ aryl or $R_{29}$; $C_6$-$C_{14}$ arylene; or $C_4$-$C_9$ heteroarylene containing one or more heteroatom selected from N, O, and S, said $C_6$-$C_{14}$ arylene and $C_4$-$C_9$ heteroarylene being optionally substituted by $C_1$-$C_6$ alkyl, —(CH$_2$)$_n$, —NH$_2$, —COOH, —SH, —SO$_3$H, —O—SO$_2$H, or —O—PO(OH)$_2$;

G is hydrogen, or a residue of a protein, a polypeptide, an antibody, a polynucleotide, a DNA or a DNA fragment, RNA or RNA fragment, a polysaccharide, a plasmid, and or of a chemotherapeutic agent;

and $R_1$, $R_2$, $R_3$, $R_5$, $R_{24}$, $R_{28}$, and $R_{29}$ are as defined in claim 1.

27. An amphiphilic derivative according to claim 1 of the formula Ij:

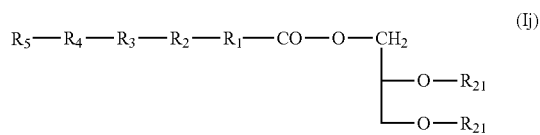
(Ij)

wherein $R_{21}$ is hydrogen, —O—PO(OH)$_2$, —O—PO(OH)—O—CH$_2$—CH$_2$—X, , or —O—PO(OH)—O—CH$_2$—CH(COO$^-$)—NH$_3^+$; and $R_1$, $R_2$, $R_3$, $R_4$, $R_5$ and X are as defined in claim 1.

28. An amphiphilic derivative according to claim 1 of the formula Ik:

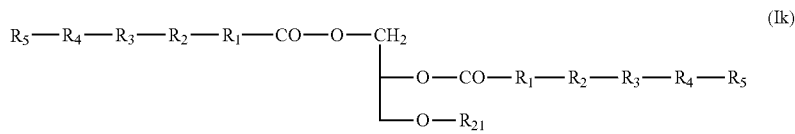
(Ik)

wherein $R_{21}$ is hydrogen, —O—PO(OH)$_2$, —O—PO(OH)—O—CH$_2$—CH$_2$—X, or —O—PO(OH)—O—CH$_2$—CH(COO$^-$)—NH$_3^+$; and $R_1$, $R_2$, $R_3$, $R_4$, $R_5$ and X are as defined in claim 1.

29. An amphiphilic derivative according to claim 28, wherein $R_2$ is —CH=CH—, $R_4$ is 2,3-oxiranylene, and $R_{21}$ is —O—PO(OH)$_2$, —O—PO(OH)—O—CH$_2$—CH$_2$—X, , or —O—PO(OH)—O—CH$_2$—CH(COO$^-$)—NH$_3^+$.

30. An amphiphilic derivative according to claim 29 herein designated Derivative 22 of the formula:

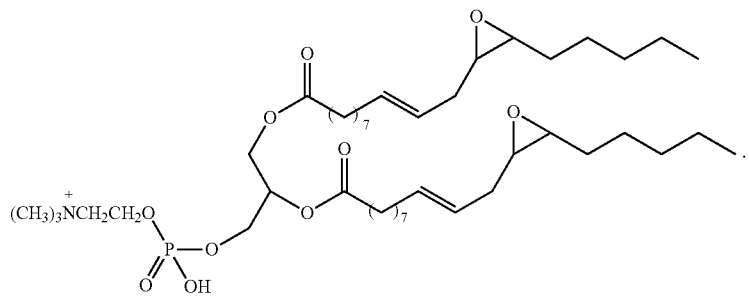

31. An amphiphilic derivative according to claim 1 of the formula Il:

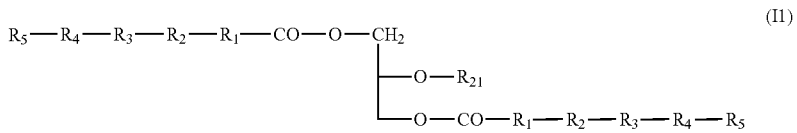

wherein $R_{21}$ is hydrogen, —O—PO(OH)$_2$, —O—PO(OH)—O—CH$_2$—CH$_2$—X, or —O—PO(OH)—O—CH$_2$—CH(COO$^-$)—NH$_3^+$; and $R_1, R_2, R_3, R_4, R_5$ and X are as defined in claim 1.

32. An amphiphilic derivative according to claim 1 of the formula Im:

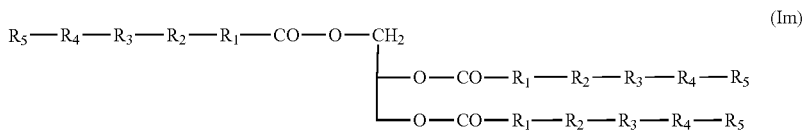

wherein $R_1$ is $C_5$-$C_{20}$ alkylene;

$R_2$ is 2,3-oxiranylene, —CH═CH—(CH$_2$)n—, —CH$_2$—CH(X)—, —CH(X)—CH(X')—, —(CH═CH—CH(X))$_m$—, —(CH$_2$—CH(X)—CH$_2$)$_o$—, or —(CH(X)—CH(X')—CH$_2$)$_p$—, wherein X and X', same or different, are hydrogen, halogen, hydroxy, amino, —O—CO—(CH$_2$)$_n$—, —R$_{26}$, or —N$^+$(R$_{22}$R$_{23}$R$_{24}$), n is an integer from 0 to 7, and m, o, and p are integers from 1 to 3;

$R_3$ is $C_1$-$C_4$ alkylene, optionally substituted by halogen, amino or hydroxy;

$R_4$ is 2,3-oxiranylene, —CH(OH)—CH(R$_{25}$)—, —CH$_2$—CH(R$_{25}$)—, —CH(OH)—CH(X)—, and —CH(OH)—CH(O—CO—R$_6$—R$_7$—R$_8$—R$_9$—R$_{10}$)—;

$R_5$ is $C_1$-$C_{11}$ alkyl, and wherein the total sum of carbon atoms in the $R_1$—$R_2$—$R_3$—$R_4$—$R_5$ chain is at most 23;

X is hydrogen, halogen, hydroxy, amino, or —N$^+$(R$_{22}$R$_{23}$R$_{24}$);

and wherein $R_6, R_7, R_8, R_9, R_{10}, R_{25}$, and $R_{26}$ are as defined in claim 1.

33. An amphiphilic derivative according to claim 32, wherein $R_4$ or $R_2$ is —CH(OH)—CH(R$_{25}$)—; $R_{25}$ is N$_3$, —O—CO—(C$_2$-C$_6$ alkenyl), —O—CO—(CH$_2$)$_n$—R$_{26}$, —(CH$_2$)$_m$—SO$_3$H, —O—SO$_2$H, —SO$_3$H, —(CH$_2$)$_o$—COOH, —(CH$_2$)$_p$—O—PO(OH)$_2$, —O—PO(OH)$_2$, —O—PO(OH)—O—(CH$_2$)$_q$—N$^+$R$_{22}$R$_{23}$R$_{24}$, —N$^+$R$_{22}$R$_{23}$R$_{24}$, —NR$_{22}$R$_{23}$, —N$^+$(CH$_3$)$_2$—R$_{30}$, —SR$_{31}$, —R$_{32}$—(C$_6$-C$_{24}$ arylene)—R$_{26}$, or —R$_{32}$—(C$_6$-C$_{24}$ arylene)—(CH$_2$)$_r$—R$_{26}$, wherein n, m, o, p, and q are integers from 1 to 14, and r is an integer from 1 to 3.

34. An amphiphilic derivative according to claim 33 herein designated Derivative 23 of the formula:

Derivative 23

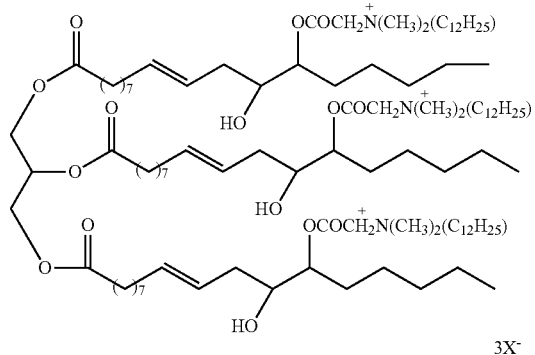

wherein X$^-$ is a counter ion Cl$^-$, Br$^-$, or I$^-$.

35. An amphiphilic derivative according to claim 33 herein designated Derivative 24 of the formula:

Derivative 24

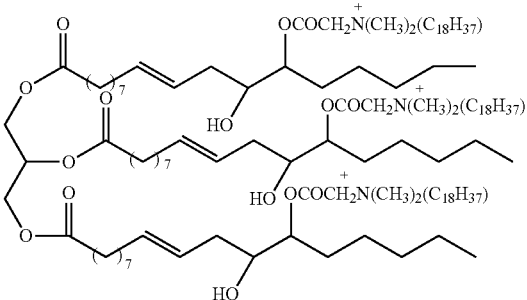

wherein X$^-$ is a counter ion Cl$^-$, Br$^-$, or I$^-$.

36. An amphiphilic derivative according to claim 33 herein designated Derivative 25 of the formula:

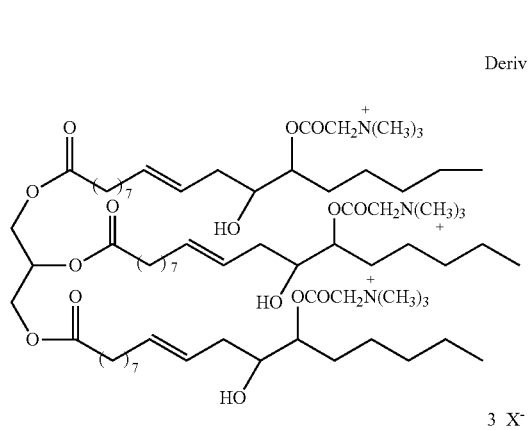

Derivative 25 wherein X⁻ is a counter ion Cl⁻, Br⁻, or I⁻.

37. An amphiphilic derivative according to claim 33 herein designated Derivative 26 of the formula:

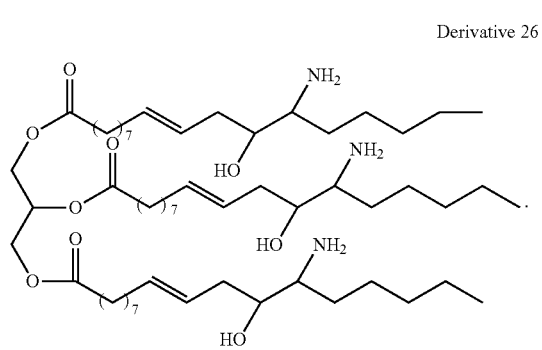

Derivative 26

38. An amphiphilic derivative according to claim 33 herein designated Derivative 27 of the formula:

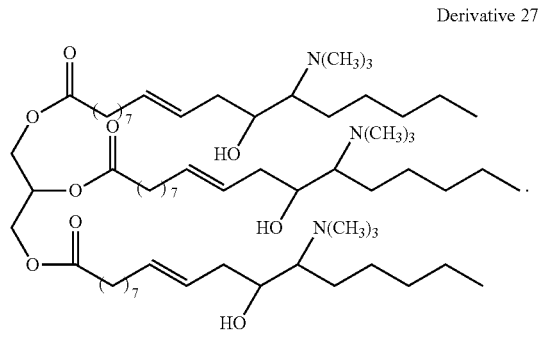

Derivative 27

39. An amphiphilic derivative according to claim 33 herein designated Derivative 30 of the formula:

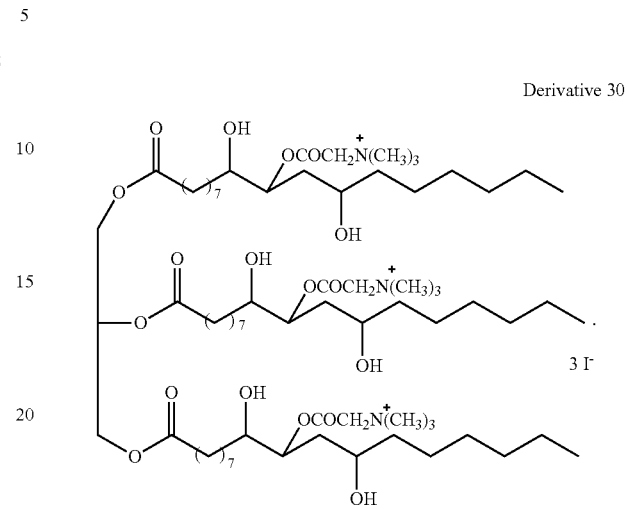

Derivative 30

40. A precursor of an amphiphilic derivative according to claim 1 herein designated Precursor 1 and 2:

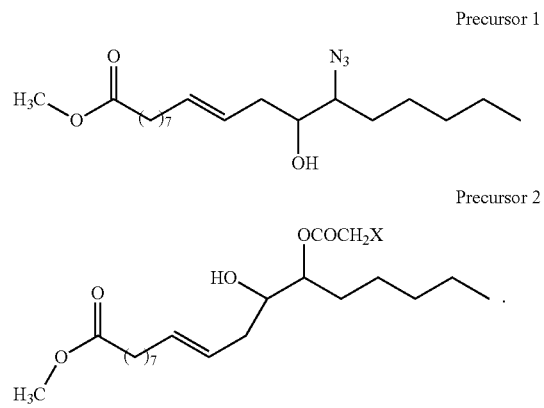

Precursor 1

Precursor 2

X = Cl, Br, I

41. A precursor according to claim 8 herein designated Precursor 3:

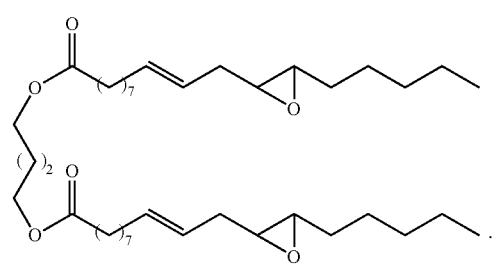

42. A precursor of an amphiphilic derivative according to claim 14 herein designated Precursor 8 when n=4, Precursor 9 when n=6, and Precursor 10 of the formula:

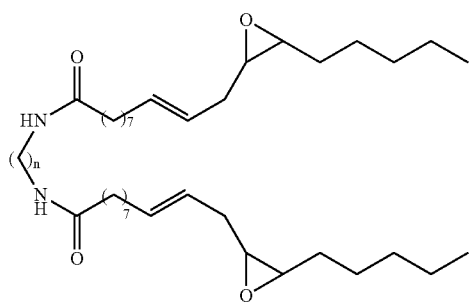

Precursor 8, n = 4
Precursor 9, n = 6

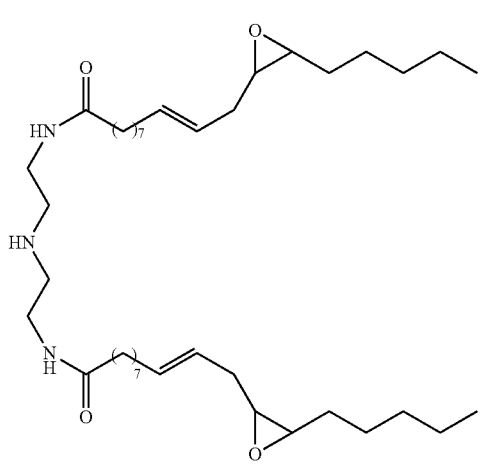

Precursor 10

43. A precursor of an amphiphilic derivative according to claim 15 herein designated Precursor 5 when n=2, and Precursor 7 when n=3 of the formula:

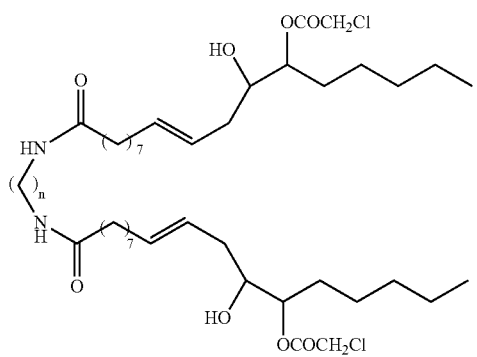

Precursor 5, n = 2
Precursor 7, n = 3

44. A precursor of an amphiphilic derivative according to claim 1 herein designated Precursor 12, 13, 14, 15, 16, 17, and 18 of the formulas:

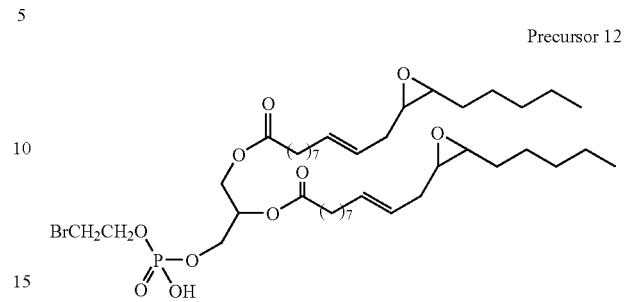

Precursor 12

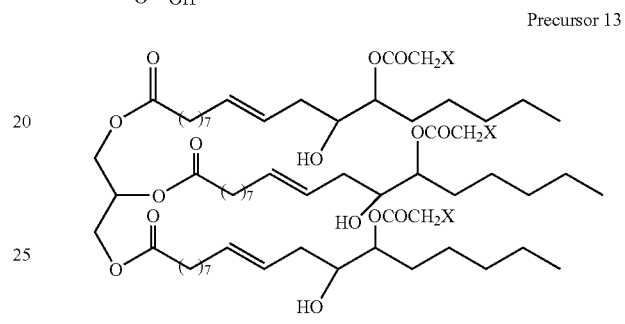

Precursor 13

X = Cl, Br, I

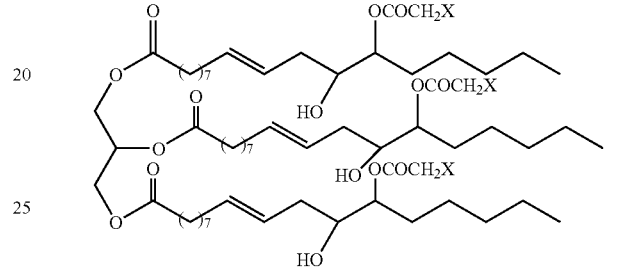

Precursor 14

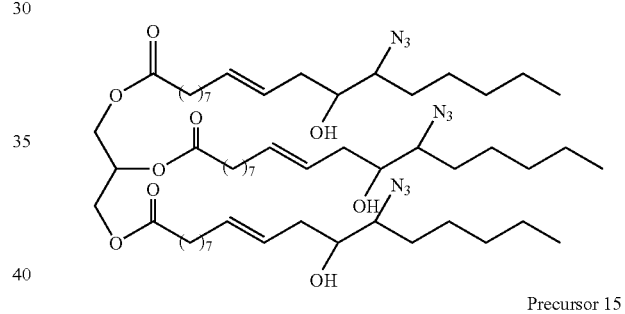

Precursor 15

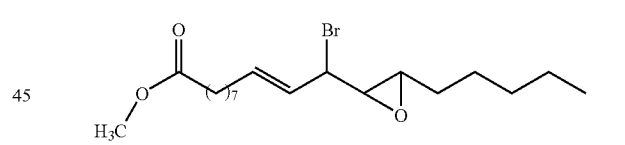

Precursor 16

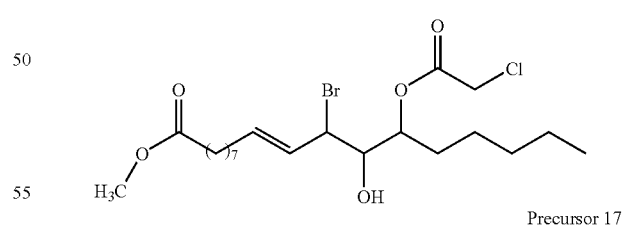

Precursor 17

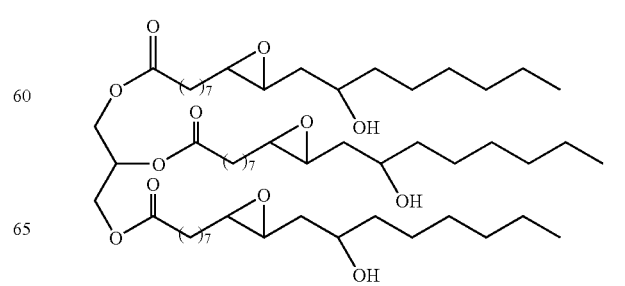

-continued

Precursor 18

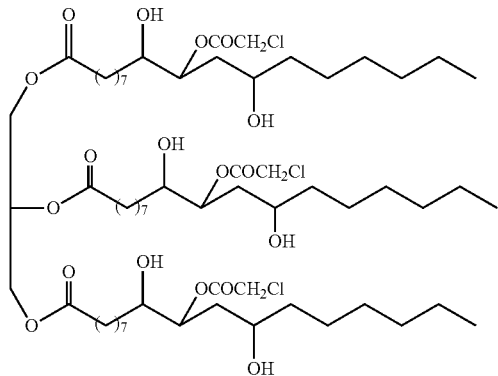

45. Vesicles, micelles, complexants and surfactants made from an amphiphilic derivative according to claim 1.

46. An amphiphilic derivative according to claim 1 or a precursor thereof, of the general Formula I:

$$A_1\text{-CO}—R_1—R_2—R_3—R_4—R_5 \qquad (I)$$

wherein
$A_1$ is —O—$R_0$;
$R_0$ is methyl;
$R_1$ is $C_7$ alkylene;
$R_2$ is —CH=CH—;
$R_3$ is methylene;
$R_4$ is —CH(OH)—CH($R_{25}$);
$R_5$ is $C_5$ alkyl;
$R_{25}$ is —O—CO—(CH$_2$)$_n$—$R_{26}$, wherein n is 1;
$R_{26}$ is —N$^+$R$_{22}$R$_{23}$R$_{24}$;
$R_{22}$ and $R_{23}$ each is methyl; and
$R_{24}$ is $C_{12}H_{25}$.

* * * * *